(12) United States Patent
Steck et al.

(10) Patent No.: US 6,262,242 B1
(45) Date of Patent: *Jul. 17, 2001

(54) TUMOR SUPPRESSOR DESIGNATED TS10Q23.3

(75) Inventors: Peter Steck, Bellaire; Mark A. Pershouse, Houston; Samar A. Jasser, Houston; W. K. Alfred Yung, Houston, all of TX (US); Sean V. Tavtigian, Salt Lake City, UT (US)

(73) Assignees: Board of Regents, The University of Texas System, Austin, TX (US); Myriad Genetics, Inc., Salt Lake City, UT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/791,115

(22) Filed: Jan. 30, 1997

(51) Int. Cl.⁷ .......................... C07H 2/04; C07K 14/475; C07K 14/47; C12Q 1/68

(52) U.S. Cl. ...................... 536/23.1; 536/23.5; 536/24.3; 536/24.33; 530/324; 435/6; 435/7.23

(58) Field of Search .................................. 536/23.5, 24.3, 536/24.33; 435/6, 7.23; 530/324

(56) References Cited

FOREIGN PATENT DOCUMENTS

WO97/15686   10/1996  (WO).

OTHER PUBLICATIONS

Finocchiaro et al. Construction of a 4.5 Mb ordered YAC contig from one putative tumor suppressor region in glioblastomas on 10q25. Am. J. Human Genetics. vol. 59, 4 suppl. p. A66, 1996.*

Russell F. Jacoby et al. "A juvenile polyposis tumor suppressor locus at 10q22 is deleted from nonepithlial cell sin the lamina propria" Gastroenterology. vol. 112, pp. 1398–1403, 1997.*

Old and Primrose. "Principles of Gene Manipulation" by Blackwell Scientific Publicaitons. pp. 239–254, 1985.*

Albarosa et al., Deletion mapping of gliomas suggest the presence of two small regions for candidate tumor–suppressor genes in a 17–cM interval on chromosome 10q. *Am. J. Genet.,* 58:1260–1267, 1996.

Bianchi et al., Mutations in transcript isoforms of the neurofibromatosis 2 gene in multiple human tumor types. *Nature Genetics,* 6:185–192, 1994.

Bigner et al., Specific chromosomal abnormalities in malignant human gliomas. *Cancer Res.,* 48:405–411, 1988.

Carter et al., Allelic loss of chromosome 16q and 10q in human prostate carcinoma. *Proc. Natl. Acad. Sci. USA,* 87:8751–8755, 1990.

Daly et al., A homozygous deletion on chromosome 3 in small cell lung cancer cell line correlates with a region of tumor suppressive activity. *Oncogene* 8:1721–1729, 1993.

El–Azouzi et al., Loss of distinct regions on the short arm of chromosome 17 associated with tumorigenesis of human astrocytomas, *Proc. Natl. Acad. Sci. USA,* 86:7186–7190, 1989.

Fujimoto et al., Loss of heterozygosity on chromosome 10 in human glioblastoma multiforme. *Genomics,* 4:210–214, 1989.

Fults et al., Molecular cytogenic analysis of a t(7;10) in a human glioblastoma cell line. *Cancer Genet. Cytogenet.* 81: 118–124. 1995.

Gray et al., Loss of chromosomal region 10q23–25 in prostate cancer. *Cancer Res.,* 55:4800–4803, 1995.

Herbst et al., Loss of heterozygosity for 10q22–qter in malignant melanoma progression. *Cancer Res.,* 54:3111–3114, 1994.

Ittmann, Allelic loss on chromosome 10 in prostate adenocarcinoma. *Cancer Res.,* 56:2143–2147, 1996.

James et al., Clonal genomic alterations in glioma malignancy stages. *Cancer Res.,* 48:5546–5551, 1988.

Karlbom et al., Loss of heterozygosity in malignant gliomas involves at least three distinct regions on chromosome 10. *Hum. Genet.,* 92:169–174, 1993.

Kimmelman et al., Loss of heterozygosity of chromosome 10p in human gliomas. *Genomics* 34:250–254, 1996.

Kok et al., A homozygous deletion in a small cell lung cancer cell line involving a 3p21 region with a marked instability in yeast artificial chromosomes. *Cancer Res.* 54:4183–4187, 1994.

Lacombe et al., Microsatellite instability and deletion analysis of chromosome 10 in human prostate cancer. *Int. J. Cancer (Pred. Oncol.)* 69:110–113, 1996.

Lee et al., Human retinoblastoma susceptibility gene: cloning, identification, and sequence. *Science,* 235:1394–1399, 1987.

(List continued on next page.)

Primary Examiner—Anthony C. Caputa
Assistant Examiner—Karen A. Canella
(74) *Attorney, Agent, or Firm*—Rothwell, Figg, Ernst & Manbeck, p.c.

(57) ABSTRACT

A specific region of chromosome 10 (10q23.3) has been implicated by series of studies to contain a tumor suppressor gene involved in gliomas, as well as a number of other human cancers. One gene within this region was identified, and the corresponding coding region of the gene represents a novel 47 kD protein. A domain of this product has an exact match to the conserved catalytic domain of protein tyrosine phosphatases, indicating a possible functional role in phosphorylation events. Sequence analyses demonstrated the a number of exons of the gene were deleted in tumor cell lines used to define the 10q23.3 region, leading to the classification of this gene as a tumor suppressor. Further analyses have demonstrated the presence of a number of mutations in the gene in both glioma and prostate carcinoma cells. Methods for diagnosing and treating cancers related to this tumor suppressor, designated as TS10q23.3, also are disclosed.

32 Claims, 33 Drawing Sheets

OTHER PUBLICATIONS

Morita et al., Common regions of deletion on chromosomes 5q, 6q, and 10q in renal cell carcinoma. *Cancer Res.*, 51:5817–5820, 1991.

Murakami et al., Suppression of the malignant phenotype of human prostate cancer cell line PPC–1 by introduction of normal fragments of human chromosome 10. *Cancer Res.*, 56:2157–2160, 1996.

Nishi et al., Differential expression of two types of the neurofibromatosis type 1 gene transcripts related to neuronal differentiation. *Oncogene*, 6:1555–1559, 1991.

Peiffer et al., Allelic loss of sequences from the long arm of chromosome 10 and replication errors in endometrial cancers. *Cancer Res.*, 55:1922–1926, 1995.

Pershouse et al., "Allelic mapping of a tumor suppressing region on chromosome 10q in human glioblastomas", *The American Journal of Human Genetics*, 57(4):174, Abs. #400, 1995.

Pershouse et al., Analysis of the functional role of chromosome 10 loss in human glioblastomas. *Cancer Res.* 53:5043–5050, 1993.

Pershouse, et al., "Functional Localization of Tumor Suppressor Genes on Chromosome 10 in Human Glioblastoma", Proceedings of the American Association for Cancer Research, 35:174, Abs. 1043, 1994.

Petersen et al., Small–cell lung cancer is characterized by a high incidence of deletions on chromosomes 3p, 4q, 5q, 13q, and 17p. *Brit. J. Cancer* 75:79–86, 1997.

Rasheed et al., Chromosome 10 deletion mapping in human gliomas: a common deletion region in 10q25. *Oncogene*, 10:2243–2246, 1995.

Rempel et al., Loss of heterozygosity for loci on chromosome 10 is associated with morphologically malignant meningioma progression. *Cancer Res.*, 53:2386–2392, 1993.

Rubio et al., Analysis of the neurofibromatosis 2 gene in human ependymonas and astrocytomas, *Cancer Res.*, 54:45–47, 1994.

Sanchez et al., Tumor suppression and apoptosis of human prostate cacinoma mediated by a gentic locus within human chromosome 10pter–q11. *Proc. Natl. Acad. Sci. USA*, pp. 2551–2556, 1996.

Scheck and Coons, Expression of the tumor suppressor gene DCC in human gliomas. *Cancer Res.*, 53:5605–5609, 1993.

Sonoda et al., Loss of heterozygosity at 11p15 in malignant glioma. *Cancer Res.*, 55:2166–2168, 1995.

Steck et al., "Functional Roles of and Localization of chromosome 10 Deletions in Human Glioblastomas", *Journal of Cellular Biochemistry*, Supp. 18A:211, Abs. #D 605, 1994.

Tam et al., $S_N2$ deprotection of synthetic peptides with a low concentration of HF in dimethyl sulfide: evidence and application in peptide synthesis. *J. Am. Chem. Soc.*, 105:6442–6455, 1983.

Trybus et al., Distinct areas of allelic loss on chromosomal regions 10p and 10q in human prostate cancer. *Cancer Res.* 56:2263–2267, 1996.

von Deimling et al., Deletion mapping of chromosome 19 in human gliomas. *Int. J. Cancer*, 57:676–680, 1994.

Voullaire et al.,A functional marker centromere with no detectable alpha–satellite, satellite III, or CENP–B protein: activation of a latent centromere? *Am. J. Hum. Genet.*, 52:1153–1163, 1993.

Watling et al., Loss of heterozygosity analysis of chromosomes 9,10 and 17 in gliomas in families. *Can. J. Neurol. Sci.* 22:17–21. 1995.

Wei et al., Construction of a 600–kilobase cosmid clone contig and generation of a transcriptional map surrounding the lung cancer tumor suppressor gene (TSG) locus on human chromosome 3p21.3: progress toward the isolation of a lung cancer TSG. *Cancer Res.* 56:1487–1494, 1996.

* cited by examiner

```
CCTCCCCTCGCCCGGCGGCGTCCCGTCCGCTCCGCTCCCCCCCCTCGGCTCTTCCGAGGCGCCCCGGCTCCCGGGCGCGGGGAGGGGG      100
CGGGCAGGCCCGGCCCGCTGATGTGGCTGCAGGACTCTTTATGCGCTGCGGGACGCGCTGCCTGGGACTGCCGCTCAGTTCTCTCCTC      200
GGAAGCTGCAGCCATGATGGAAGTTGAGCTTGAGCAGCCGCGGCTCAGGGAGCCCGGGGCGAGGGAGATGAGAGACGGGCGGCCCGGA      300
GCCCCTCTCAGCGCCTGTGAGCAGCCGCGGGGACCGGCCTGCCGGGGAGCCCAGCGGCGCGTTTCTCGCTCCTCTTCGT          400
CTTTTCTAACCGTGCAGCCTCTTCCTCCGCTTCCCTGAAAGGGAAGTGGAAGCCGCGGGCGCGGGGAGCTCCAGGGAGGGGTCTGAGCCGG      500
CGGCACCTCCCGCTCCCGGTCCTGGAGCGGGGAGAAGCGGCGGGCCCCTCTACTGCCTCCAACACGCGGGCACATCCAGGGACCCATTT      600
CCAGGGCTGGAACGCCCGGAGAGTTGGTCTCTCCCCCGTGGCCACCCCCCGGGCTCCGGAGAAGCAGCCCAGTCGCTGCAGCCATCCGA      700
CCTCCCGTCCGCCCGCCACCCCCGTGGCCCAGCCCTCTGCTGCTGAGGAGAAGCAGGCCCCAGTCGCTGCAGCCATCCAGCAGCCCGCC      800
GCCGCGCTGCCAGGCCCTCTGCTGTGCCGAGCGGGGCATCAGCTCCAGAGCCATTCCATCCTCCAGAGAAGCCCCGCCCAGCAGCTTCTGCCATCT      900
GCCAAGCGGCGGCAGAGCGAGGGGCATCAGCTCCCAAGTCCAGAGACATCACATCCCCCAGACACATGACAGCCCAGATATCAAGAGGATGGATTCGAC     1000
CTCCCTCCTTTTCTTCAGCCAGGCTCCCACAGGCTCCCCAGACAGCCTCCCAGACACATGACAGCCCAGATATCAAGAGGATGGATTCGAC     1100
TTAGACTTGACCTATATTTATCCAAACATTATTGCTATGGGATTTCCTGCAGAAAGACTTGAAGGCGTATACAGGAACAATATTGATGATGTAGTAAGGT     1200
TTTTGGATTCAAAGCATAAAAAACCATTACAAGATATACAATCTTTGTGCTGAAAGACATTATGACACCGCCAAATTTAATTGCAGAGTTGCACAATATCC     1300
TTTTGAAGACCATAACCCACCACCAGCTAGAACTTATCAAACCCTTTTGTGAAGATCTTGACCAATGCTAAGTGAAGATGACAATCATGTTGCAGCAATT     1400
CACTGTAAAGCTGGAAAGGACGAACTGGTGTAATGATATGTGCATATTATTACATCGGGGCAAATTTTTAAAGGCACAAGAGGCCCTAGATTTCTATG     1500
GGGAAGTAAGGACCAGAGACAAAAAGGGAGTAACTATTCCCAGTCAGAGGCGCTATGTGTATTATTATAGCTACCTGTTAAAGAATCATCTGGATTATAG     1600
ACCAGTGGCACTGTGTTCACAAGATGATGTTTGAAACTATTCCAATGTTCAGTGGCCGGAACTTGCAATCCTCAGTTGTTGTGCTGCCAGCTAAAGGTG     1700
```

FIG. 6A

```
AAGATATATTCCTCCAATTCAGGACCCACACGACGGAAGACAAGTTCATGTACTTTGAGTTCCCTCAGCCGTTACCTGTGTGTGGTGATATCAAAGTAG  1800

AGTTCTTCCACAAACAGAGAACAAGATGCTAAAAAGGACAAAATGTTCACTTTTGGGTAAATACATTCTTCATACCAGGACCAGAGGAAACCTCAGAAAA  1900

AGTAGAAAATGGAAGTCTATGTGATCAAGAAATCGATAGCATTTGCAGTATAGAGCCGTGCAGATAATGACAAGGAATATCTAGTACTTACTTTAACAAAA  2000

AATGATCTTGACAAAGCAAATAAAGACAAAGCCAACCGATACTTTTCTCCAAATTTAAGGTGAAGCTGTACTTCACAAAAACAGTAGAGGAGCCGTCAA  2100

ATCCAGAGGCTAGCAGTTCAACTTCTGTAACACCAGATGTTAGTGACAATGAACCTGATCATTATAGATATTCTGACACCACTGACTCTGATCCAGAGAA  2200

TGAACCTTTTGATGAAGATCAGCATACACAAATTACAAAAGTCTGAATTTTTTTATCAAGAGGATAAAACACCATGAAAATAAACTTGAATAAACTG  2300
AAAATGACCTTTTTTTTTAATGCAATTGTGTCAGTTATAGGACATTCTCTTTCCTGACCAGTTATACCCAGTTGTGTCAGATTATACACTTTTTGTCAATGTAGAATTCTCTTTGTTTACCCTATA  2400
CATCCACAGGGTTTGACACTTGTTGTCCAGTTGAAAAAAGGTTGTGTAGCTGTCATGTATAAAAGGACAGAGCAGACTGATGTGTATAAAAGGACATTAAAATTCAAT  2500
TAGGATTAATAAAGATGGCACTTTCCCGTTTTATTCCAGTTGATATACTGGTTCACATCGATATATCTGGTTCACATCGTTATAAAAAGTGGAGACAGAGCAGACTGATGTGTATACGTAGGAATTTTTTCCTTTTGTTCT  2600
GTCACCAACTGAAGTGGCTAAAGAGCTTTGTGATATACTGGTTCACATCGATATATCTGGTTCACATCGTGTAATACGTAGGAATTTTTTCCTTTTGTTCTCAACAGATAAGTTGCAGTTGGCTAAGAGAG  2700
GTTTCCGAAAGGTTTTGCTACCATTCTAATGCATGTATTCGGTTAGGCAATGCTCAGAAGGGAATGCTCAGAAAATAATTTATGCTGACTCTGAC  2800
CATATACCATCTCCAGCTATTACACACCTTTCTTTAGCATGCTACAGTTATTAATCTGGACATTCGAGGGTACAGGAATCTGTATTGGGTACAGGAATGAACCTTCTGCAACATCTTAAGAT  2900
GCGCATTTTTTTAAAGCATATTGGTGCTAGAAAAGGCAATGTCATAGGTAAGAACACAGCAACAATGACTTAACCATATAAATGTGGAGGCTATCAACAAAGAATGGGCTTG  3000
CCACAAATGAAGGGATATAAAATAAAAAATAATGACAATGATTTATTAAAGCATATTGTTTCTCAATTGTAAAAAAAAA  3100
AACATTATAAAAATTGACAATGATTTATTAAATATGTTTTCTCAATTGTAAAAAAAAA
```

| | 1130 | 1140 | 1150 | 1160 | 1170 | 1180 | 1190 | 1200 | 1210 |
|---|---|---|---|---|---|---|---|---|---|
| 6 C6.1.HUMAN | ATCATTA | TAGATATTCT | GACACCACTG | ACTCTGATCC | AGAGAATGAA | CCTTTTGATG | AAGATCAGCA | TACACAAATT | ACAAAAGTCT GAA |
| 3 C6.1.MOUSE | ATCATTA | TAGATATTCT | GACACCACTG | ACTCTGATCC | AGAGAATGAA | CTTTTTGATG | AAGATCAGCA | TTCACAAATT | ACAAAAGTCT GA |
| 37 C6.1.DOG | ATCATTA | TAGATATTCT | GACACCACTG | ACTCTGACCC | AGAGAATGAA | CCCTTTGATG | AAG | | |
| 38 NT.COMP | | | ---- | -----*--- | | -----*-- | | -*--- | |
| 44 HUMAN.PEP | H Y | R Y S | D T T D | S D P | E N E | P F D | D Q H | T Q I | T K V * |
| 46 MOUSE.PEP | H Y | R Y S | D T T D | S D P | E N E | P F D | D Q H | T S I | T K V * |
| 39 DOG.PEP | H Y | R Y S | D T T D | S D P | E N E | P F D | D | | |
| 48 PEP.COMP | | | ---- | ---*- | | -*-- | | -*--- | -----*- |
| 15 TS10q23.3.PEP | H Y | R Y S | D T T D | S D P | E N E | P F D | D Q H | T Q I | T K V * |
| | 1220 | 1230 | 1240 | 1250 | 1260 | 1270 | 1280 | 1290 | 1300 |
| 6 C6.1.HUMAN | TTTTTTTT | TTATCAAGAG | GGATAAAACA | CCATGAAAAT | AAACTGAAAA | TGGACCTTTT | TTTTTTTAAT | GGCAATAGGA | CAT |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |
| | 1310 | 1320 | 1330 | 1340 | 1350 | 1360 | 1370 | 1380 | 1390 |
| 6 C6.1.HUMAN | TGTGTCA | GATTACCAGT | TATAGGAACA | ATTCTCTTTT | CCTGACCAAT | CTTGTTTTAC | CCTATACATC | CACAGGGTTT | TGACACTTGT TGT |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |
| | 1400 | 1410 | 1420 | 1430 | 1440 | 1450 | 1460 | 1470 | 1480 |
| 6 C6.1.HUMAN | CCAGTTG | AAAAAAGGTT | GTCTAGCTGT | GTCATGTATA | TACCTTTTTG | TGTCAAAAGG | ACATTTAAAA | TTCAATTAGG | AITAATAAAG ATG |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1490 | 1500 | 1510 | 1520 | 1530 | 1540 | 1550 | 1560 | 1570 |
|---|---|---|---|---|---|---|---|---|---|
| 6 C6.1.HUMAN | GCACTTT | CCCGTTTTAT | TCCAGTTTTA | TAAAAAGTGG | AGACAGACTG | ATGTGTATAC | GTAGGAATTT | TTTCCTTTTG | TGTTCTGTCA CCA |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |
| | 1580 | 1590 | 1600 | 1610 | 1620 | 1630 | 1640 | 1650 | 1660 |
| 6 C6.1.HUMAN | ACTGAAS | TGGCTAAAGA | GCTTTGTGAT | ATACTGGTTC | ACATTCTACC | CCTTTGCCACT | TCTGGGCAAACA | GATAAGTTTG | CAGTTGGCTA AGA |
| 3 C6.1.MOUSE | ↓↓↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |
| | 1670 | 1680 | 1690 | 1700 | 1710 | 1720 | 1730 | 1740 | 1750 |
| 6 C6.1.HUMAN | GAGGTTT | CCGAAAGGTT | TTGCTTACCAT | TCTAATGCAT | GTATTCGGGT | TAGGGCAATG | GAGGGGAATG | CTCAGAAAGG | AAATAATTTT ATG |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |
| | 1760 | 1770 | 1780 | 1790 | 1800 | 1810 | 1820 | 1830 | 1840 |
| 6 C6.1.HUMAN | CTGGACT | CTGGACCATA | TACCATCTCC | AGCTATTTAC | ACACACCTTT | CTTTAGCAATG | CTACAGTTAT | TAATCTGGAC | ATTCGAGGAA TTG |
| 3 C6.1.MOUSE | ↓ | | | | | | | | |
| 37 C6.1.DOG | | | | | | | | | |
| 38 NT.COMP | ↓↓↓↓↓ | | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

FIG. 9I

| | 1850 | 1860 | 1870 | 1880 | 1890 | 1900 | 1910 | 1920 | 1930 |
|---|---|---|---|---|---|---|---|---|---|
| 6 C6.1.HUMAN | GCCGCTG | TCACTGCTTG | TTGTTTGCGC | ATTTTTTTTT | AAAGCATATT | GGTGCTAGAA | AAGGCAGCTA | AAGGAAGTGA | ATCTGTATTG GGG |
| 3 C6.1.MOUSE | ↓ | | | | | | | | |
| 37 C6.1.DOG | | | | | | | | | |
| 38 NT.COMP | ↓ | ↓ | ↓ | ↓ | ↓ | | | | --- |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 1940 | 1950 | 1960 | 1970 | 1980 | 1990 | 2000 | 2010 | 2020 |
|---|---|---|---|---|---|---|---|---|---|
| 6 C6.1.HUMAN | TACAGGA | ATGAAACCTTC | TGCAACATCT | TAAGATCCAC | AAATGAAGGG | ATATAAAAAT | AATGTCATAG | GTAAGAAACA | CAGCAACAAT GAC |
| 3 C6.1.MOUSE | ↓ | | | | | | | | |
| 37 C6.1.DOG | ↓ | ↓ | | | | | | | |
| 38 NT.COMP | ↓ | ↓ | ↓ | ↓ | | | | | --- |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 2030 | 2040 | 2050 | 2060 | 2070 | 2080 | 2090 | 2100 | 2110 |
|---|---|---|---|---|---|---|---|---|---|
| 6 C6.1.HUMAN | TTAACCA | TATAAATGTG | GAGGCTATCA | ACAAAGAATG | GGCTTGAAAC | ATTATAAAAA | TTGACAATGA | TTTATTAAAT | ATGTTTTCTC AAT |
| 3 C6.1.MOUSE | ↓ | | | | | | | | |
| 37 C6.1.DOG | ↓ | ↓ | | | | | | | |
| 38 NT.COMP | ↓ | ↓ | ↓ | ↓ | | | | | --- |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

| | 2120 | 2130 | 2140 | 2150 | 2160 | 2170 | 2180 | 2190 | 2200 |
|---|---|---|---|---|---|---|---|---|---|
| 6 C6.1.HUMAN | TGTAAAA | AAAAAA | | | | | | | |
| 3 C6.1.MOUSE | ↓ | | | | | | | | |
| 37 C6.1.DOG | ↓ | ↓ | | | | | | | |
| 38 NT.COMP | ↓ | ↓ | | | | | | | |
| 44 HUMAN.PEP | | | | | | | | | |
| 46 MOUSE.PEP | | | | | | | | | |
| 39 DOG.PEP | | | | | | | | | |
| 48 PEP.COMP | | | | | | | | | |
| 15 TS10q23.3.PEP | | | | | | | | | |

|  |  | -1030 | -1020 | -1010 | -1000 | -990 | -980 | -970 | -960 | -950 |  |
|---|---|---|---|---|---|---|---|---|---|---|---|
| 1 | CA6.CG01.XAIA | CCTC | CCCTCGCCCG | GGGGGTCCC | GTCCGCCCT | CGCTCGCCTC | CCGCCTCCCC | TCGGTCTTCC | GAGGCGCCCC | GGCTCCCGGC | GCCGCG |
| 2 | CA6.CG01.IAXBIB |  |  |  |  |  |  |  |  |  | ↑ |
| 3 | CA6.CG01.IBXCIC |  |  |  |  |  |  |  |  |  | ↑ |
| 4 | CA6.CG01.ICXDID |  |  |  |  |  |  |  |  |  | ↑ |
| 5 | CA6.CG01.IDXEIE |  |  |  |  |  |  |  |  |  | ↑ |
| 6 | CA6.CG01.IEXFIF |  |  |  |  |  |  |  |  |  | ↑ |
| 7 | CA6.CG01.IFXGIG |  |  |  |  |  |  |  |  |  | ↑ |
| 8 | CA6.CG01.IGXHIH |  |  |  |  |  |  |  |  |  | ↑ |
| 9 | CA6.CG01.IHXI |  |  |  |  |  |  |  |  |  | ↑ |

|  |  | -940 | -930 | -920 | -910 | -900 | -890 | -880 | -870 | -860 |  |
|---|---|---|---|---|---|---|---|---|---|---|---|
| 1 | CA6.CG01.XAIA | GCGG | AGGGGGCGGG | CAGGCCGGCG | GGGGGTGATG | TGGCAGGACT | CTTTATGCGC | TCCGCAGGA | TACGCCCTCG | GCGCTGGGAC | GCGACT |
| 2 | CA6.CG01.IAXBIB |  |  |  |  |  |  |  |  |  | ↑ |
| 3 | CA6.CG01.IBXCIC |  |  |  |  |  |  |  |  |  | ↑ |
| 4 | CA6.CG01.ICXDID |  |  |  |  |  |  |  |  |  | ↑ |
| 5 | CA6.CG01.IDXEIE |  |  |  |  |  |  |  |  |  | ↑ |
| 6 | CA6.CG01.IEXFIF |  |  |  |  |  |  |  |  |  | ↑ |
| 7 | CA6.CG01.IFXGIG |  |  |  |  |  |  |  |  |  | ↑ |
| 8 | CA6.CG01.IGXHIH |  |  |  |  |  |  |  |  |  | ↑ |
| 9 | CA6.CG01.IHXI |  |  |  |  |  |  |  |  |  | ↑ |

|  |  | -850 | -840 | -830 | -820 | -810 | -800 | -790 | -780 | -770 |  |
|---|---|---|---|---|---|---|---|---|---|---|---|
| 1 | CA6.CG01.XAIA | GCGC | TCAGTTCTCT | CCCTCTCGGAA | GCTGCAGCCA | TGATGGAAGT | TTGAGAGTTG | AGCCCCTGTG | AGGGAGGCC | GGGCTCAGGC | GAGGGA |
| 2 | CA6.CG01.IAXBIB |  |  |  |  |  |  |  |  |  | ↑ |
| 3 | CA6.CG01.IBXCIC |  |  |  |  |  |  |  |  |  | ↑ |
| 4 | CA6.CG01.ICXDID |  |  |  |  |  |  |  |  |  | ↑ |
| 5 | CA6.CG01.IDXEIE |  |  |  |  |  |  |  |  |  | ↑ |
| 6 | CA6.CG01.IEXFIF |  |  |  |  |  |  |  |  |  | ↑ |
| 7 | CA6.CG01.IFXGIG |  |  |  |  |  |  |  |  |  | ↑ |
| 8 | CA6.CG01.IGXHIH |  |  |  |  |  |  |  |  |  | ↑ |
| 9 | CA6.CG01.IHXI |  |  |  |  |  |  |  |  |  | ↑ |

|  |  | -760 | -750 | -740 | -730 | -720 | -710 | -700 | -690 | -680 |  |
|---|---|---|---|---|---|---|---|---|---|---|---|
| 1 | CA6.CG01.XAIA | GATG | AGAGACGGG | GCGGCCGCGG | CCCGGAGCCC | CTCTCAGCCGC | CTCTGACCAG | CCCGGGGGC | AGCCCCTTCG | GGGAGCCCGC | CGGCCT |
| 2 | CA6.CG01.IAXBIB |  |  |  |  |  |  |  |  |  | ↑ |
| 3 | CA6.CG01.IBXCIC |  |  |  |  |  |  |  |  |  | ↑ |
| 4 | CA6.CG01.ICXDID |  |  |  |  |  |  |  |  |  | ↑ |
| 5 | CA6.CG01.IDXEIE |  |  |  |  |  |  |  |  |  | ↑ |
| 6 | CA6.CG01.IEXFIF |  |  |  |  |  |  |  |  |  | ↑ |
| 7 | CA6.CG01.IFXGIG |  |  |  |  |  |  |  |  |  | ↑ |
| 8 | CA6.CG01.IGXHIH |  |  |  |  |  |  |  |  |  | ↑ |
| 9 | CA6.CG01.IHXI |  |  |  |  |  |  |  |  |  | ↑ |

|   |   | 410 | 420 | 430 | 440 | 450 | 460 | 470 | 480 | 490 |
|---|---|---|---|---|---|---|---|---|---|---|
| 1 | CA6.CG01.XAIA | tagg | cttaaatcc | tagagtggat | ttattcagtt | aaatttattc | acactgaagat | gtngatgact | aatactgtat | attttatgt agacca |
| 2 | CA6.CG01.IAXBIB | ttat | cctgtgtctc | tagagctatt | gactgaaaaa | gctgttaggg | cattctctaa | ctgtacatca | cctaagttat | ttaaaattgc tgaatt |
| 3 | CA6.CG01.IBXCIC | taaa | agctatgaaa | ggatataac | | | | | | |
| 4 | CA6.CG01.ICXDID | NNNN | NNNNNNNNN | NNNNNNNNN | NNNNNNNNN | NNNNNNNNN | NNNNNNNNN | NNNNNNNNN | NNNNNNNNN | NNNNNNN |
| 5 | CA6.CG01.IDXEIE | agcc | caatttctga | ctagatgtat | ggaagaacct | gtccc | | | | |
| 6 | CA6.CG01.IEXFIF | ttag | catgggacca | atattttaaa | aatttttggt | ctatagttag | aaatgagatc | tgttctgtgg | tcttatgtag | tgacaccaaac cac |
| 7 | CA6.CG01.IFXGIG | gtca | aaaagtgc | attttttcctt | ttcctaattc | tttgtgttt | gctgaaatct | gggcaaagg | tgcgggagg | ggctaaatga ctggga |
| 8 | CA6.CG01.IGXHIH | cttt | ttgtgtcaaa | aggacattta | aaattcaatt | aggattaata | aagatgcac | tttcccgttt | tattccagtt | ttataaaaag tggaga |
| 9 | CA6.CG01.IHXI |  |  |  |  |  |  |  |  |  |

|   |   | 500 | 510 | 520 | 530 | 540 | 550 | 560 | 570 | 580 |
|---|---|---|---|---|---|---|---|---|---|---|
| 1 | CA6.CG01.XAIA | aatt | ttaaggtacc | actgtgcata | tgtntaccaa | ctacctgaag | aantatttgg | ttggtacnag | anatatataa | aggaatcgct ngtgt |
| 2 | CA6.CG01.IAXBIB | aagt | ggctgtgctt | gtctangaca | gmttttaag | gactgccaac | ctgattgata | gaactagttg | accttatctt | taacttttg tfttct |
| 3 | CA6.CG01.IBXCIC |  |  |  |  |  |  |  |  |  |
| 4 | CA6.CG01.ICXDID | NNNN | NNNNNNNNN | NNNNNNNNN | NNNNNNNNN | NNNNNNNNN | NNNNNNNNN | NNNNNNNNN | NNNNNNNNN | NNNNNNN |
| 5 | CA6.CG01.IDXEIE |  |  |  |  |  |  |  |  |  |
| 6 | CA6.CG01.IEXFIF | tatg | aagtaggaat | gggagaggaa | agaaatagat | gggaactcag | tcatttggga | atgattcata | tggaatgttt | ttactgctt |
| 7 | CA6.CG01.IFXGIG | caga | ctgatgtgta | tacgtaggaa | ttttttcctt | tgtgttcctg | tcaccaadctg | aagtggctaa | agagctttgr | gatatactgg ttcaca |
| 8 | CA6.CG01.IGXHIH |  |  |  |  |  |  |  |  |  |
| 9 | CA6.CG01.IHXI |  |  |  |  |  |  |  |  |  |

|   |   | 590 | 600 | 610 | 620 | 630 | 640 | 650 | 660 | 670 |
|---|---|---|---|---|---|---|---|---|---|---|
| 1 | CA6.CG01.XAIA | tcca | agctaatcc | agtttatata | tttgcataa | tttcctaact | gcgaatatca | tttatttana | acaatttatt | ctccag |
| 2 | CA6.CG01.IAXBIB | tttg | acttgggant | aaaangttga | aaaggtaaaa | ggaagga | | | | |
| 3 | CA6.CG01.IBXCIC |  |  |  |  |  |  |  |  |  |
| 4 | CA6.CG01.ICXDID | NNNN | Ntcctccctc | cccaccctca | gtcnctggaa | aacaggtttt | aaagatagtt | gctaatcctt | atttcttcta | aattttta |
| 5 | CA6.CG01.IDXEIE |  |  |  |  |  |  |  |  |  |
| 6 | CA6.CG01.IEXFIF |  |  |  |  |  |  |  |  |  |
| 7 | CA6.CG01.IFXGIG | tcct | accccttgc | acttgtggca | acagataagt | ttgcagttgg | ctaagagagg | tttcgaaaag | gttt | |
| 8 | CA6.CG01.IGXHIH |  |  |  |  |  |  |  |  |  |
| 9 | CA6.CG01.IHXI |  |  |  |  |  |  |  |  |  |

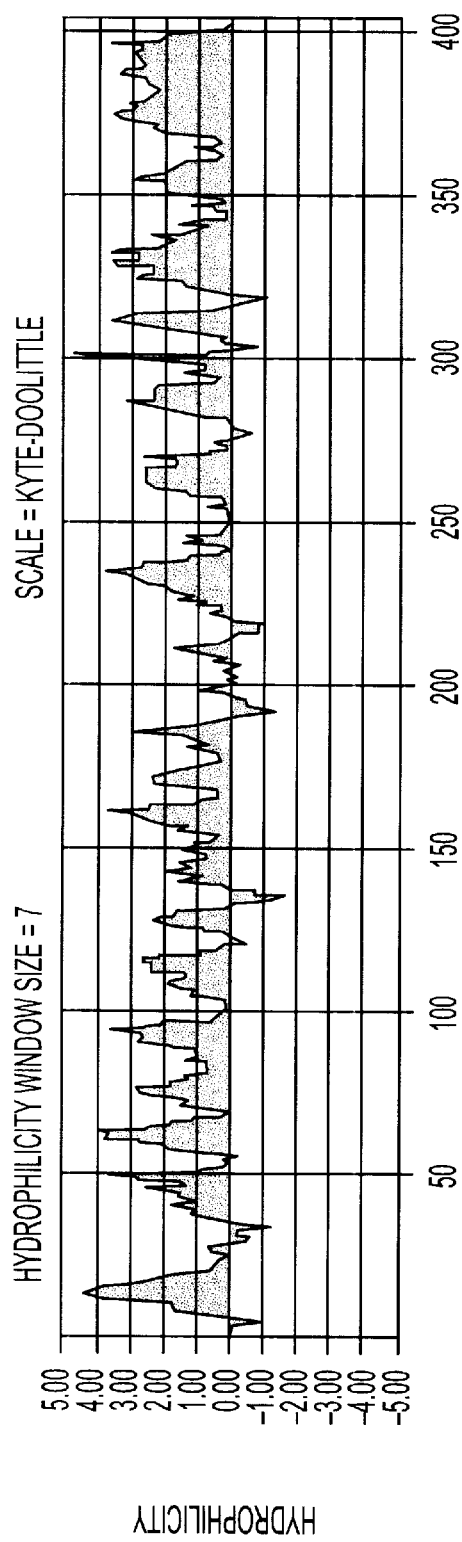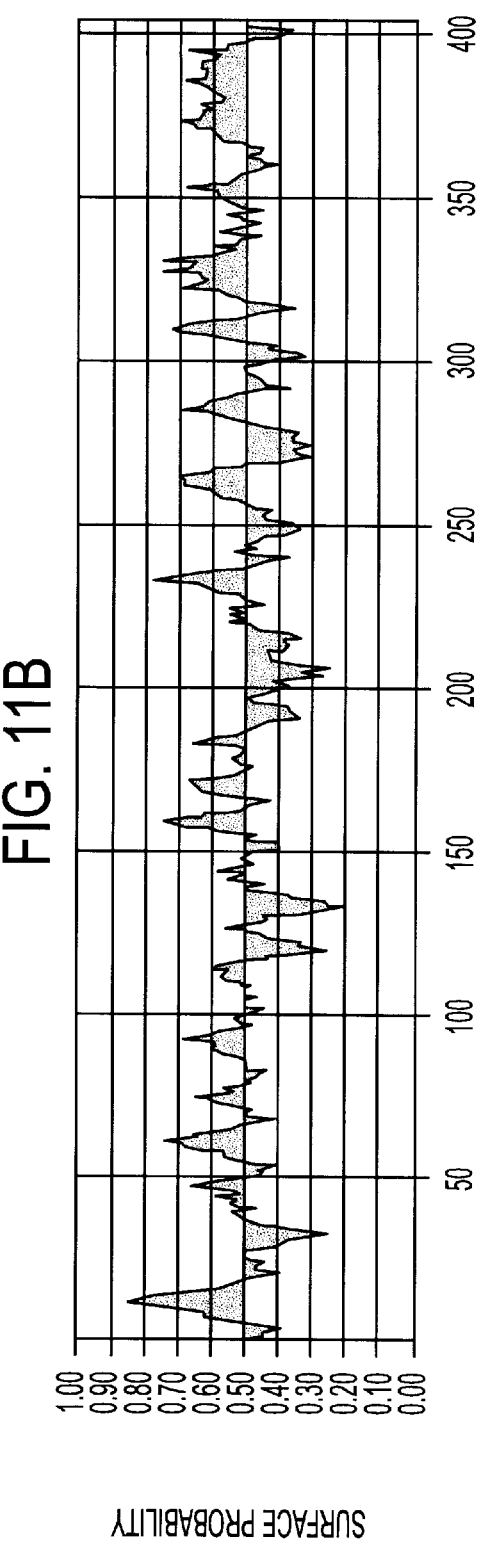

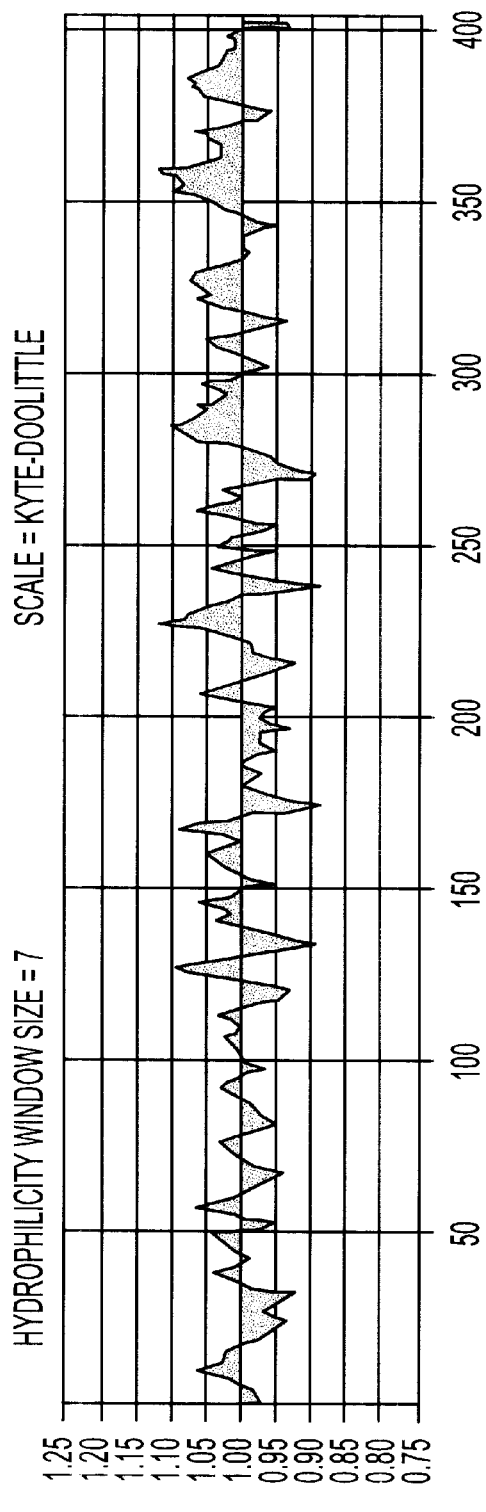
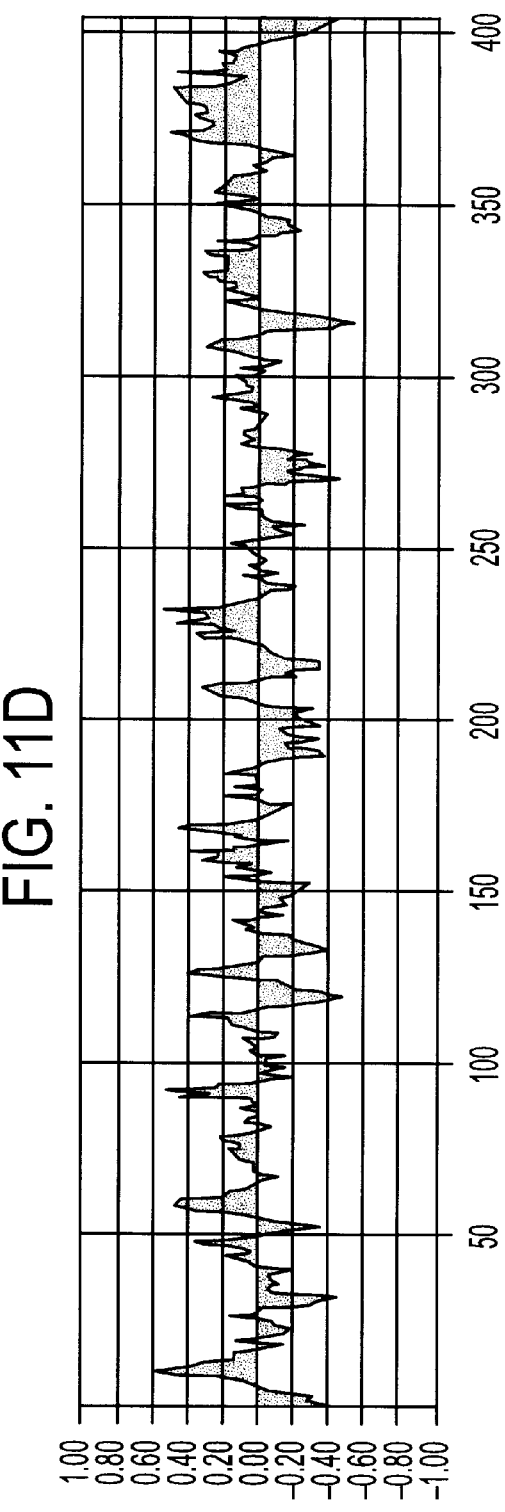

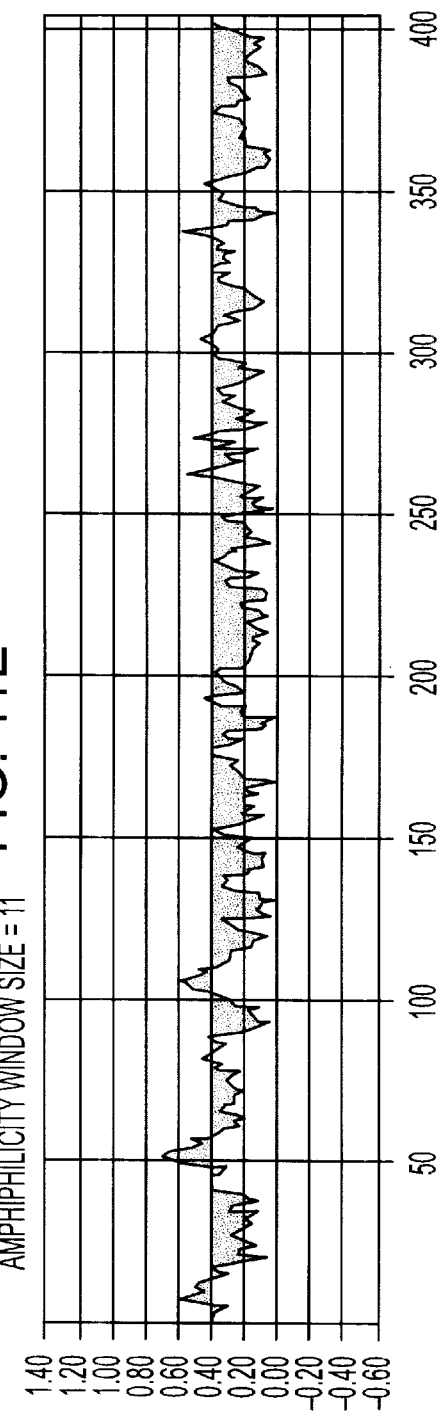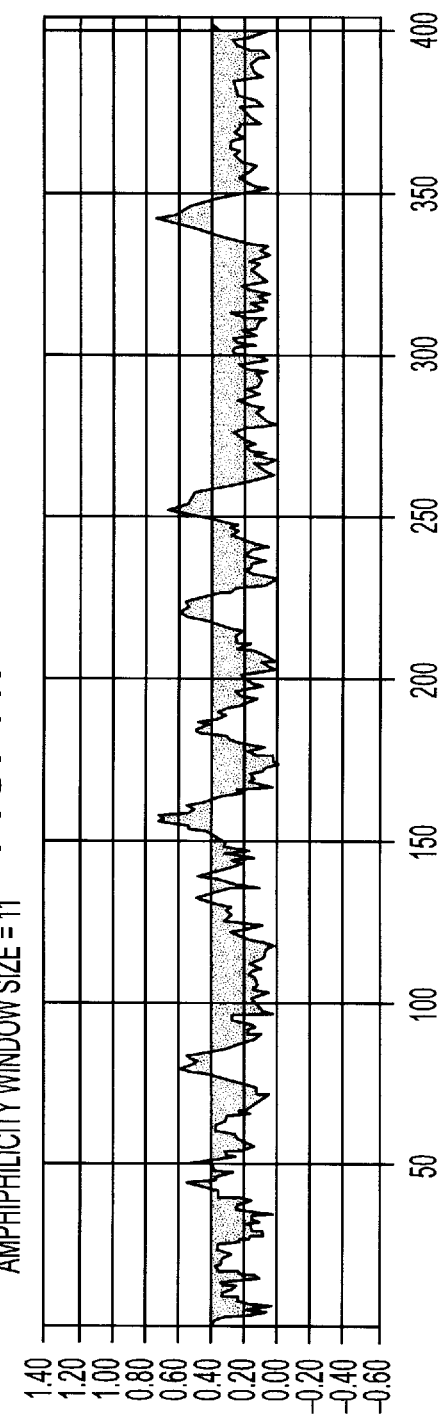

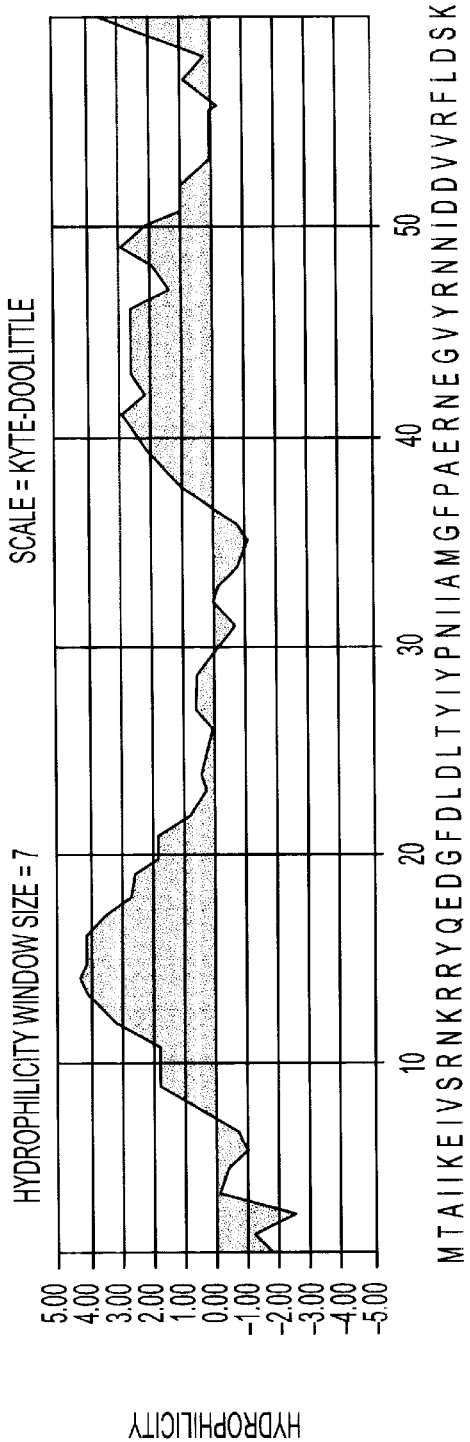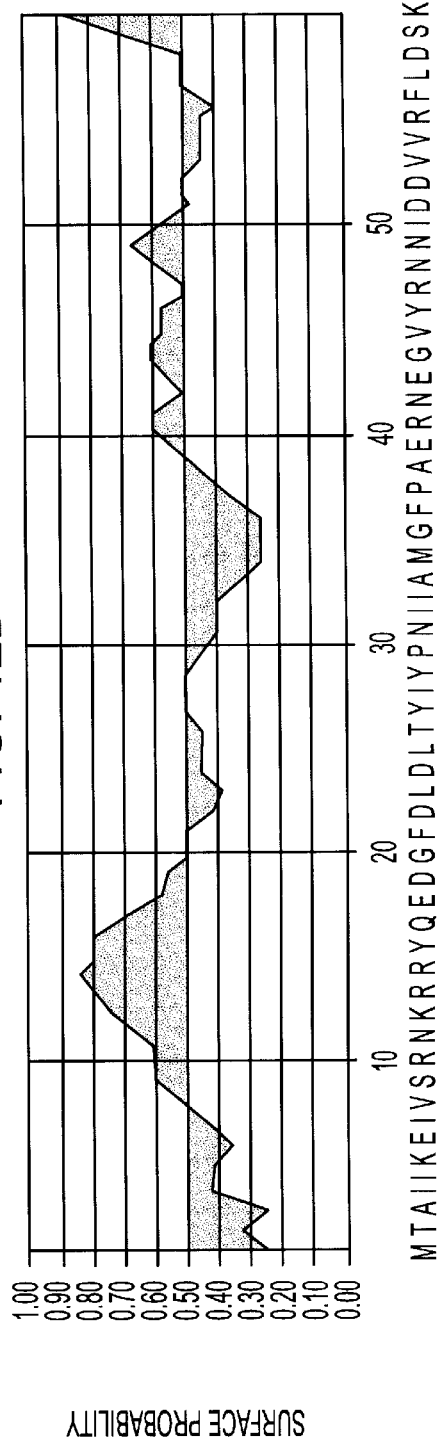

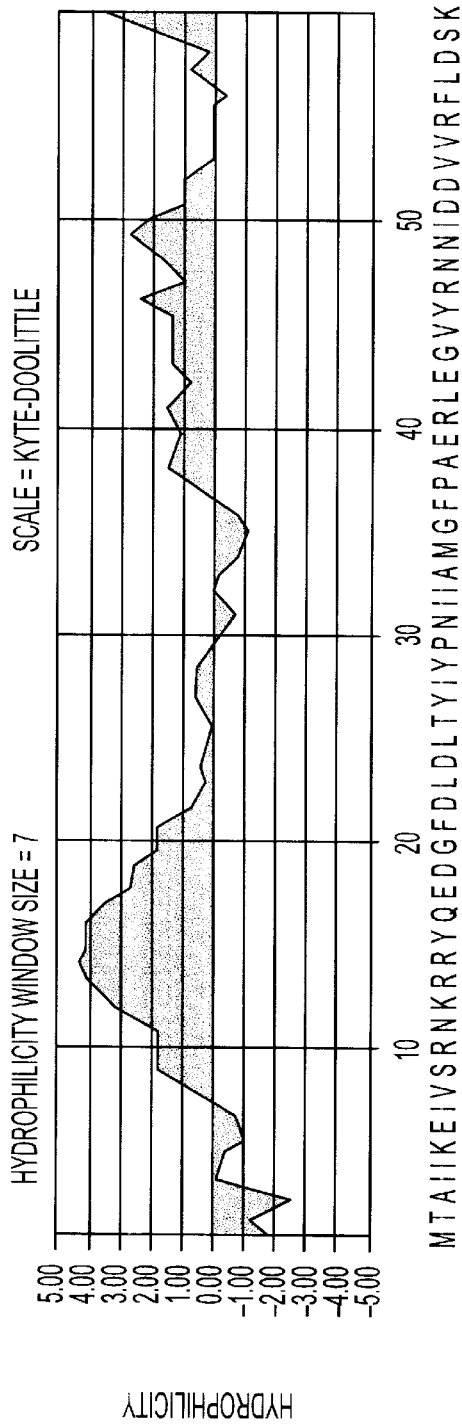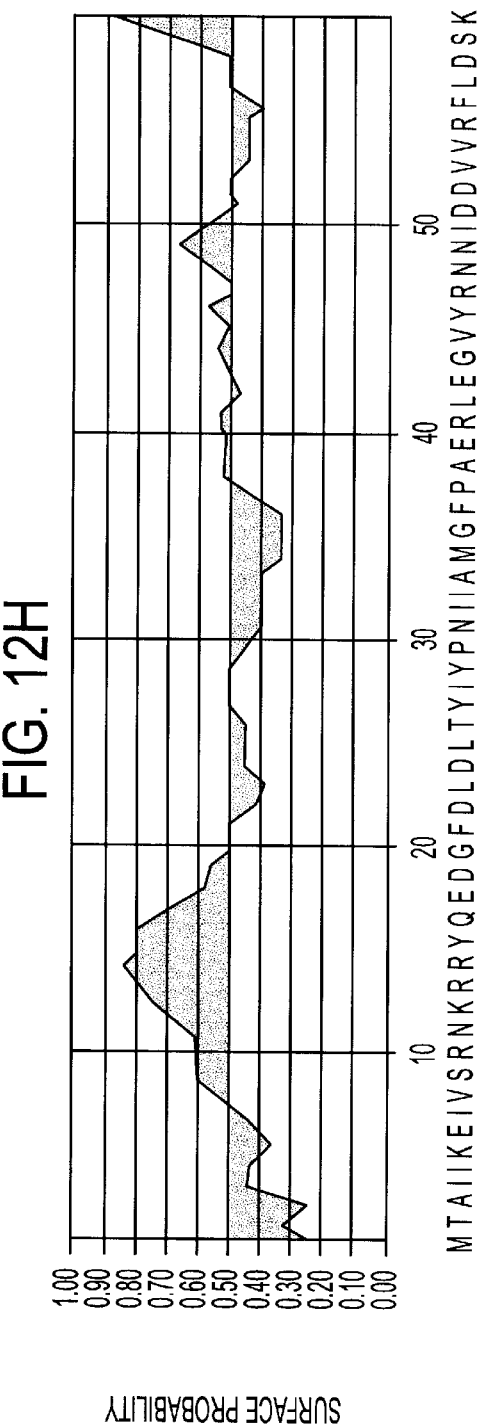

SEQUENCE LISTING (1) GENERAL INFORMATION:

(iii) NUMBER OF SEQUENCES: 27

-continued (2) INFORMATION FOR SEQ ID NO: 1:

(i) SEQUENCE CHARACTERISTICS:
        (A) LENGTH: 403 amino acids
        (B) TYPE: amino acid
        (C) STRANDEDNESS:
        (D) TOPOLOGY: linear (xi) SEQUENCE DESCRIPTION: SEQ ID NO: 1:

```
Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
 50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
                100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
                180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Ser Thr Ser Val Thr Pro Asp
            355                 360                 365
```

-continued

```
Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val
```

(2) INFORMATION FOR SEQ ID NO: 2:

(i) SEQUENCE CHARACTERISTICS:
        (A) LENGTH: 3160 base pairs
        (B) TYPE: nucleic acid
        (C) STRANDEDNESS: single
        (D) TOPOLOGY: linear (xi) SEQUENCE DESCRIPTION: SEQ ID NO: 2:

```
CCTCCCCTCG CCCGGCGCGG TCCCGTCCGC CTCTCGCTCG CCTCCCGCCT CCCCTCGGTC      60

TTCCGAGGCG CCCGGGCTCC CGGCGCGGCG GCGGAGGGGG CGGGCAGGCC GGCGGGCGGT     120

GATGTGGCAG GACTCTTTAT GCGCTGCGGC AGGATACGCG CTCGGCGCTG GGACGCGACT     180

GCGCTCAGTT CTCTCCTCTC GGAAGCTGCA GCCATGATGG AAGTTTGAGA GTTGAGCCGC     240

TGTGAGGCGA GGCCGGGCTC AGGCGAGGGA GATGAGAGAC GGCGGCGGCC GCGGCCCGGA     300

GCCCCTCTCA GCGCCTGTGA GCAGCCGCGG GGGCAGCGCC CTCGGGGAGC CGGCCGGCCT     360

GCGGCGGCGG CAGCGGCGGC GTTTCTCGCC TCCTCTTCGT CTTTTCTAAC CGTGCAGCCT     420

CTTCCTCGGC TTCTCCTGAA AGGGAAGGTG GAAGCCGTGG GCTCGGGCGG GAGCCGGCTG     480

AGGCGCGGCG GCGGCGGCGG CGGCACCTCC CGCTCCTGGA GCGGGGGGGA GAAGCGGCGG     540

CGGCGGCGGC CGCGGCGGCT GCAGCTCCAG GGAGGGGGTC TGAGTCGCCT GTCACCATTT     600

CCAGGGCTGG GAACGCCGGA GAGTTGGTCT CTCCCCTTCT ACTGCCTCCA ACACGGCGGC     660

GGCGGCGGCG GCACATCCAG GGACCCGGGC CGGTTTTAAA CCTCCCGTCC GCCGCCGCCG     720

CACCCCCCGT GGCCCGGGCT CCGGAGGCCG CCGGCGGAGG CAGCCGTTCG GAGGATTATT     780

CGTCTTCTCC CCATTCCGCT GCCGCCGCTG CCAGGCCTCT GGCTGCTGAG GAGAAGCAGG     840

CCCAGTCGCT GCAACCATCC AGCAGCCGCC GCAGCAGCCA TTACCCGGCT GCGGTCCAGA     900

GCCAAGCGGC GGCAGAGCGA GGGGCATCAG CTACCGCCAA GTCCAGAGCC ATTTCCATCC     960

TGCAGAAGAA GCCCCGCCAC CAGCAGCTTC TGCCATCTCT CTCCTCCTTT TTCTTCAGCC    1020

ACAGGCTCCC AGACATGACA GCCATCATCA AAGAGATCGT TAGCAGAAAC AAAAGGAGAT    1080

ATCAAGAGGA TGGATTCGAC TTAGACTTGA CCTATATTTA TCCAAACATT ATTGCTATGG    1140

GATTTCCTGC AGAAAGACTT GAAGGCGTAT ACAGGAACAA TATTGATGAT GTAGTAAGGT    1200

TTTTGGATTC AAAGCATAAA AACCATTACA AGATATACAA TCTTTGTGCT GAAAGACATT    1260

ATGACACCGC CAAATTTAAT TGCAGAGTTG CACAATATCC TTTTGAAGAC CATAACCCAC    1320

CACAGCTAGA ACTTATCAAA CCCTTTTGTG AAGATCTTGA CCAATGGCTA AGTGAAGATG    1380

ACAATCATGT TGCAGCAATT CACTGTAAAG CTGGAAAGGG ACGAACTGGT GTAATGATAT    1440

GTGCATATTT ATTACATCGG GGCAAATTTT TAAAGGCACA GAGGCCCTA GATTTCTATG    1500

GGGAAGTAAG GACCAGAGAC AAAAAGGGAG TAACTATTCC CAGTCAGAGG CGCTATGTGT    1560

ATTATTATAG CTACCTGTTA AAGAATCATC TGGATTATAG ACCAGTGGCA CTGTTGTTTC    1620

ACAAGATGAT GTTTGAAACT ATTCCAATGT TCAGTGGCGG AACTTGCAAT CCTCAGTTTG    1680

TGGTCTGCCA GCTAAAGGTG AAGATATATT CCTCCAATTC AGGACCCACA CGACGGGAAG    1740

ACAAGTTCAT GTACTTTGAG TTCCCTCAGC CGTTACCTGT GTGTGGTGAT ATCAAAGTAG    1800
```

-continued

```
AGTTCTTCCA CAAACAGAAC AAGATGCTAA AAAAGGACAA AATGTTTCAC TTTTGGGTAA      1860

ATACATTCTT CATACCAGGA CCAGAGGAAA CCTCAGAAAA AGTAGAAAAT GGAAGTCTAT      1920

GTGATCAAGA AATCGATAGC ATTTGCAGTA TAGAGCGTGC AGATAATGAC AAGGAATATC      1980

TAGTACTTAC TTTAACAAAA AATGATCTTG ACAAAGCAAA TAAAGACAAA GCCAACCGAT      2040

ACTTTTCTCC AAATTTTAAG GTGAAGCTGT ACTTCACAAA AACAGTAGAG GAGCCGTCAA      2100

ATCCAGAGGC TAGCAGTTCA ACTTCTGTAA CACCAGATGT TAGTGACAAT GAACCTGATC      2160

ATTATAGATA TTCTGACACC ACTGACTCTG ATCCAGAGAA TGAACCTTTT GATGAAGATC      2220

AGCATACACA AATTACAAAA GTCTGAATTT TTTTTTATCA AGAGGGATAA AACACCATGA      2280

AAATAAACTT GAATAAACTG AAAATGGACC TTTTTTTTTT TAATGGCAAT AGGACATTGT      2340

GTCAGATTAC CAGTTATAGG AACAATTCTC TTTTCCTGAC CAATCTTGTT TTACCCTATA      2400

CATCCACAGG GTTTTGACAC TTGTTGTCCA GTTGAAAAAA GGTTGTGTAG CTGTGTCATG      2460

TATATACCTT TTTGTGTCAA AAGGACATTT AAAATTCAAT TAGGATTAAT AAAGATGGCA      2520

CTTTCCCGTT TTATTCCAGT TTTATAAAAA GTGGAGACAG ACTGATGTGT ATACGTAGGA      2580

ATTTTTTCCT TTTGTGTTCT GTCACCAACT GAAGTGGCTA AAGAGCTTTG TGATATACTG      2640

GTTCACATCC TACCCCTTTG CACTTGTGGC AACAGATAAG TTTGCAGTTG CTAAGAGAG      2700

GTTTCCGAAA GGTTTTGCTA CCATTCTAAT GCATGTATTC GGGTTAGGGC AATGGAGGGG      2760

AATGCTCAGA AAGGAAATAA TTTTATGCTG ACTCTGGAC CATATACCAT CTCCAGCTAT      2820

TTACACACAC CTTTCTTTAG CATGCTACAG TTATTAATCT GGACATTCGA GGAATTGGCC      2880

GCTGTCACTG CTTGTTGTTT GCGCATTTTT TTTTAAAGCA TATTGGTGCT AGAAAAGGCA      2940

GCTAAAGGAA GTGAATCTGT ATTGGGGTAC AGGAATGAAC CTTCTGCAAC ATCTTAAGAT      3000

CCACAAATGA AGGGATATAA AAATAATGTC ATAGGTAAGA AACACAGCAA CAATGACTTA      3060

ACCATATAAA TGTGGAGGCT ATCAACAAAG AATGGGCTTG AAACATTATA AAAATTGACA      3120

ATGATTTATT AAATATGTTT TCTCAATTGT AAAAAAAAA                              3160
```

(2) INFORMATION FOR SEQ ID NO: 3:

(i) SEQUENCE CHARACTERISTICS:
        (A) LENGTH: 1962 base pairs
        (B) TYPE: nucleic acid
        (C) STRANDEDNESS: single
        (D) TOPOLOGY: linear (xi) SEQUENCE DESCRIPTION: SEQ ID NO: 3:

```
GCGAGGGAGA TGAGAGACGG CGGCGGCCAC GGCCCAGAGC CCCTCTCAGC GCCTGTGAGC        60

AGCCGCGGGG GCAGCGCCCT CGGGGAGCCG GCCGGGCGGC GGCGGCGGCA GCGGCGGCGG       120

GCCTCGCCTC CTCGTCGTCT GTTCTAACCG GGCAGCTTCT GAGCAGCTTC GGAGAGAGAC       180

GGTGGAAGAA GCCGTGGGCT CGAGCGGGAG CCGGCGCAGG CTCGGCGGCT GCACCTCCCG       240

CTCCTGGAGC GGGGGGGAGA AGCGGCGGCG GCGGCCGCGG CTCCGGGGAG GGGTCGGAG        300

TCGCCTGTCA CCATTGCCAG GGCTGGGAAC GCCGAGAGT TGCTCTCTCC CCTTCTCCTG        360

CCTCCAACAC GGCGGCGGCG GCGGCGGCAC GTCCAGGGAC CCGGGCCGGT GTTAAGCCTC       420

CCGTCCGCCG CCGCCGCACC CCCCCTGGCC CGGGCTCCGG AGGCCGCCGG AGGAGGCAGC       480

CGCTGCGAGG ATTATCCGTC TTCTCCCCAT TCCGCTGCCT CGGCTGCCAG GCCTCTGGCT       540

GCTGAGGAGA AGCAGGCCCA GTCTCTGCAA CCATCCAGCA GCCGCCGCAG CAGCCATTAC       600

CCGGCTGCGG TCCAGGGCCA AGCGGCAGCA GAGCGAGGGG CATCAGCGAC CGCCAAGTCC       660
```

| | |
|---|---|
| AGAGCCATTT CCATCCTGCA GAAGAAGCCT CGCCACCAGC AGCTTCTGCC ATCTCTCTCC | 720 |
| TCCTTTTTCT TCAGCCACAG GCTCCCAGAC ATGACAGCCA TCATCAAAGA GATCGTTAGC | 780 |
| AGAAACAAAA GGAGATATCA AGAGGATGGA TTCGACTTAG ACTTGACCTA TATTTATCCA | 840 |
| AATATTATTG CTATGGGATT TCCTGCAGAA AGACTTGAAG GTGTATACAG GAACAATATT | 900 |
| GATGATGTAG TAAGGTTTTT GGATTCAAAG CATAAAAACC ATTACAAGAT ATACAATCTA | 960 |
| TGTGCTGAGA GACATTATGA CACCGCCAAA TTTAACTGCA GAGTTGCACA GTATCCTTTT | 1020 |
| GAAGACCATA ACCCACCACA GCTAGAACTT ATCAAACCCT TCTGTGAAGA TCTTGACCAA | 1080 |
| TGGCTAAGTG AAGATGACAA TCATGTTGCA GCAATTCACT GTAAAGCTGG AAAGGGACGG | 1140 |
| ACTGGTGTAA TGATTTGTGC ATATTTATTG CATCGGGGCA AATTTTTAAA GGCACAAGAG | 1200 |
| GCCCTAGATT TTTATGGGGA AGTAAGGACC AGAGACAAAA AGGGAGTCAC AATTCCCAGT | 1260 |
| CAGAGGCGCT ATGTATATTA TTATAGCTAC CTGCTAAAAA ATCACCTGGA TTACAGACCC | 1320 |
| GTGGCACTGC TGTTTCACAA GATGATGTTT GAAACTATTC CAATGTTCAG TGGCGGAACT | 1380 |
| TGCAATCCTC AGTTTGTGGT CTGCCAGCTA AAGGTGAAGA TATATTCCTC CAATTCAGGA | 1440 |
| CCCACGCGGC GGGAGGACAA GTTCATGTAC TTTGAGTTCC CTCAGCCATT GCCTGTGTGT | 1500 |
| GGTGATATCA AAGTAGAGTT CTTCCACAAA CAGAACAAGA TGCTCAAAAA GGACAAAATG | 1560 |
| TTTCACTTTT GGGTAAATAC GTTCTTCATA CCAGGACCAG AGGAAACCTC AGAAAAAGTG | 1620 |
| GAAAATGGAA GTCTTTGTGA TCAGGAAATC GATAGCATTT GCAGTATAGA GCGTGCAGAT | 1680 |
| AATGACAAGG AGTATCTTGT ACTCACCCTA ACAAAAAACG ATCTTGACAA AGCAAACAAA | 1740 |
| GACAAGGCCA ACCGATACTT CTCTCCAAAT TTTAAGGTGA AACTATACTT TACAAAAACA | 1800 |
| GTAGAGGAGC CATCAAATCC AGAGGCTAGC AGTTCAACTT CTGTGACTCC AGATGTTAGT | 1860 |
| GACAATGAAC CTGATCATTA TAGATATTCT GACACCACTG ACTCTGATCC AGAGAATGAA | 1920 |
| CCTTTTGATG AAGATCAGCA TTCACAAATT ACAAAAGTCT GA | 1962 |

(2) INFORMATION FOR SEQ ID NO: 4:

(i) SEQUENCE CHARACTERISTICS:
    (A) LENGTH: 1291 base pairs
    (B) TYPE: nucleic acid
    (C) STRANDEDNESS: single
    (D) TOPOLOGY: linear (xi) SEQUENCE DESCRIPTION: SEQ ID NO: 4:

| | |
|---|---|
| CCGCCCGCCG CCAGGCCCGG GGCCGCCTGC AGCCTGCGGA GGAGGCCGCG CCGCCCGCCG | 60 |
| CTCCTGCCGT CTCTCTCCTC CTTCCTCTCC AGCCACCGGC TCCCAGACAT GACAGCCATC | 120 |
| ATCAAGGAGA TCGTCAGCAG AAACAAAAGG CGCTACCAGG AGGATGGGTT CGACTTGGAC | 180 |
| TTGACCTATA TTTATCCCAA CATTATTGCT ATGGGGTTTC CTGCAGAAAG ACTTGAAGGC | 240 |
| GTATACAGGA ACAATATTGA TGATGTAGTA AGGTTTTTGG ATTCAAAGCA TAAAAACCAT | 300 |
| TACAAGATAT ACAATCTGTG TGCTGAAAGA CATTATGATA CCGCCAAATT TAACTGCAGA | 360 |
| GTTGCACAGT ATCCTTTTGA AGACCATAAT CCACCACAGC TAGAACTTAT CAAACCCTTT | 420 |
| TGTGAAGATC TTGACCAATG GCTAAGTGAA GATGACAATC ATGTTGCAGC AATTCACTGT | 480 |
| AAAGCTGGAA AGGGACGAAC TGGTGTAATG ATTTGTGCAT ATTTATTACA TCGGGGCAAA | 540 |
| TTTCTAAAGG CACAAGAGGC CCTAGATTTC TATGGGGAAG TAAGGACCAG AGACAAAAAG | 600 |
| GGAGTAACTA TTCCCAGTCA GAGGCGCTAT GTGTATTATT ATAGCTACCT GTTAAAGAAT | 660 |
| CATCTGGATT ATAGACCAGT GGCACTGTTG TTTCACAAGA TGATGTTTGA AACTATTCCA | 720 |

```
ATGTTCAGTG GCGGAACTTG CAATCCTCAG TTTGTGGTCT GCCAGCTAAA GGTGAAGATC    780

TATTCCTCCA ATTCAGGACC CACACGACGG GAAGACAAGT TCATGTACTT TGAGTTCCCT    840

CAGCCATTGC CTGTGTGCGG TGACATCAAA GTAGAGTTCT TCCACAAACA GAACAAGATG    900

CTAAAAAAGG ACAAAATGTT TCACTTTTGG GTAAACACAT TCTTCATACC AGGACCAGAG    960

GAAACCTCAG AAAAGTAGA AAATGGAAGT CTATGTGATC AAGAAATTGA TAGTATTTGC    1020

AGTATAGAAC GTGCAGATAA TGACAAGGAA TATCTAGTAC TCACTTTAAC AAAAAATGAT    1080

CTCGACAAAG CAAATAAAGA CAAGGCCAAC CGATATTTTT CTCCAAATTT TAAGGTGAAG    1140

CTGTACTTCA CAAAAACTGT AGAGGAGCCA TCAAACCCGG AGGCTAGCAG TTCAACTTCT    1200

GTGACGCCAG ATGTTAGTGA CAATGAACCT GATCATTATA GATATTCTGA CACCACTGAC    1260

TCTGACCCAG AGAATGAACC CTTTGATGAA G                                   1291
```

(2) INFORMATION FOR SEQ ID NO: 5:

(i) SEQUENCE CHARACTERISTICS:
        (A) LENGTH: 742 amino acids
        (B) TYPE: amino acid
        (C) STRANDEDNESS:
        (D) TOPOLOGY: linear (xi) SEQUENCE DESCRIPTION: SEQ ID NO: 5:

```
Ser Pro Arg Pro Ala Arg Ser Arg Pro Pro Leu Ala Arg Leu Pro Pro
 1               5                  10                  15

Pro Leu Gly Leu Pro Arg Arg Pro Gly Ser Arg Gly Gly Gly
            20                  25                  30

Gly Gly Gln Ala Gly Gly Arg Cys Gly Arg Thr Leu Tyr Ala Leu Arg
            35                  40                  45

Gln Asp Thr Arg Ser Ala Leu Gly Arg Asp Cys Ala Gln Phe Ser Pro
         50                  55                  60

Leu Gly Ser Cys Ser His Asp Gly Ser Leu Arg Val Glu Pro Leu Gly
65                  70                  75                  80

Glu Ala Gly Leu Arg Arg Gly Arg Glu Thr Ala Ala Ala Ala Arg
                85                  90                  95

Ser Pro Ser Gln Arg Leu Ala Ala Ala Gly Ala Ala Pro Ser Gly Ser
                100                 105                 110

Arg Pro Ala Cys Gly Gly Gly Ser Gly Gly Val Ser Arg Leu Leu Phe
            115                 120                 125

Val Phe Ser Asn Arg Ala Ala Ser Ser Ser Ala Ser Pro Glu Arg Glu
        130                 135                 140

Gly Ser Arg Gly Leu Gly Arg Glu Pro Ala Glu Ala Arg Arg Arg
145                 150                 155                 160

Arg Arg His Leu Pro Leu Leu Glu Arg Gly Glu Ala Ala Ala
                165                 170                 175

Ala Ala Ala Ala Ala Ala Pro Gly Arg Gly Ser Glu Ser Pro Val
                180                 185                 190

Thr Ile Ser Arg Ala Gly Asn Ala Gly Glu Leu Val Ser Pro Leu Leu
            195                 200                 205

Leu Pro Pro Thr Arg Arg Arg Arg Arg His Ile Gln Gly Pro Gly
        210                 215                 220

Pro Val Leu Asn Leu Pro Ser Ala Ala Ala Pro Pro Val Ala Arg
225                 230                 235                 240

Ala Pro Glu Ala Ala Gly Gly Gly Ser Arg Ser Glu Asp Tyr Ser Ser
                245                 250                 255
```

-continued

Ser Pro His Ser Ala Ala Ala Ala Arg Pro Leu Ala Ala Glu Glu
            260                 265             270

Lys Gln Ala Gln Ser Leu Gln Pro Ser Ser Arg Arg Ser Ser His
        275                 280             285

Tyr Pro Ala Ala Val Gln Ser Gln Ala Ala Glu Arg Gly Ala Ser
    290                 295             300

Ala Thr Ala Lys Ser Arg Ala Ile Ser Ile Leu Gln Lys Lys Pro Arg
305                 310             315                 320

His Gln Gln Leu Leu Pro Ser Leu Ser Ser Phe Phe Ser His Arg
                325                 330             335

Leu Pro Asp Met Thr Ala Ile Ile Lys Glu Ile Val Ser Arg Asn Lys
            340             345             350

Arg Arg Tyr Gln Glu Asp Gly Phe Asp Leu Asp Leu Thr Tyr Ile Tyr
        355                 360             365

Pro Asn Ile Ile Ala Met Gly Phe Pro Ala Glu Arg Leu Glu Gly Val
    370                 375             380

Tyr Arg Asn Asn Ile Asp Asp Val Val Arg Phe Leu Asp Ser Lys His
385                 390             395                 400

Lys Asn His Tyr Lys Ile Tyr Asn Leu Cys Ala Glu Arg His Tyr Asp
                405             410             415

Thr Ala Lys Phe Asn Cys Arg Val Ala Gln Tyr Pro Phe Glu Asp His
            420             425             430

Asn Pro Pro Gln Leu Glu Leu Ile Lys Pro Phe Cys Glu Asp Leu Asp
        435             440             445

Gln Trp Leu Ser Glu Asp Asp Asn His Val Ala Ala Ile His Cys Lys
    450             455             460

Ala Gly Lys Gly Arg Thr Gly Val Met Ile Cys Ala Tyr Leu Leu His
465             470             475             480

Arg Gly Lys Phe Leu Lys Ala Gln Glu Ala Leu Asp Phe Tyr Gly Glu
            485             490             495

Val Arg Thr Arg Asp Lys Lys Gly Val Thr Ile Pro Ser Gln Arg Arg
        500             505             510

Tyr Val Tyr Tyr Tyr Ser Tyr Leu Leu Lys Asn His Leu Asp Tyr Arg
    515             520             525

Pro Val Ala Leu Leu Phe His Lys Met Met Phe Glu Thr Ile Pro Met
    530             535             540

Phe Ser Gly Gly Thr Cys Asn Pro Gln Phe Val Val Cys Gln Leu Lys
545             550             555             560

Val Lys Ile Tyr Ser Ser Asn Ser Gly Pro Thr Arg Arg Glu Asp Lys
            565             570             575

Phe Met Tyr Phe Glu Phe Pro Gln Pro Leu Pro Val Cys Gly Asp Ile
        580             585             590

Lys Val Glu Phe His Lys Gln Asn Lys Met Leu Lys Lys Asp Lys
    595             600             605

Met Phe His Phe Trp Val Asn Thr Phe Phe Ile Pro Gly Pro Glu Glu
    610             615             620

Thr Ser Glu Lys Val Glu Asn Gly Ser Leu Cys Asp Gln Glu Ile Asp
625             630             635             640

Ser Ile Cys Ser Ile Glu Arg Ala Asp Asn Asp Lys Glu Tyr Leu Val
            645             650             655

Leu Thr Leu Thr Lys Asn Asp Leu Asp Lys Ala Asn Lys Asp Lys Ala
        660             665             670

Asn Arg Tyr Phe Ser Pro Asn Phe Lys Val Lys Leu Tyr Phe Thr Lys

```
              675                 680                 685
Thr Val Glu Glu Pro Ser Asn Pro Glu Ala Ser Ser Ser Thr Ser Val
            690                 695                 700

Thr Pro Asp Val Ser Asp Asn Glu Pro Asp His Tyr Arg Tyr Ser Asp
705                 710                 715                 720

Thr Thr Asp Ser Asp Pro Glu Asn Glu Pro Phe Asp Glu Asp Gln His
                725                 730                 735

Thr Gln Ile Thr Lys Val
            740
```

(2) INFORMATION FOR SEQ ID NO: 6:

(i) SEQUENCE CHARACTERISTICS:
        (A) LENGTH: 645 amino acids
        (B) TYPE: amino acid
        (C) STRANDEDNESS:
        (D) TOPOLOGY: linear (xi) SEQUENCE DESCRIPTION: SEQ ID NO: 6:

```
Arg Glu Thr Ala Ala Ala Thr Ala Gln Ser Pro Ser Gln Arg Leu Ala
1               5                  10                  15

Ala Ala Gly Ala Ala Pro Ser Gly Ser Arg Pro Gly Gly Gly Gly Gly
            20                  25                  30

Ser Gly Gly Gly Pro Arg Leu Leu Val Val Cys Ser Asn Arg Ala Ala
        35                  40                  45

Ser Glu Gln Glu Arg Asp Gly Gly Arg Ser Arg Gly Leu Glu Arg Glu
    50                  55                  60

Pro Ala Gln Ala Arg Arg Leu His Leu Pro Leu Leu Glu Arg Gly Gly
65                  70                  75                  80

Glu Ala Ala Ala Ala Pro Gly Arg Gly Ser Glu Ser Pro Val Thr
                85                  90                  95

Ile Ala Arg Ala Gly Asn Ala Gly Glu Leu Leu Ser Pro Leu Leu Leu
                100                 105                 110

Pro Pro Thr Arg Arg Arg Arg Arg His Val Gln Gly Pro Gly Pro
            115                 120                 125

Val Leu Ser Leu Pro Ser Ala Ala Ala Pro Pro Leu Ala Arg Ala
130                 135                 140

Pro Glu Ala Ala Gly Gly Gly Ser Arg Cys Glu Asp Tyr Pro Ser Ser
145                 150                 155                 160

Pro His Ser Ala Ala Ser Ala Ala Arg Pro Leu Ala Ala Glu Glu Lys
                165                 170                 175

Gln Ala Gln Ser Leu Gln Pro Ser Ser Arg Arg Ser Ser His Tyr
            180                 185                 190

Pro Ala Ala Val Gln Gly Gln Ala Ala Glu Arg Gly Ala Ser Ala
            195                 200                 205

Thr Ala Lys Ser Arg Ala Ile Ser Ile Leu Gln Lys Lys Pro Arg His
            210                 215                 220

Gln Gln Leu Leu Pro Ser Leu Ser Ser Phe Phe Phe Ser His Arg Leu
225                 230                 235                 240

Pro Asp Met Thr Ala Ile Ile Lys Glu Ile Val Ser Arg Asn Lys Arg
                245                 250                 255

Arg Tyr Gln Glu Asp Gly Phe Asp Leu Asp Leu Thr Tyr Ile Tyr Pro
            260                 265                 270

Asn Ile Ile Ala Met Gly Phe Pro Ala Glu Arg Leu Glu Gly Val Tyr
            275                 280                 285
```

-continued

```
Arg Asn Asn Ile Asp Asp Val Val Arg Phe Leu Asp Ser Lys His Lys
290                 295                 300
Asn His Tyr Lys Ile Tyr Asn Leu Cys Ala Glu Arg His Tyr Asp Thr
305                 310                 315                 320
Ala Lys Phe Asn Cys Arg Val Ala Gln Tyr Pro Phe Glu Asp His Asn
                325                 330                 335
Pro Pro Gln Leu Glu Leu Ile Lys Pro Phe Cys Glu Asp Leu Asp Gln
            340                 345                 350
Trp Leu Ser Glu Asp Asp Asn His Val Ala Ala Ile His Cys Lys Ala
        355                 360                 365
Gly Lys Gly Arg Thr Gly Val Met Ile Cys Ala Tyr Leu Leu His Arg
370                 375                 380
Gly Lys Phe Leu Lys Ala Gln Glu Ala Leu Asp Phe Tyr Gly Glu Val
385                 390                 395                 400
Arg Thr Arg Asp Lys Lys Gly Val Thr Ile Pro Ser Gln Arg Arg Tyr
                405                 410                 415
Val Tyr Tyr Tyr Ser Tyr Leu Leu Lys Asn His Leu Asp Tyr Arg Pro
            420                 425                 430
Val Ala Leu Leu Phe His Lys Met Met Phe Glu Thr Ile Pro Met Phe
        435                 440                 445
Ser Gly Gly Thr Cys Asn Pro Gln Phe Val Val Cys Gln Leu Lys Val
450                 455                 460
Lys Ile Tyr Ser Ser Asn Ser Gly Pro Thr Arg Arg Glu Asp Lys Phe
465                 470                 475                 480
Met Tyr Phe Glu Phe Pro Gln Pro Leu Pro Val Cys Gly Asp Ile Lys
                485                 490                 495
Val Glu Phe Phe His Lys Gln Asn Lys Met Leu Lys Lys Asp Lys Met
            500                 505                 510
Phe His Phe Trp Val Asn Thr Phe Phe Ile Pro Gly Pro Glu Glu Thr
        515                 520                 525
Ser Glu Lys Val Glu Asn Gly Ser Leu Cys Asp Gln Glu Ile Asp Ser
530                 535                 540
Ile Cys Ser Ile Glu Arg Ala Asp Asn Asp Lys Glu Tyr Leu Val Leu
545                 550                 555                 560
Thr Leu Thr Lys Asn Asp Leu Asp Lys Ala Asn Lys Asp Lys Ala Asn
                565                 570                 575
Arg Tyr Phe Ser Pro Asn Phe Lys Val Lys Leu Tyr Phe Thr Lys Thr
            580                 585                 590
Val Glu Glu Pro Ser Asn Pro Glu Ala Ser Ser Thr Ser Val Thr
        595                 600                 605
Pro Asp Val Ser Asp Asn Glu Pro Asp His Tyr Arg Tyr Ser Asp Thr
610                 615                 620
Thr Asp Ser Asp Pro Glu Asn Glu Pro Phe Asp Glu Asp Gln His Ser
625                 630                 635                 640
Gln Ile Thr Lys Val
            645
```

(2) INFORMATION FOR SEQ ID NO: 7:

(i) SEQUENCE CHARACTERISTICS:
        (A) LENGTH: 430 amino acids
        (B) TYPE: amino acid
        (C) STRANDEDNESS:
        (D) TOPOLOGY: linear (xi) SEQUENCE DESCRIPTION: SEQ ID NO: 7:

-continued

```
Pro Pro Ala Ala Arg Pro Gly Ala Ala Cys Ser Leu Arg Arg Arg Pro
1               5                   10                  15

Arg Arg Pro Pro Leu Leu Pro Ser Leu Ser Ser Phe Leu Ser Ser His
            20                  25                  30

Arg Leu Pro Asp Met Thr Ala Ile Ile Lys Glu Ile Val Ser Arg Asn
            35                  40                  45

Lys Arg Arg Tyr Gln Glu Asp Gly Phe Asp Leu Asp Leu Thr Tyr Ile
        50                  55                  60

Tyr Pro Asn Ile Ile Ala Met Gly Phe Pro Ala Glu Arg Leu Glu Gly
65                  70                  75                  80

Val Tyr Arg Asn Asn Ile Asp Asp Val Val Arg Phe Leu Asp Ser Lys
                85                  90                  95

His Lys Asn His Tyr Lys Ile Tyr Asn Leu Cys Ala Glu Arg His Tyr
                100                 105                 110

Asp Thr Ala Lys Phe Asn Cys Arg Val Ala Gln Tyr Pro Phe Glu Asp
            115                 120                 125

His Asn Pro Pro Gln Leu Glu Leu Ile Lys Pro Phe Cys Glu Asp Leu
            130                 135                 140

Asp Gln Trp Leu Ser Glu Asp Asp Asn His Val Ala Ala Ile His Cys
145                 150                 155                 160

Lys Ala Gly Lys Gly Arg Thr Gly Val Met Ile Cys Ala Tyr Leu Leu
                165                 170                 175

His Arg Gly Lys Phe Leu Lys Ala Gln Glu Ala Leu Asp Phe Tyr Gly
                180                 185                 190

Glu Val Arg Thr Arg Asp Lys Lys Gly Val Thr Ile Pro Ser Gln Arg
            195                 200                 205

Arg Tyr Val Tyr Tyr Ser Tyr Leu Leu Lys Asn His Leu Asp Tyr
            210                 215                 220

Arg Pro Val Ala Leu Leu Phe His Lys Met Met Phe Glu Thr Ile Pro
225                 230                 235                 240

Met Phe Ser Gly Gly Thr Cys Asn Pro Gln Phe Val Val Cys Gln Leu
                245                 250                 255

Lys Val Lys Ile Tyr Ser Ser Asn Ser Gly Pro Thr Arg Arg Glu Asp
                260                 265                 270

Lys Phe Met Tyr Phe Glu Phe Pro Gln Pro Leu Pro Val Cys Gly Asp
            275                 280                 285

Ile Lys Val Glu Phe Phe His Lys Gln Asn Lys Met Leu Lys Lys Asp
            290                 295                 300

Lys Met Phe His Phe Trp Val Asn Thr Phe Phe Ile Pro Gly Pro Glu
305                 310                 315                 320

Glu Thr Ser Glu Lys Val Glu Asn Gly Ser Leu Cys Asp Gln Glu Ile
                325                 330                 335

Asp Ser Ile Cys Ser Ile Glu Arg Ala Asp Asn Asp Lys Glu Tyr Leu
                340                 345                 350

Val Leu Thr Leu Thr Lys Asn Asp Leu Asp Lys Ala Asn Lys Asp Lys
                355                 360                 365

Ala Asn Arg Tyr Phe Ser Pro Asn Phe Lys Val Lys Leu Tyr Phe Thr
        370                 375                 380

Lys Thr Val Glu Glu Pro Ser Asn Pro Glu Ala Ser Ser Ser Thr Ser
385                 390                 395                 400

Val Thr Pro Asp Val Ser Asp Asn Glu Pro Asp His Tyr Arg Tyr Ser
                405                 410                 415
```

```
Asp Thr Thr Asp Ser Asp Pro Glu Asn Glu Pro Phe Asp Glu
        420                 425             430
```

(2) INFORMATION FOR SEQ ID NO: 8:

(i) SEQUENCE CHARACTERISTICS:
        (A) LENGTH: 1257 base pairs
        (B) TYPE: nucleic acid
        (C) STRANDEDNESS: single
        (D) TOPOLOGY: linear (xi) SEQUENCE DESCRIPTION: SEQ ID NO: 8:

```
CCTCCCCTCG CCCGGCGCGG TCCCGTCCGC CTCTCGCTCG CCTCCCGCCT CCCCTCGGTC      60

TTCCGAGGCG CCCGGGCTCC CGGCGCGGCG GCGGAGGGGG CGGGCAGGCC GGCGGGCGGT     120

GATGTGGCAG GACTCTTTAT GCGCTGCGGC AGGATACGCG CTCGGCGCTG GGACGCGACT     180

GCGCTCAGTT CTCTCCTCTC GGAAGCTGCA GCCATGATGG AAGTTTGAGA GTTGAGCCGC     240

TGTGAGGCGA GGCCGGGCTC AGGCGAGGGA GATGAGAGAC GGCGGCGGCC GCGGCCCGGA     300

GCCCCTCTCA GCGCCTGTGA GCAGCCGCGG GGGCAGCGCC CTCGGGGAGC CGGCCGGCCT     360

GCGGCGGCGG CAGCGGCGGC GTTTCTCGCC TCCTCTTCGT CTTTTCTAAC CGTGCAGCCT     420

CTTCCTCGGC TTCTCCTGAA AGGGAAGGTG GAAGCCGTGG GCTCGGGCGG GAGCCGGCTG     480

AGGCGCGGCG GCGGCGGCGG CGGCACCTCC CGCTCCTGGA GCGGGGGGA GAAGCGGCGG      540

CGGCGGCGGC CGCGGCGGCT GCAGCTCCAG GGAGGGGGTC TGAGTCGCCT GTCACCATTT     600

CCAGGGCTGG GAACGCCGGA GAGTTGGTCT CTCCCCTTCT ACTGCCTCCA ACACGGCGGC     660

GGCGGCGGCG GCACATCCAG GGACCCGGGC CGGTTTTAAA CCTCCCGTCC GCCGCCGCCG     720

CACCCCCCGT GGCCCGGGCT CCGGAGGCCG CCGGCGGAGG CAGCCGTTCG GAGGATTATT     780

CGTCTTCTCC CCATTCCGCT GCCGCCGCTG CCAGGCCTCT GGCTGCTGAG GAGAAGCAGG     840

CCCAGTCGCT GCAACCATCC AGCAGCCGCC GCAGCAGCCA TTACCCGGCT GCGGTCCAGA     900

GCCAAGCGGC GGCAGAGCGA GGGGCATCAG CTACCGCCAA GTCCAGAGCC ATTTCCATCC     960

TGCAGAAGAA GCCCCGCCAC CAGCAGCTTC TGCCATCTCT CTCCTCCTTT TTCTTCAGCC    1020

ACAGGCTCCC AGACATGACA GCCATCATCA AAGAGATCGT TAGCAGAAAC AAAAGGAGAT    1080

ATCAAGAGGA TGGATTCGAC TTAGACTTGA CCTGTATCCA TTTCTGCGGC TGCTCCTCTT    1140

TACCTTTCTG TCACTCTCTT AGAACGTGGG AGTAGACGGA TGCGAAAATG TCCGTAGTTT    1200

GGGTGACTAT AACATTTAAC CCTGGTCAGG TTGCTAGGTC ATATATTTTG TGTTTCC       1257
```

(2) INFORMATION FOR SEQ ID NO: 9:

(i) SEQUENCE CHARACTERISTICS:
        (A) LENGTH: 1084 base pairs
        (B) TYPE: nucleic acid
        (C) STRANDEDNESS: single
        (D) TOPOLOGY: linear (xi) SEQUENCE DESCRIPTION: SEQ ID NO: 9:

```
GAGACATAGC CAGCTCTTAA ATCTGACTTC CAGATTTTCA CTGTGTCTTC TTTTTTCTGT      60

AACGTGTTGC CTTTTTTAGC CATGAAAAAT TAGAAGTTGA ACTCTTGTCT TTTCAGGCAG     120

GTGTCAATTT TGGGGTTTTG TTTTGATTTT TGGTTTTTGA CATAAAGTAC TTTAGTTCTG     180

TGATGTATAA ACCGTGAGTT TCTGTTTTTC TCATATACCT GAATACTGTC CATGTGGAAG     240

TTACCTTTTA TCTTTACCAG TATTAACACA TAAATGGTTA TACATAAATA CATTGACCAC     300

CTTTTATTAC TCCAGCTATA GTGGGGAAAG CTTTCTTTTC ATAACTAGCT AATGTTTTAA     360
```

```
AAAGTATTCT TTTAGTTTGA TTGCTGCATA TTTCAGATAT TTCTTTCCTT AACTAAAGTA      420

CTCAGATATT TATCCAAACA TTATTGCTAT GGGATTTCCT GCAGAAAGAC TTGAAGGCGT      480

ATACAGGAAC AATATTGATG ATGTAGTAAG GTAAGAATGC TTTGATTTTC TATTTCAAAT      540

ATTGATGTTT ATATTCATGT TGTGTTTTCA TTTAGAAAAG ATTTCTAAGC CACAGAAAAA      600

GATACTTTGT GATGTAAACT ATTATTGTAG TGCTCTATAA TCATTTTTTG GCTTACCGTA      660

CCTAATGGAC TTCAGGGGGA TACAGTTCAT TTGATAAGAA CTGACCTTAT ACATTACATA      720

ATCAGGTACT TATGTGATAT CATTTCCTGG ACTCCATAAA ATGCTGGTCA CCAGGTTTAA      780

TACCTGGATT CCATTACAGT GTGATTTTTG TCTTATTTCA TAGTTGGGGA TTAGGCTTAA      840

AATCCTAGAG TGGATTTATT CAGTTAAATT TATTCACACT AAGATGTGAT GACTAATACT      900

GTATATTTTT ATGTAGACCA AATTTTAAGG TACCACTGTG CATATGTTAC CAACTACCTG      960

AAGAATATTT GGTTGGTACA GAATATATAA AGGAATCGCT GGTGTTCCAA GGCTAATCCA     1020

GTTTTATAAT TTTGCATAAT TTCCTAACTG CGAATATCAT TTATTTAAAC AATTTATTCT     1080

CCAG                                                                  1084

(2) INFORMATION FOR SEQ ID NO: 10:

(i) SEQUENCE CHARACTERISTICS:
        (A) LENGTH: 1104 base pairs
        (B) TYPE: nucleic acid
        (C) STRANDEDNESS: single
        (D) TOPOLOGY: linear (xi) SEQUENCE DESCRIPTION: SEQ ID NO: 10:

GAATTAATAG TTAGTACGTG GATCTTTCAA ATATCAAAAG TTTTCAGTTT GATGGGAAAA       60

TGATGTCTGA ATTTTCAGGG TTATTTTTAA GAGTACTTGA TTATGACTGT CTTGTAAATC      120

TCTATGAGCT AGGTATACTT GCACTAAATG CTAATGCTTT TTAAAGAAGT TATGTCTTAA      180

TATTCAGTCT CATTATGTTA GGTTGAAGAT AGAAGATTAT GAAAATATTC TCTGAAAAGC      240

TCTGGTTTTA CTTCAGATTG TATAAATCTG TGTAATGTAA TAATTATTTA AGAATGACAT      300

GATTACTACT CTAAACCCAT AGAAGGGGTA TTTGTTGGAT TATTTATTTT CACTTAAATG      360

GTATTTGAGA TTAGGAAAAA GAAAATCTGT CTTTTGGTTT TTCTTGATAG TATTAATGTA      420

ATTTCAAATG TTAGCTCATT TTTGTTAATG GTGGCTTTTT GTTTGTTTGT TTTGTTTTAA      480

GGTTTTTGGA TTCAAAGCAT AAAAACCATT ACAAGATATA CAATCTGTAA GTATGTTTTC      540

TTATTTGTAT GCTTGCAAAT ATCTTCTAAA ACAACTATTA AGTGAAAGTT ATCTGCTTGT      600

TAGAGTGAGG TAGAGTTAAA GATACATTTT AACAGAATTG TATTCCTAAA CCGATTAAGT      660

CAAGAAGTCC AAGAGCATTG TTAGATCATT TAGAAAGTGT AGTGATGAGG TAAAACATTG      720

TTGGCACAGA TTCATGTTAC TTGATCTGCT TTAAATGACT TGGCATCTAG CCCATATTTG      780

AGCCCATAAC CGTGTGGTAA TTTGAAGTGT AATTCACAGT AGAGCTTCTG TTAAAGCACT      840

AATAGCATCT TCCATGGAGG TATACTTCAG AGTGAATATA ATTTTGTTTA TCCTGTGTCT      900

CTAGAGCTAT TGACTGAAAA AGCTGTTAGG GCATTCTCTA ACTGTACATC ACCTAAGTTA      960

TTTAAAATTG CTGAATTAAG TGGCTTGTCT TGTCTAGACA GATTTAAGG ACTGCCCACC     1020

TGATTGATAG AACTAGTTGA CCTTATCTTT AACTTTTGT TTTCTTTTGA CTTGGGATAA     1080

AAGTTGAAAA GGTAAAAGGA AGGA                                           1104

(2) INFORMATION FOR SEQ ID NO: 11:

(i) SEQUENCE CHARACTERISTICS:
```

(A) LENGTH: 656 base pairs
        (B) TYPE: nucleic acid
        (C) STRANDEDNESS: single
        (D) TOPOLOGY: linear (xi) SEQUENCE DESCRIPTION: SEQ ID NO: 11:

```
TTGCATACAC TTAATCTTTT AAGCTTTGGT TTTATTATTA TAATATGGGG GTGATAACAG      60

TATCTACTTA ATAGAATTCT TGTTATTAAC ATGAAATAAT TAATGTTAAA CACAGCATAA     120

TATGTGTCAC ATTATAAAGA TTCAGGCAAT GTTTGTTAGT ATTAGTACTT TTTTTTCTTC     180

CTAAGTGCAA AAGATAACTT TATATCACTT TTAAACTTTT CTTTTAGTTG TGCTGAAAGA     240

CATTATGACA CCGCCAAATT TAATTGCAGA GGTAGGTATG AATGTACTGT ACTATGTTGT     300

ATAACTTAAA CCCGATAGAC TGTATCTTAC TGTCATAACA ATAATGAGTC ATCCAGATTA     360

TCGAGTGAGA TACATATTTA TCTTAAGAAT TATCTTTAAA AATTTCAAAA ATTTTAATTT     420

TACTGTTGTG TTTTAGGAAA AAGTATTGCA TAAAGCTATT AATATTGTCA GGAAGACTAA     480

AGTGCAGCAT AGACTAAGCA ATCAGGAAAA TTCCTAGACT AAAAATAGTA TAAGGAGAGG     540

GTTTACCTAC TATTTGAGGC AGTTGGTCTA ATAGTAAGCA ATCACAGGGA GGAAAGCAGA     600

AACTACTTAA CTCTTCTGTG TTGAGGAATG ACATAAAAGG TATGAAAGGA TATAAC         656
```

(2) INFORMATION FOR SEQ ID NO: 12:

(i) SEQUENCE CHARACTERISTICS:
        (A) LENGTH: 808 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 463..754
        (D) OTHER INFORMATION: /note = "N = C, G, A or T"

(xi) SEQUENCE DESCRIPTION: SEQ ID NO: 12:

```
ATACATTATT TTTCTCTGGA ATCCAGTGTT TCTTTTAAAT ACCTGTTAAG TTTGTATGCA      60

ACATTTCTAA AGTTACCTAC TTGTTAATTA AAAATTCAAG GGTTTTTTTT TCTTATTCTG     120

AGGTTATCTT TTTACCACAG TTGCACAATA TCCTTTTGAA GACCATAACC CACCACAGCT     180

AGAACTTATC AAACCCTTTT GTGAAGATCT TGACCAATGG CTAAGTGAAG ATGACAATCA     240

TGTTGCAGCA ATTCACTGTA AAGCTGGAAA GGGACGAACT GGTGTAATGA TATGTGCATA     300

TTTATTACAT CGGGGCAAAT TTTTAAAGGC ACAAGAGGCC CTAGATTTCT ATGGGGAAGT     360

AAGGACCAGA GACAAAAAGG TAAGTTATTT TTTGATGTTT TTCCTTTCCT CTTCCTGGAT     420

CTGAGAATTT ATTGGAAAAC AGATTTGGG TTTCTTTTTT TCNNNNNNNN NNNNNNNNNN     480

NNNNNNNNNN NNNNNNNNNN NNNNNNNNNN NNNNNNNNNN NNNNNNNNNN NNNNNNNNNN     540

NNNNNNNNNN NNNNNNNNNN NNNNNNNNNN NNNNNNNNNN NNNNNNNNNN NNNNNNNNNN     600

NNNNNNNNNN NNNNNNNNNN NNNNNNNNNN NNNNNNNNNN NNNNNNNNNN NNNNNNNNNN     660

NNNNNNNNNN NNNNNNNNNN NNNNNNNNNN NNNNNNNNNN NNNNNNNNNN NNNNNNNNNN     720

NNNNNNNNNN NTCCTCCCTC CCCACCCTCA GTCNCTGGAA AACAGGTTTT AAAGATAGTT     780

GCTAATCCTT ATTTCTTCTA AATTTTTA                                        808
```

(2) INFORMATION FOR SEQ ID NO: 13:

(i) SEQUENCE CHARACTERISTICS:
        (A) LENGTH: 670 base pairs
        (B) TYPE: nucleic acid (C) STRANDEDNESS: single
            (D) TOPOLOGY: linear (xi) SEQUENCE DESCRIPTION: SEQ ID NO: 13:

ATATGATAAT TGTTTTAAGG GAGGAGAGTT ATTCTGATAT CCTTGTATTG ATATTGCTCT      60

TATTTATTAT TGAGCTGGAT TTAAGTATTA ATCATTTAAG GTCAAATTTC TAATGTATAA     120

TATGTTCTTA AATGGCTACG ACCCAGTTAC CATAGCAATT TAGTGAAATA ACTATAATGG     180

AACATTTTTT TTCAATTTGG CTTCTCTTTT TTTTCTGTCC ACCAGGGAGT AACTATTCCC     240

AGTCAGAGGC GCTATGTGTA TTATTATAGC TACCTGTTAA AGAATCATCT GGATTATAGA     300

CCAGTGGCAC TGTTGTTTCA CAAGATGATG TTTGAAACTA TTCCAATGTT CAGTGGCGGA     360

ACTTGCAGTA AGTGCTTGGA AATTCTCATC CTTCCATGTA TTGGAACAGT TTTCTTAACC     420

ATATCTAGAA GTTTACATAA AAATTTAGAA AAGAAATTTA CCACATTTGA AATTTATGCA     480

GGAGACTATA TTTCTGAAGC ATTTGAACAA ATTAATTAGC TTTGTTGTTC AACTCATTGG     540

GCTAAAGAAG CCAAAAGCAA TGGGTTTTAA TGTAGTCGAA GCCAAATTAT ATTTATGAAA     600

GAAATATTCT GTGTTATAAC CCACCAAATA CAGCCCAATT TCTGACTAGA TGTATGGAAG     660

AACCTGTCCC                                                           670

(2) INFORMATION FOR SEQ ID NO: 14:

(i) SEQUENCE CHARACTERISTICS:
        (A) LENGTH: 661 base pairs
        (B) TYPE: nucleic acid
        (C) STRANDEDNESS: single
        (D) TOPOLOGY: linear (xi) SEQUENCE DESCRIPTION: SEQ ID NO: 14:

ATATTTTTAT TTCATTTATT TCAGTTGATT TGCTTGAGAT CAAGATTGCA GATACAGAAT      60

CCATATTTCG TGTATATTGC TGATATTAAT CATTAAAATC GTTTTTGACA GTTTGACAGT     120

TAAAGGCATT TCCTGTGAAA TAATACTGGT ATGTATTTAA CCATGCAGAT CCTCAGTTTG     180

TGGTCTGCCA GCTAAAGGTG AAGATATATT CCTCCAATTC AGGACCCACA CGACGGGAAG     240

ACAAGTTCAT GTACTTTGAG TTCCCTCAGC CGTTACCTGT GTGTGGTGAT ATCAAAGTAG     300

AGTTCTTCCA CAAACAGAAC AAGATGCTAA AAAAGGTTTG TACTTTACTT TCATTGGGAG     360

AAATATCCAA AATAAGGACA GATTAAAAGC TATATTTTAT TTTATGACAT GTAAGGAACT     420

ATAATTTGTT TTCTATTAGA TCTGCAGGTG TTTTGCTTAC TCTGGCATTG GTGAGACATT     480

ATAAGGGTAA ATAATCCTGT TTGAAGGAAA AGGCCTTATG GCATTGTAAC ATTAGAGGAA     540

TTTTTCTTAA CAAGGATGGT TAACTGAGAA GAAATTAGCA TGGGACCAAT ATTTTAAAAA     600

TTTTTGGTCT ATAGGTAGAA ATGAGATCTG TTCTGTGGTC TTATGTAGTG ACACAAACCA     660

C                                                                    661

(2) INFORMATION FOR SEQ ID NO: 15:

(i) SEQUENCE CHARACTERISTICS:
        (A) LENGTH: 739 base pairs
        (B) TYPE: nucleic acid
        (C) STRANDEDNESS: single
        (D) TOPOLOGY: linear (xi) SEQUENCE DESCRIPTION: SEQ ID NO: 15:

GTGTTCACCT TTATTCAGAA TATCAAATGA TAGTTTATTT TGTTGACTTT TTGCAAATGT      60

TTAACATAGG TGACAGATTT TCTTTTTTAA AAAAATAAAA CATCATTAAT TAAATATGTC     120

-continued

| | |
|---|---|
| ATTTCATTTC TTTTTCTTTT CTTTTTTTTT TTTTTTTAGG ACAAAATGTT TCACTTTTGG | 180 |
| GTAAATACAT TCTTCATACC AGGACCAGAG GAAACCTCAG AAAAAGTAGA AAATGGAAGT | 240 |
| CTATGTGATC AAGAAATCGA TAGCATTTGC AGTATAGAGC GTGCAGATAA TGACAAGGAA | 300 |
| TATCTAGTAC TTACTTTAAC AAAAAATGAT CTTGACAAAG CAAATAAAGA CAAAGCCAAC | 360 |
| CGATACTTTT CTCCAAATTT TAAGGTCAGT TAAATTAAAC ATTTTGTGGG GGTTGGTGAC | 420 |
| TTGTATGTAT GTGATGTGTG TTTAATTCTA GGAGTACAGC TGATGAAGAA CTTGCTTGAC | 480 |
| AAGTTTTTAA CTTATGTATT ATTTCGAAGC AGTGTTTACG TAGCAGTAAC ATGAAAGTTT | 540 |
| CTAATAAAAT ACCCAATGTA CACAGCGTCA AAAAAGCTGC ATTTTTCCTT TCCTAATTC | 600 |
| TTTGTTGTTT GCTGAAATCT GGGGCAAAGG TGCGGGAGGG GGCTAAATGA CTGGGATATG | 660 |
| AAGTAGGAAT GGGAGAGGAA AGAAATAGAT GGGAACTCAG TCATTTGGGA ATGATTCATA | 720 |
| TGGAATGTTT TTACTGCTT | 739 |

(2) INFORMATION FOR SEQ ID NO: 16:

(i) SEQUENCE CHARACTERISTICS:
        (A) LENGTH: 970 base pairs
        (B) TYPE: nucleic acid
        (C) STRANDEDNESS: single
        (D) TOPOLOGY: linear (xi) SEQUENCE DESCRIPTION: SEQ ID NO: 16:

| | |
|---|---|
| ATGAGCCAAG ATCATGCCAC TGCACTCCAG CTTGGCAACA GAGCAAGACT CTTGTCTCCA | 60 |
| GAAATAGAAA ATAAATAAAT TGTATTAACA TCCTGATAGT TTATCTGTCT AGTACCTAGC | 120 |
| AAGAAAGAAA ATGTTGAACA TCTTAAGAAG AGGGTCATTT AAAAGGCCTC TTAAAAGATC | 180 |
| ATGTTTGTTA CAGTGCTTAA AAATTAATAT GTTCATCTGC AAAATGGAAT AAAAAATCTG | 240 |
| TTAAAAATAT ATTTCACTAA ATAGTTTAAG ATGAGTCATA TTTGTGGGTT TTCATTTTAA | 300 |
| ATTTTCTTTC TCTAGGTGAA GCTGTACTTC ACAAAAACAG TAGAGGAGCC GTCAAATCCA | 360 |
| GAGGCTAGCA GTTCAACTTC TGTAACACCA GATGTTAGTG ACAATGAACC TGATCATTAT | 420 |
| AGATATTCTG ACACCACTGA CTCTGATCCA GAGAATGAAC CTTTTGATGA AGATCAGCAT | 480 |
| ACACAAATTA CAAAAGTCTG AATTTTTTTT TATCAAGAGG GATAAAACAC CATGAAAATA | 540 |
| AACTTGAATA AACTGAAAAT GGACCTTTTT TTTTTTAATG GCAATAGGAC ATTGTGTCAG | 600 |
| ATTACCAGTT ATAGGAACAA TTCTCTTTTC CTGACCAATC TTGTTTTACC CTATACATCC | 660 |
| ACAGGGTTTT GACACTTGTT GTCCAGTTGA AAAAAGGTTG TGTAGCTGTG TCATGTATAT | 720 |
| ACCTTTTTGT GTCAAAAGGA CATTTAAAAT TCAATTAGGA TTAATAAAGA TGGCACTTTC | 780 |
| CCGTTTTATT CCAGTTTTAT AAAAAGTGGA GACAGACTGA TGTGTATACG TAGGAATTTT | 840 |
| TTCCTTTTGT GTTCTGTCAC CAACTGAAGT GGCTAAAGAG CTTTGTGATA TACTGGTTCA | 900 |
| CATCCTACCC CTTTGCACTT GTGGCAACAG ATAAGTTTGC AGTTGGCTAA GAGAGGTTTC | 960 |
| CGAAAGGTTT | 970 |

(2) INFORMATION FOR SEQ ID NO: 17:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO: 17:

Ile His Cys Lys Ala Gly Lys Gly Arg Thr Gly (2) INFORMATION FOR SEQ ID NO: 18:

(i) SEQUENCE CHARACTERISTICS:
       (A) LENGTH: 11 amino acids
       (B) TYPE: amino acid
       (C) STRANDEDNESS:
       (D) TOPOLOGY: linear (ix) FEATURE:
       (A) NAME/KEY: Modified-site
       (B) LOCATION: 1
       (D) OTHER INFORMATION: /note = "may be either I =
           Isoleucine or V = Valine"

(ix) FEATURE:
       (A) NAME/KEY: Modified-site
       (B) LOCATION: 4..8
       (D) OTHER INFORMATION: /note = "X = Any amino acid"

(ix) FEATURE:
       (A) NAME/KEY: Modified-site
       (B) LOCATION: 10
       (D) OTHER INFORMATION: /note = "may be either S = Serine or
           T = Threonine"

(xi) SEQUENCE DESCRIPTION: SEQ ID NO: 18:

Ile His Cys Xaa Ala Gly Xaa Xaa Arg Ser Gly
1               5                   10

(2) INFORMATION FOR SEQ ID NO: 19:

(i) SEQUENCE CHARACTERISTICS:
       (A) LENGTH: 60 amino acids
       (B) TYPE: amino acid
       (C) STRANDEDNESS:
       (D) TOPOLOGY: linear (xi) SEQUENCE DESCRIPTION: SEQ ID NO: 19:

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Asn Glu Gly Val Tyr Arg Asn
        35                  40                  45

Asn Ile Asp Asp Val Val Arg Phe Leu Asp Ser Lys
    50                  55                  60

(2) INFORMATION FOR SEQ ID NO: 20:

(i) SEQUENCE CHARACTERISTICS:
       (A) LENGTH: 60 amino acids
       (B) TYPE: amino acid
       (C) STRANDEDNESS:
       (D) TOPOLOGY: linear (xi) SEQUENCE DESCRIPTION: SEQ ID NO: 20:

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys
    50                  55                  60

(2) INFORMATION FOR SEQ ID NO: 21:

(i) SEQUENCE CHARACTERISTICS:
        (A) LENGTH: 60 amino acids
        (B) TYPE: amino acid
        (C) STRANDEDNESS:
        (D) TOPOLOGY: linear (xi) SEQUENCE DESCRIPTION: SEQ ID NO: 21:

```
Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
                20                  25                  30

Ile Ala Met Glu Phe Pro Ala Glu Arg Leu Glu Gly Val Tyr Arg Asn
                35                  40                  45

Asn Ile Asp Asp Val Val Arg Phe Leu Asp Ser Lys
        50                  55                  60
```

(2) INFORMATION FOR SEQ ID NO: 22:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens (ix) FEATURE:
        (A) NAME/KEY: CDS
        (B) LOCATION: 1..1209

(xi) SEQUENCE DESCRIPTION: SEQ ID NO: 22:

```
ATG ACA GCC ATC ATC AAA GAG ATC GTT AGC AGA AAC AAA AGG AGA TAT      48
Met Thr Ala Ile Ile Lys Glu Ile Val Ser Arg Asn Lys Arg Arg Tyr
 1               5                  10                  15

CAA GAG GAT GGA TTC GAC TTA GAC TTG ACC TAT ATT TAT CCA AAC ATT      96
Gln Glu Asp Gly Phe Asp Leu Asp Leu Thr Tyr Ile Tyr Pro Asn Ile
                20                  25                  30

ATT GCT ATG GGA TTT CCT GCA GAA AGA CTT GAA GGC GTA TAC AGG AAC     144
Ile Ala Met Gly Phe Pro Ala Glu Arg Leu Glu Gly Val Tyr Arg Asn
                35                  40                  45

AAT ATT GAT GAT GTA GTA AGG TTT TTG GAT TCA AAG CAT AAA AAC CAT     192
Asn Ile Asp Asp Val Val Arg Phe Leu Asp Ser Lys His Lys Asn His
        50                  55                  60

TAC AAG ATA TAC AAT CTT TGT GCT GAA AGA CAT TAT GAC ACC GCC AAA     240
Tyr Lys Ile Tyr Asn Leu Cys Ala Glu Arg His Tyr Asp Thr Ala Lys
65                  70                  75                  80

TTT AAT TGC AGA GTT GCA CAA TAT CCT TTT GAA GAC CAT AAC CCA CCA     288
Phe Asn Cys Arg Val Ala Gln Tyr Pro Phe Glu Asp His Asn Pro Pro
                85                  90                  95

CAG CTA GAA CTT ATC AAA CCC TTT TGT GAA GAT CTT GAC CAA TGG CTA     336
Gln Leu Glu Leu Ile Lys Pro Phe Cys Glu Asp Leu Asp Gln Trp Leu
                100                 105                 110

AGT GAA GAT GAC AAT CAT GTT GCA GCA ATT CAC TGT AAA GCT GGA AAG     384
Ser Glu Asp Asp Asn His Val Ala Ala Ile His Cys Lys Ala Gly Lys
                115                 120                 125

GGA CGA ACT GGT GTA ATG ATA TGT GCA TAT TTA TTA CAT CGG GGC AAA     432
Gly Arg Thr Gly Val Met Ile Cys Ala Tyr Leu Leu His Arg Gly Lys
                130                 135                 140
```

```
TTT TTA AAG GCA CAA GAG GCC CTA GAT TTC TAT GGG GAA GTA AGG ACC      480
Phe Leu Lys Ala Gln Glu Ala Leu Asp Phe Tyr Gly Glu Val Arg Thr
145                 150                 155                 160

AGA GAC AAA AAG GGA GTA ACT ATT CCC AGT CAG AGG CGC TAT GTG TAT      528
Arg Asp Lys Lys Gly Val Thr Ile Pro Ser Gln Arg Arg Tyr Val Tyr
                165                 170                 175

TAT TAT AGC TAC CTG TTA AAG AAT CAT CTG GAT TAT AGA CCA GTG GCA      576
Tyr Tyr Ser Tyr Leu Leu Lys Asn His Leu Asp Tyr Arg Pro Val Ala
            180                 185                 190

CTG TTG TTT CAC AAG ATG ATG TTT GAA ACT ATT CCA ATG TTC AGT GGC      624
Leu Leu Phe His Lys Met Met Phe Glu Thr Ile Pro Met Phe Ser Gly
        195                 200                 205

GGA ACT TGC AAT CCT CAG TTT GTG GTC TGC CAG CTA AAG GTG AAG ATA      672
Gly Thr Cys Asn Pro Gln Phe Val Val Cys Gln Leu Lys Val Lys Ile
210                 215                 220

TAT TCC TCC AAT TCA GGA CCC ACA CGA CGG GAA GAC AAG TTC ATG TAC      720
Tyr Ser Ser Asn Ser Gly Pro Thr Arg Arg Glu Asp Lys Phe Met Tyr
225                 230                 235                 240

TTT GAG TTC CCT CAG CCG TTA CCT GTG TGT GGT GAT ATC AAA GTA GAG      768
Phe Glu Phe Pro Gln Pro Leu Pro Val Cys Gly Asp Ile Lys Val Glu
                245                 250                 255

TTC TTC CAC AAA CAG AAC AAG ATG CTA AAA AAG GAC AAA ATG TTT CAC      816
Phe Phe His Lys Gln Asn Lys Met Leu Lys Lys Asp Lys Met Phe His
            260                 265                 270

TTT TGG GTA AAT ACA TTC TTC ATA CCA GGA CCA GAG GAA ACC TCA GAA      864
Phe Trp Val Asn Thr Phe Phe Ile Pro Gly Pro Glu Glu Thr Ser Glu
        275                 280                 285

AAA GTA GAA AAT GGA AGT CTA TGT GAT CAA GAA ATC GAT AGC ATT TGC      912
Lys Val Glu Asn Gly Ser Leu Cys Asp Gln Glu Ile Asp Ser Ile Cys
290                 295                 300

AGT ATA GAG CGT GCA GAT AAT GAC AAG GAA TAT CTA GTA CTT ACT TTA      960
Ser Ile Glu Arg Ala Asp Asn Asp Lys Glu Tyr Leu Val Leu Thr Leu
305                 310                 315                 320

ACA AAA AAT GAT CTT GAC AAA GCA AAT AAA GAC AAA GCC AAC CGA TAC     1008
Thr Lys Asn Asp Leu Asp Lys Ala Asn Lys Asp Lys Ala Asn Arg Tyr
                325                 330                 335

TTT TCT CCA AAT TTT AAG GTG AAG CTG TAC TTC ACA AAA ACA GTA GAG     1056
Phe Ser Pro Asn Phe Lys Val Lys Leu Tyr Phe Thr Lys Thr Val Glu
            340                 345                 350

GAG CCG TCA AAT CCA GAG GCT AGC AGT TCA ACT TCT GTA ACA CCA GAT     1104
Glu Pro Ser Asn Pro Glu Ala Ser Ser Ser Thr Ser Val Thr Pro Asp
        355                 360                 365

GTT AGT GAC AAT GAA CCT GAT CAT TAT AGA TAT TCT GAC ACC ACT GAC     1152
Val Ser Asp Asn Glu Pro Asp His Tyr Arg Tyr Ser Asp Thr Thr Asp
370                 375                 380

TCT GAT CCA GAG AAT GAA CCT TTT GAT GAA GAT CAG CAT ACA CAA ATT     1200
Ser Asp Pro Glu Asn Glu Pro Phe Asp Glu Asp Gln His Thr Gln Ile
385                 390                 395                 400

ACA AAA GTC                                                         1209
Thr Lys Val (2) INFORMATION FOR SEQ ID NO: 23:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO: 23:
```

```
Met Thr Ala Ile Ile Lys Glu Ile Val Ser Arg Asn Lys Arg Tyr
 1               5                  10                  15

Gln Glu Asp Gly Phe Asp Leu Asp Leu Thr Tyr Ile Tyr Pro Asn Ile
             20                  25                  30

Ile Ala Met Gly Phe Pro Ala Glu Arg Leu Glu Gly Val Tyr Arg Asn
             35                  40                  45

Asn Ile Asp Asp Val Val Arg Phe Leu Asp Ser Lys His Lys Asn His
     50                  55                  60

Tyr Lys Ile Tyr Asn Leu Cys Ala Glu Arg His Tyr Asp Thr Ala Lys
 65                  70                  75                  80

Phe Asn Cys Arg Val Ala Gln Tyr Pro Phe Glu Asp His Asn Pro Pro
                 85                  90                  95

Gln Leu Glu Leu Ile Lys Pro Phe Cys Glu Asp Leu Asp Gln Trp Leu
                100                 105                 110

Ser Glu Asp Asp Asn His Val Ala Ala Ile His Cys Lys Ala Gly Lys
                115                 120                 125

Gly Arg Thr Gly Val Met Ile Cys Ala Tyr Leu Leu His Arg Gly Lys
        130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Thr Ser Glu
            275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
                355                 360                 365

Val Ser Asp Asn Glu Pro Asp His Tyr Arg Tyr Ser Asp Thr Thr Asp
        370                 375                 380

Ser Asp Pro Glu Asn Glu Pro Phe Asp Glu Asp Gln His Thr Gln Ile
385                 390                 395                 400

Thr Lys Val
```

(2) INFORMATION FOR SEQ ID NO: 24:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Mus musculus (ix) FEATURE:
        (A) NAME/KEY: CDS
        (B) LOCATION: 1..1209

(xi) SEQUENCE DESCRIPTION: SEQ ID NO: 24:

```
ATG ACA GCC ATC ATC AAA GAG ATC GTT AGC AGA AAC AAA AGG AGA TAT       48
Met Thr Ala Ile Ile Lys Glu Ile Val Ser Arg Asn Lys Arg Arg Tyr
405                 410                 415

CAA GAG GAT GGA TTC GAC TTA GAC TTG ACC TAT ATT TAT CCA AAT ATT       96
Gln Glu Asp Gly Phe Asp Leu Asp Leu Thr Tyr Ile Tyr Pro Asn Ile
420                 425                 430                 435

ATT GCT ATG GGA TTT CCT GCA GAA AGA CTT GAA GGT GTA TAC AGG AAC      144
Ile Ala Met Gly Phe Pro Ala Glu Arg Leu Glu Gly Val Tyr Arg Asn
                440                 445                 450

AAT ATT GAT GAT GTA GTA AGG TTT TTG GAT TCA AAG CAT AAA AAC CAT      192
Asn Ile Asp Asp Val Val Arg Phe Leu Asp Ser Lys His Lys Asn His
                455                 460                 465

TAC AAG ATA TAC AAT CTA TGT GCT GAG AGA CAT TAT GAC ACC GCC AAA      240
Tyr Lys Ile Tyr Asn Leu Cys Ala Glu Arg His Tyr Asp Thr Ala Lys
                470                 475                 480

TTT AAC TGC AGA GTT GCA CAG TAT CCT TTT GAA GAC CAT AAC CCA CCA      288
Phe Asn Cys Arg Val Ala Gln Tyr Pro Phe Glu Asp His Asn Pro Pro
485                 490                 495

CAG CTA GAA CTT ATC AAA CCC TTC TGT GAA GAT CTT GAC CAA TGG CTA      336
Gln Leu Glu Leu Ile Lys Pro Phe Cys Glu Asp Leu Asp Gln Trp Leu
500                 505                 510                 515

AGT GAA GAT GAC AAT CAT GTT GCA GCA ATT CAC TGT AAA GCT GGA AAG      384
Ser Glu Asp Asp Asn His Val Ala Ala Ile His Cys Lys Ala Gly Lys
                520                 525                 530

GGA CGG ACT GGT GTA ATG ATT TGT GCA TAT TTA TTG CAT CGG GGC AAA      432
Gly Arg Thr Gly Val Met Ile Cys Ala Tyr Leu Leu His Arg Gly Lys
                535                 540                 545

TTT TTA AAG GCA CAA GAG GCC CTA GAT TTT TAT GGG GAA GTA AGG ACC      480
Phe Leu Lys Ala Gln Glu Ala Leu Asp Phe Tyr Gly Glu Val Arg Thr
                550                 555                 560

AGA GAC AAA AAG GGA GTC ACA ATT CCC AGT CAG AGG CGC TAT GTA TAT      528
Arg Asp Lys Lys Gly Val Thr Ile Pro Ser Gln Arg Arg Tyr Val Tyr
565                 570                 575

TAT TAT AGC TAC CTG CTA AAA AAT CAC CTG GAT TAC AGA CCC GTG GCA      576
Tyr Tyr Ser Tyr Leu Leu Lys Asn His Leu Asp Tyr Arg Pro Val Ala
580                 585                 590                 595

CTG CTG TTT CAC AAG ATG ATG TTT GAA ACT ATT CCA ATG TTC AGT GGC      624
Leu Leu Phe His Lys Met Met Phe Glu Thr Ile Pro Met Phe Ser Gly
                600                 605                 610

GGA ACT TGC AAT CCT CAG TTT GTG GTC TGC CAG CTA AAG GTG AAG ATA      672
Gly Thr Cys Asn Pro Gln Phe Val Val Cys Gln Leu Lys Val Lys Ile
                615                 620                 625

TAT TCC TCC AAT TCA GGA CCC ACG CGG CGG GAG GAC AAG TTC ATG TAC      720
Tyr Ser Ser Asn Ser Gly Pro Thr Arg Arg Glu Asp Lys Phe Met Tyr
                630                 635                 640

TTT GAG TTC CCT CAG CCA TTG CCT GTG TGT GGT GAT ATC AAA GTA GAG      768
```

```
                                                                            -continued Phe Glu Phe Pro Gln Pro Leu Pro Val Cys Gly Asp Ile Lys Val Glu
    645                 650                 655

TTC TTC CAC AAA CAG AAC AAG ATG CTC AAA AAG GAC AAA ATG TTT CAC              816
Phe Phe His Lys Gln Asn Lys Met Leu Lys Lys Asp Lys Met Phe His
660                 665                 670                 675

TTT TGG GTA AAT ACG TTC TTC ATA CCA GGA CCA GAG GAA ACC TCA GAA              864
Phe Trp Val Asn Thr Phe Phe Ile Pro Gly Pro Glu Glu Thr Ser Glu
                680                 685                 690

AAA GTG GAA AAT GGA AGT CTT TGT GAT CAG GAA ATC GAT AGC ATT TGC              912
Lys Val Glu Asn Gly Ser Leu Cys Asp Gln Glu Ile Asp Ser Ile Cys
                695                 700                 705

AGT ATA GAG CGT GCA GAT AAT GAC AAG GAG TAT CTT GTA CTC ACC CTA              960
Ser Ile Glu Arg Ala Asp Asn Asp Lys Glu Tyr Leu Val Leu Thr Leu
            710                 715                 720

ACA AAA AAC GAT CTT GAC AAA GCA AAC AAA GAC AAG GCC AAC CGA TAC             1008
Thr Lys Asn Asp Leu Asp Lys Ala Asn Lys Asp Lys Ala Asn Arg Tyr
725                 730                 735

TTC TCT CCA AAT TTT AAG GTG AAA CTA TAC TTT ACA AAA ACA GTA GAG             1056
Phe Ser Pro Asn Phe Lys Val Lys Leu Tyr Phe Thr Lys Thr Val Glu
740                 745                 750                 755

GAG CCA TCA AAT CCA GAG GCT AGC AGT TCA ACT TCT GTG ACT CCA GAT             1104
Glu Pro Ser Asn Pro Glu Ala Ser Ser Ser Thr Ser Val Thr Pro Asp
                760                 765                 770

GTT AGT GAC AAT GAA CCT GAT CAT TAT AGA TAT TCT GAC ACC ACT GAC             1152
Val Ser Asp Asn Glu Pro Asp His Tyr Arg Tyr Ser Asp Thr Thr Asp
                775                 780                 785

TCT GAT CCA GAG AAT GAA CCT TTT GAT GAA GAT CAG CAT TCA CAA ATT             1200
Ser Asp Pro Glu Asn Glu Pro Phe Asp Glu Asp Gln His Ser Gln Ile
            790                 795                 800

ACA AAA GTC                                                                 1209
Thr Lys Val
    805

(2) INFORMATION FOR SEQ ID NO: 25:

(i) SEQUENCE CHARACTERISTICS:
         (A) LENGTH: 403 amino acids
         (B) TYPE: amino acid
         (D) TOPOLOGY: linear (ii) MOLECULE TYPE: protein (xi) SEQUENCE DESCRIPTION: SEQ ID NO: 25:

Met Thr Ala Ile Ile Lys Glu Ile Val Ser Arg Asn Lys Arg Arg Tyr
 1               5                  10                  15

Gln Glu Asp Gly Phe Asp Leu Asp Leu Thr Tyr Ile Tyr Pro Asn Ile
                20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
                100                 105                 110

Ser Glu Asp Asp Asn His Val Ala Ala Ile His Cys Lys Ala Gly Lys
            115                 120                 125
```

```
Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
                260                 265                 270

Phe Trp Val Asn Thr Phe Phe Ile Pro Gly Pro Glu Glu Thr Ser Glu
            275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Thr Ser Val Thr Pro Asp
            355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Ser Gln Ile
385                 390                 395                 400

Thr Lys Val (2) INFORMATION FOR SEQ ID NO: 26:

(i) SEQUENCE CHARACTERISTICS:
        (A) LENGTH: 1183 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Canis familiaris (ix) FEATURE:
        (A) NAME/KEY: CDS
        (B) LOCATION: 1..1183

(xi) SEQUENCE DESCRIPTION: SEQ ID NO: 26:

ATG ACA GCC ATC ATC AAG GAG ATC GTC AGC AGA AAC AAA AGG CGC TAC        48
Met Thr Ala Ile Ile Lys Glu Ile Val Ser Arg Asn Lys Arg Arg Tyr
    405                 410                 415

CAG GAG GAT GGG TTC GAC TTG GAC TTG ACC TAT ATT TAT CCC AAC ATT        96
Gln Glu Asp Gly Phe Asp Leu Asp Leu Thr Tyr Ile Tyr Pro Asn Ile
```

```
420                     425                     430                     435
ATT GCT ATG GGG TTT CCT GCA GAA AGA CTT GAA GGC GTA TAC AGG AAC        144
Ile Ala Met Gly Phe Pro Ala Glu Arg Leu Glu Gly Val Tyr Arg Asn
                440                     445                     450

AAT ATT GAT GAT GTA GTA AGG TTT TTG GAT TCA AAG CAT AAA AAC CAT        192
Asn Ile Asp Asp Val Val Arg Phe Leu Asp Ser Lys His Lys Asn His
                455                     460                     465

TAC AAG ATA TAC AAT CTG TGT GCT GAA AGA CAT TAT GAT ACC GCC AAA        240
Tyr Lys Ile Tyr Asn Leu Cys Ala Glu Arg His Tyr Asp Thr Ala Lys
                470                     475                     480

TTT AAC TGC AGA GTT GCA CAG TAT CCT TTT GAA GAC CAT AAT CCA CCA        288
Phe Asn Cys Arg Val Ala Gln Tyr Pro Phe Glu Asp His Asn Pro Pro
                485                     490                     495

CAG CTA GAA CTT ATC AAA CCC TTT TGT GAA GAT CTT GAC CAA TGG CTA        336
Gln Leu Glu Leu Ile Lys Pro Phe Cys Glu Asp Leu Asp Gln Trp Leu
500                     505                     510                     515

AGT GAA GAT GAC AAT CAT GTT GCA GCA ATT CAC TGT AAA GCT GGA AAG        384
Ser Glu Asp Asp Asn His Val Ala Ala Ile His Cys Lys Ala Gly Lys
                520                     525                     530

GGA CGA ACT GGT GTA ATG ATT TGT GCA TAT TTA TTA CAT CGG GGC AAA        432
Gly Arg Thr Gly Val Met Ile Cys Ala Tyr Leu Leu His Arg Gly Lys
                535                     540                     545

TTT CTA AAG GCA CAA GAG GCC CTA GAT TTC TAT GGG GAA GTA AGG ACC        480
Phe Leu Lys Ala Gln Glu Ala Leu Asp Phe Tyr Gly Glu Val Arg Thr
                550                     555                     560

AGA GAC AAA AAG GGA GTA ACT ATT CCC AGT CAG AGG CGC TAT GTG TAT        528
Arg Asp Lys Lys Gly Val Thr Ile Pro Ser Gln Arg Arg Tyr Val Tyr
                565                     570                     575

TAT TAT AGC TAC CTG TTA AAG AAT CAT CTG GAT TAT AGA CCA GTG GCA        576
Tyr Tyr Ser Tyr Leu Leu Lys Asn His Leu Asp Tyr Arg Pro Val Ala
580                     585                     590                     595

CTG TTG TTT CAC AAG ATG ATG TTT GAA ACT ATT CCA ATG TTC AGT GGC        624
Leu Leu Phe His Lys Met Met Phe Glu Thr Ile Pro Met Phe Ser Gly
                600                     605                     610

GGA ACT TGC AAT CCT CAG TTT GTG GTC TGC CAG CTA AAG GTG AAG ATC        672
Gly Thr Cys Asn Pro Gln Phe Val Val Cys Gln Leu Lys Val Lys Ile
                615                     620                     625

TAT TCC TCC AAT TCA GGA CCC ACA CGA CGG GAA GAC AAG TTC ATG TAC        720
Tyr Ser Ser Asn Ser Gly Pro Thr Arg Arg Glu Asp Lys Phe Met Tyr
                630                     635                     640

TTT GAG TTC CCT CAG CCA TTG CCT GTG TGC GGT GAC ATC AAA GTA GAG        768
Phe Glu Phe Pro Gln Pro Leu Pro Val Cys Gly Asp Ile Lys Val Glu
                645                     650                     655

TTC TTC CAC AAA CAG AAC AAG ATG CTA AAA AAG GAC AAA ATG TTT CAC        816
Phe Phe His Lys Gln Asn Lys Met Leu Lys Lys Asp Lys Met Phe His
660                     665                     670                     675

TTT TGG GTA AAC ACA TTC TTC ATA CCA GGA CCA GAG GAA ACC TCA GAA        864
Phe Trp Val Asn Thr Phe Phe Ile Pro Gly Pro Glu Glu Thr Ser Glu
                680                     685                     690

AAA GTA GAA AAT GGA AGT CTA TGT GAT CAA GAA ATT GAT AGT ATT TGC        912
Lys Val Glu Asn Gly Ser Leu Cys Asp Gln Glu Ile Asp Ser Ile Cys
                695                     700                     705

AGT ATA GAA CGT GCA GAT AAT GAC AAG GAA TAT CTA GTA CTC ACT TTA        960
Ser Ile Glu Arg Ala Asp Asn Asp Lys Glu Tyr Leu Val Leu Thr Leu
                710                     715                     720

ACA AAA AAT GAT CTC GAC AAA GCA AAT AAA GAC AAG GCC AAC CGA TAT       1008
Thr Lys Asn Asp Leu Asp Lys Ala Asn Lys Asp Lys Ala Asn Arg Tyr
                725                     730                     735

TTT TCT CCA AAT TTT AAG GTG AAG CTG TAC TTC ACA AAA ACT GTA GAG       1056
```

```
Phe Ser Pro Asn Phe Lys Val Lys Leu Tyr Phe Thr Lys Thr Val Glu
740                 745                 750                 755

GAG CCA TCA AAC CCG GAG GCT AGC AGT TCA ACT TCT GTG ACG CCA GAT      1104
Glu Pro Ser Asn Pro Glu Ala Ser Ser Ser Thr Ser Val Thr Pro Asp
            760                 765                 770

GTT AGT GAC AAT GAA CCT GAT CAT TAT AGA TAT TCT GAC ACC ACT GAC      1152
Val Ser Asp Asn Glu Pro Asp His Tyr Arg Tyr Ser Asp Thr Thr Asp
            775                 780                 785

TCT GAC CCA GAG AAT GAA CCC TTT GAT GAA G                            1183
Ser Asp Pro Glu Asn Glu Pro Phe Asp Glu
            790                 795
```

(2) INFORMATION FOR SEQ ID NO: 27:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
            35                  40                  45

Asn Ile Asp Asp Val Val Arg Phe Leu Asp Ser Lys His Lys Asn His
        50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
            85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
            115                 120                 125

Gly Arg Thr Gly Val Met Ile Cys Ala Tyr Leu Leu His Arg Gly Lys
130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
            165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
            195                 200                 205

Gly Thr Cys Asn Pro Gln Phe Val Val Cys Gln Leu Lys Val Lys Ile
            210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
            245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
```

-continued

```
                275                 280                 285
Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
                340                 345                 350

Glu Pro Ser Asn Pro Glu Ala Ser Ser Ser Thr Ser Val Thr Pro Asp
                355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu
385                 390
```

TUMOR SUPPRESSOR DESIGNATED TS10Q23.3

The government may own rights in the present invention pursuant to a grant from the National Institutes of Health, grant no. CA56041.

BACKGROUND OF THE INVENTION

I. Field of the Invention

The present invention relates to the fields of oncology, genetics and molecular biology. More particular the invention relates to the identification, on human chromosome 10, of a tumor suppressor gene. Defects in this gene are associated with the development of cancers, such as gliomas.

II. Related Art

Oncogenesis was described by Foulds (1958) as a multi-step biological process, which is presently known to occur by the accumulation of genetic damage. On a molecular level, the multistep process of tumorigenesis involves the disruption of both positive and negative regulatory effectors (Weinberg, 1989). The molecular basis for human colon carcinomas has been postulated, by Vogelstein and coworkers (1990), to involve a number of oncogenes, tumor suppressor genes and repair genes. Similarly, defects leading to the development of retinoblastoma have been linked to another tumor suppressor gene (Lee et al., 1987). Still other oncogenes and tumor suppressors have been identified in a variety of other malignancies. Unfortunately, there remains an inadequate number of treatable cancers, and the effects of cancer are catastrophic—over half a million deaths per year in the United States alone.

One example of the devastating nature of cancer involves tumors arising from cells of the astrocytic lineage are the most common primary tumors of the central nervous system (Russell & Rubinstein, 1989). The majority of these tumors occur in the adult population. Primary brain tumors also account for the most common solid cancer in the pediatric patient population and the second leading cause of cancer deaths in children younger than 15 years of age. An estimated 18,500 new cases of primary brain tumors were diagnosed in 1994 (Boring et al., 1994). Epidemiological studies show that the incidence of brain tumors is increasing and represents the third most common cause of cancer death among 18 to 35 year old patients. Due to their location within the brain and the typical infiltration of tumor cells into the surrounding tissue, successful therapeutic intervention for primary brain tumors often is limited. Unfortunately, about two-thirds of these afflicted individuals will succumb to the disease within two years. The most common intracranial tumors in adults arise from cells of the glial lineage and occur at an approximately frequency of 48% glioblastoma multiforme (GBM), 21% astrocytomas (A) (anaplastic (AA) and low grade) and 9% ependymomas and oligodendrogliomas (Levin et al., 1993).

Genetic studies have implicated several genes, and their corresponding protein products, in the oncogenesis of primary brain tumors. Among the various reported alterations are: amplification of epidermal growth factor receptor and one of its ligands, transforming growth factor-alpha, N-myc; gli, altered splicing and expression of fibroblast growth factor receptors, and loss of function of p53, p16, Rb, neurofibromatosis genes 1 and 2, DCC, and putative tumor suppressor genes on chromosomes 4, 10, 17 (non-p53), 19, 22, and X (Wong et al., 1987; El-Azouzi et al., 1989; Nishi et al., 1991; James et al., 1988; Kamb et al., 1994; Henson et al., 1994; Yamaguchi et al., 1994; Bianchi et al., 1994; Ransom et al., 1992; Rasheed et al., 1992; Scheck and Coons, 1993; Von Demling et al., 1994; Rubio et al., 1994; Ritland et al., 1995).

The most frequent alterations include amplification of EGF-receptor (~40%), loss of function of p53 (~50%), p16 (~50%), Rb (~30%) and deletions on chromosome 10 (>90%). Furthermore, the grade or degree of histological malignancy of astrocytic tumors correlates with increased accumulation of genetic damage similar to colon carcinoma. Moreover, some changes appear to be relatively lineage- or grade-specific. For instance, losses to chromosome 19q occur predominantly in oligodendrogliomas, while deletions to chromosome 10 and amplification and mutation of the EGF-receptor occur mainly in GBMs. The deletion of an entire copy or segments of chromosome 10 is strongly indicated as the most common genetic event associated with the most common form of primary brain tumors, GBMs.

Cytogenetic and later allelic deletion studies on GBMs clearly have demonstrated frequent and extensive molecular genetic alterations associated with chromosome 10 (Bigner et al., 1988; Ransom et al., 1992; Rasheed et al., 1992; James et al., 1988: Fujimoto et al., 1989; Fults et al., 1990, 1993; Karlbom et al., 1993; Rasheed et al., 1995; Sonoda et al, 1996; Albarosa et al., 1996). Cytogenetic analyses have clearly shown the alteration of chromosome 10 as a common occurrence in GBMs, with 60% of tumors exhibiting alteration. Allelic deletion studies of GBMs have also revealed very frequent allelic imbalances associated with chromosome 10 (90%). However, the losses are so extensive and frequent that no chromosomal sublocalization of a consistent loss could be unequivocally defined by these analyses.

Several recent studies have implicated the region 10q25-26, specifically a 17 cM region from D10S190 to D10S216. A telomeric region from D10S587 to D10S216 was implicated by allelic deletion analysis using a series of low and high grade gliomas that exhibited only a partial loss of chromosome 10 (Rasheed et al, 1995). This region (~1 cM) was lost or noninformative in 11 GBM's, 4 AA's, 1 A and 1 oligodendroglioma, suggesting localization of a candidate region. This study also illustrated that deletions to chromosome 10 occur in lower grade gliomas. Albarosa et al. (1996) suggest a centromeric candidate region based on a small allelic deletion in a pediatric brain tumor from the makers D10S221 to D10S209. Saya et al., using a series of GBMs, have suggested two common regions of deletions, 10q26 and 10q24 (D10S192).

The short arm of chromosome 10 also has been implicated to contain another tumor suppressor gene. Studies first provided functional evidence of a tumor suppressor gene on 10p in glioma (Steck et al, 1995) which was later shown for prostate (Sanchez et al., 1995; Murakami et al., 1996). The latter study has implicated a 11 cM region between D10S1172 and D10S527. Allelic deletion studies of gliomas have shown extensive deletion on 10p, but again, no firm localization has been achieved (Karlbom et al., 1993; Kimmelman et al., 1996; these regions of chromosome 10 are shown to FIG. 1, below). Furthermore, the amplification of EGF-receptor has also been shown to occur almost exclusively in tumors that had deletions in chromosome 10, suggesting a possible link between these genetic alterations (Von Deimling et al., 1992).

Deletions on the long arm, particularly 10q24, also have been reported for prostate, renal, uterine, small-cell lung, endometrial carcinomas, meningioma and acute T-cell leukemias (Carter et al., 1990; Morita et al, 1991; Herbst et al., 1984; Jones et al., 1994; Rempel et al., 1993; Peiffen et al., 1995; Petersen et al., 1997). Recently, detailed studies on prostate carcinoma have shown that (1) the short and long arm of chromosome 10 strongly appear to contain tumor suppressor genes, and (2) the localization of the long arm suppressor gene maps to the 10q23-24 boundary (Gray et al., 1995; Ittmann, 1996, Trybus et al., 1996). The region of common deletion identified by these three groups is centered around D10S215 and extends about 10 cM (FIG. 1). The region overlaps with our candidate region, however, no further localization within the region was reported fro prostate carcinoma. The allelic losses associated with prostate carcinoma also appear to occur in only about 30–40% of the tumors examined. Furthermore, deletions are observed in more advance staged tumors, similar to GBMs, and may be related to metastatic ability (Nihei et al., 1995; Komiya et al., 1996). The combination of these results suggest that multiple human cancers implicate the region 10q23-24.

Differences in locations of the candidate regions suggest several possibilities. First, the presence of two or more tumor suppressor genes on 10q are possible. Second, not all deletions may effect the tumor suppressor gene locus. These alternatives are not mutually exclusive. In support of the latter possibility, a potential latent centromere was suggested to occur at 10q25 which may give rise to genetic alterations, particularly breakage (Vouillaire et al., 1993).

Despite all of this information, the identity of the gene (or genes) involved with the 10q23-24-related tumor suppression remained elusive. Without identification of a specific gene and deduction of the protein for which it codes, it is impossible to begin developing an effective therapy targeting this product. Thus, it is an important goal to isolate the tumor suppressor(s) located in this region and determine its structure and function.

SUMMARY OF THE INVENTION

Therefore, it is an objective of the present invention to provide a tumor suppressor, designated as TS10q23.3. Also an objective to provide DNAs representing all or part of a gene encoding TS10q23.3. It also is an objective to provides methods for using these compositions.

In accordance with the foregoing objectives, there is provided, in one embodiment, a tumor suppressor designated as TS10q23.3. The polypeptide has, in one example, the amino acid sequence as set forth in FIG. 7 or FIG. 9. Also provided is an isolated peptide having between about 10 and about 50 consecutive residues of a tumor suppressor designated as TS10q23.3. The peptide may be conjugated to a carrier molecule, for example, KLH or BSA.

In another embodiment, there is provided a monoclonal antibody that binds immunologically to a tumor suppressor designated as TS10q23.3. The antibody may be non-cross reactive with other human polypeptides, or it may bind to non-human TS10q23.3, but not to human TS10q23.3. The antibody may further comprise a detectable label, such as a fluorescent label, a chemiluminescent label, a radiolabel or an enzyme. Also encompassed are hybridoma cells and cell lines producing such antibodies.

In another embodiment, there is included a polyclonal antisera, antibodies of which bind immunologically to a tumor suppressor designated as TS10q23.3. The antisera may be derived from any animal, but preferably is from other than human, mouse or dog.

In still another embodiment, there is provided an isolated nucleic acid comprising a region, or the complement thereof, encoding a tumor suppressor designated TS10q23.3 or an allelic variant or mutant thereof. The tumor suppressor coding region may be derived from any mammal but, in particular embodiments, is selected from murine, canine and human sequences. Mutations include deletion mutants, insertion mutants, frameshift mutants, nonsense mutants, missense mutants or splice mutants. In a particular embodiment, the tumor suppressor has the amino acid sequence of FIG. 9. The nucleic acid may be genomic DNA, complementary DNA or RNA.

In additional embodiments, the nucleic acid comprises a complementary DNA and further comprises a promoter operably linked to the region, or the complement thereof, encoding the tumor suppressor. Additional elements include a polyadenylation signal and an origin of replication.

Viral vectors such as retrovirus, adenovirus, herpesvirus, vaccinia virus and adeno-associated virus also may be employed. The vector may be "naked" or packaged in a virus particle. Alternatively, the nucleic acid may comprise an expression vector packaged in a liposome.

Various sizes of nucleic acids are contemplated, but are not limiting: about 1212 bases, about 1500 bases, about 2000 bases, about 3500 bases, about 5000 bases, about 10,000 bases, about 15,000 bases, about 20,000 bases, about 25,000 bases, about 30,000 bases, about 35,000 bases, about 40,000 bases, about 45,000 bases, about 50,000 bases, about 75,000 bases and about 100,000 bases.

In still yet another embodiment, there is provided an isolated oligonucleotide of between about 10 and about 50 consecutive bases of a nucleic acid, or complementary thereto, encoding a tumor suppressor designated as TS10q23.3. The oligonucleotide may be about 15 bases in length, about 17 bases in length, about 20 bases in length, about 25 bases in length or about 50 bases in length.

In still yet another embodiment, there is provided a method of diagnosing a cancer comprising the steps of (i) obtaining a sample from a subject; and (ii) determining the expression a functional TS10q23.3 tumor suppressor in cells of the sample. The cancer may be brain, lung, liver, spleen, kidney, lymph node, small intestine, pancreas, blood cells, colon, stomach, breast, endometrium, prostate, testicle, ovary, skin, head and neck, esophagus, bone marrow and blood cancer. In preferred embodiments, the cancer is prostate cancer or breast cancer. In another preferred embodiment, cancer is a brain cancer, for example, a glioma. The sample is a tissue or fluid sample.

In one format, the method involves assaying for a nucleic acid from the sample. The method may further comprise subjecting the sample to conditions suitable to amplify the nucleic acid. Alternatively, the method may comprises contacting the sample with an antibody that binds immunologically to a TS10q23.3, for example, in an ELISA. The comparison, regardless of format, may include comparing the expression of TS10q23.3 with the expression of TS10q23.3 in non-cancer samples. The comparison may look at levels of TS10q23.3 expression. Alternatively, the comparison may involve evaluating the structure of the TS10q23.3 gene, protein or transcript. Such formats may include sequencing, wild-type oligonucleotide hybridization, mutant oligonucleotide hybridization, SSCP, PCR and RNase protection. Particular embodiments include evaluating wild-type or mutant oligonucleotide hybridization where the oligonucleotide is configured in an array on a chip or wafer.

In another embodiment, there is provided a method for altering the phenotype of a tumor cell comprising the step of contacting the cell with a tumor suppressor designated TS10q23.3 under conditions permitting the uptake of the tumor suppressor by the tumor cell. The tumor cell may be derived from a tissue such as brain, lung, liver, spleen, kidney, lymph node, small intestine, blood cells, pancreas, colon, stomach, breast, endometrium, prostate, testicle, ovary, skin, head and neck, esophagus, bone marrow and blood tissue. The phenotype may be selected from proliferation, migration, contact inhibition, soft agar growth or cell cycling. The tumor suppressor may be encapsulated in a liposome or free.

In another embodiment, there is provided a method for altering the phenotype of a tumor cell comprising the step of contacting the cell with a nucleic acid (i) encoding a tumor suppressor designated TS10q23.3 and (ii) a promoter active in the tumor cell, wherein the promoter is operably linked to the region encoding the tumor suppressor, under conditions permitting the uptake of the nucleic acid by the tumor cell. The phenotype may be proliferation, migration, contact inhibition, soft agar growth or cell cycling. The nucleic acid may be encapsulated in a liposome. If the nucleic acid is a viral vector such as retrovirus, adenovirus, adeno-associated virus, vaccinia virus and herpesvirus, it may be encapsulated in a viral particle.

In a further embodiment, there is provided a method for treating cancer comprising the step of contacting a tumor cell within a subject with a tumor suppressor designated TS10q23.3 under conditions permitting the uptake of the tumor suppressor by the tumor cell. The method may involve a human subject.

In still a further embodiment, there is provided a method for treating cancer comprising the step of contacting a tumor cell within a subject with a nucleic acid (i) encoding a tumor suppressor designated TS10q23.3 and (ii) a promoter active in the tumor cell, wherein the promoter is operably linked to the region encoding the tumor suppressor, under conditions permitting the uptake of the nucleic acid by the tumor cell. The subject may be a human.

In still yet a further embodiment, there is provided transgenic mammal in which both copies of the gene encoding TS10q23.3 are interrupted or replaced with another gene.

In an additional embodiment, there is provided a method of determining the stage of cancer comprising the steps of (i) obtaining a sample from a subject; and (ii) determining the expression a functional TS10q23.3 tumor suppressor in cells of the sample. The cancer may be a brain cancer and the stage is distinguished between low grade and glioma. The determining may comprise assaying for a TS10q23.3 nucleic acid or polypeptide in the sample.

In yet an additional example, there is provided a method of predicting tumor metastasis comprising the steps of (i) obtaining a sample from a subject; and (ii) determining the expression a functional TS10q23.3 tumor suppressor in cells of the sample. The cancer may be distinguished as metastatic and non-metastatic. The determining may comprise assaying for a TS10q23.3 nucleic acid or polypeptide in the sample.

In still yet an additional embodiment, there is provided a method of screening a candidate substance for anti-tumor activity comprising the steps of (i) providing a cell lacking functional TS10q23.3 polypeptide; (ii) contacting the cell with the candidate substance; and (iii) determining the effect of the candidate substance on the cell. The cell may be a tumor cell, for example, a tumor cell having a mutation in the coding region of TS10q23.3.7. The mutation may be a deletion mutant, an insertion mutant, a frameshift mutant, a nonsense mutant, a missense mutant or splice mutant. The determining may comprise comparing one or more characteristics of the cell in the presence of the candidate substance with characteristics of a cell in the absence of the candidate substance. The characteristic may be TS10q23.3 expression, phosphatase activity, proliferation, metastasis, contact inhibition, soft agar growth, cell cycle regulation, tumor formation, tumor progression and tissue invasion. The candidate substance may be a chemotherapeutic or radiotherapeutic agent or be selected from a small molecule library. The cell may be contacted in vitro or in vivo.

In still a further additional embodiment, there is provided a method of screening a candidate substance for anti-kinase activity comprising the steps of (i) providing a having TS10q23.3 polypeptide comprising at least one tyrosine kinase site; (ii) contacting the cell with the candidate substance; and (iii) determining the effect of the candidate substance on the phosphorylation of the site. The determining may comprise comparing one or more characteristics of the cell in the presence of the candidate substance with characteristics of a cell in the absence of the candidate substance. The characteristic may be phosphorylation status of TS10q23.3, TS10q23.3 expression, phosphatase activity, proliferation, metastasis, contact inhibition, soft agar growth, cell cycle regulation, tumor formation, tumor progression and tissue invasion. The candidate substance may be a chemotherapeutic or radiotherapeutic agent or be selected from a small molecule library. The cell may be contacted in vitro or in vivo.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIGS. 6A and 6B—Coding Sequence and 5'- and 3'-Flanking Regions of TS10q23.3. Coding region is in bold as is the first in frame stop codon.

FIG. 7—Predicted Amino Acid Sequence of TS10q23.3 Product. Abbreviations are A, alanine; C, cysteine; D, aspartic acid; E, glutamic acid; F; phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine. Phosphatase consensus site is in bold; tyrosine phosphorylation sites are italicized and underlined.

Figure 9A:
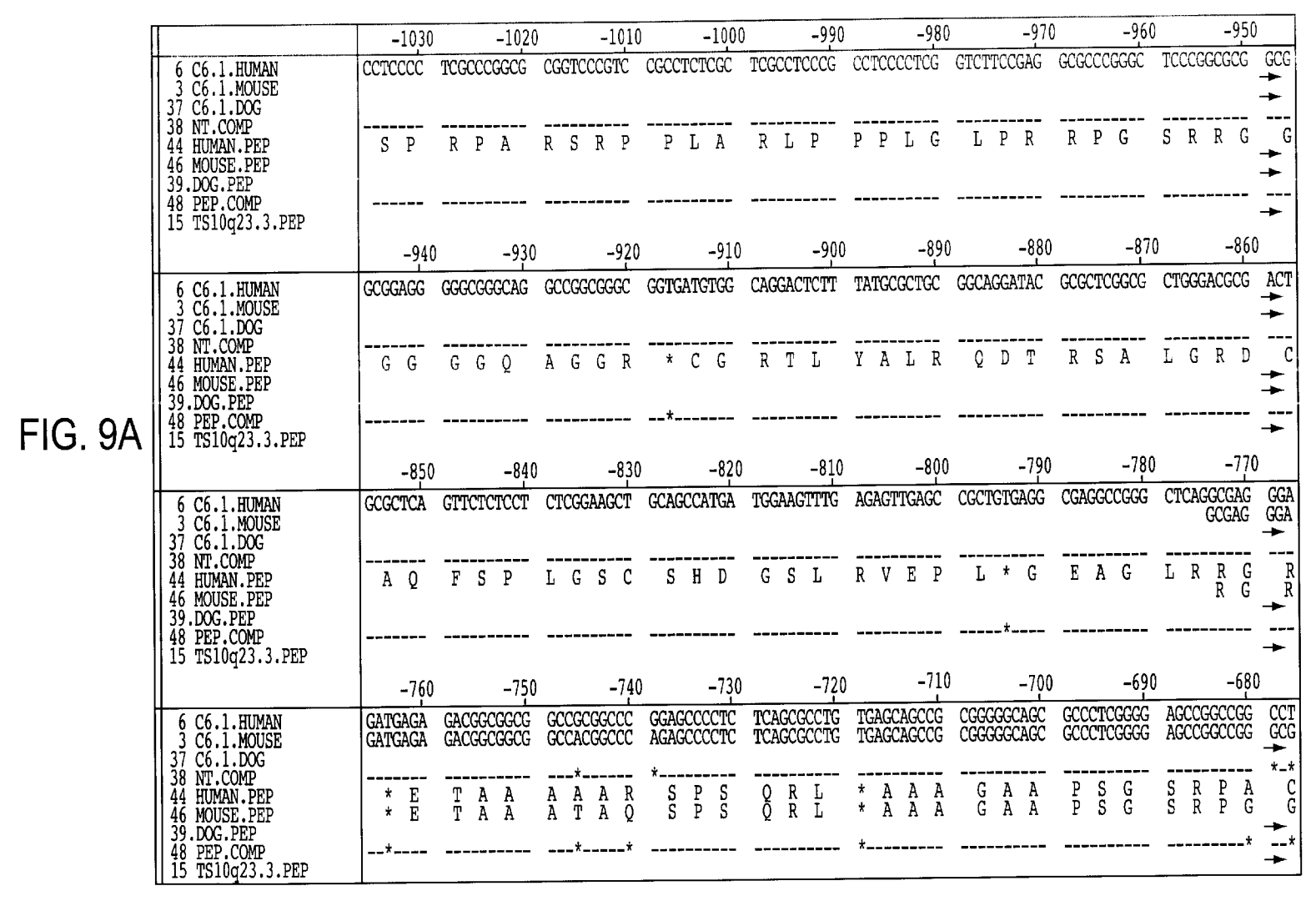
Figure 9B:
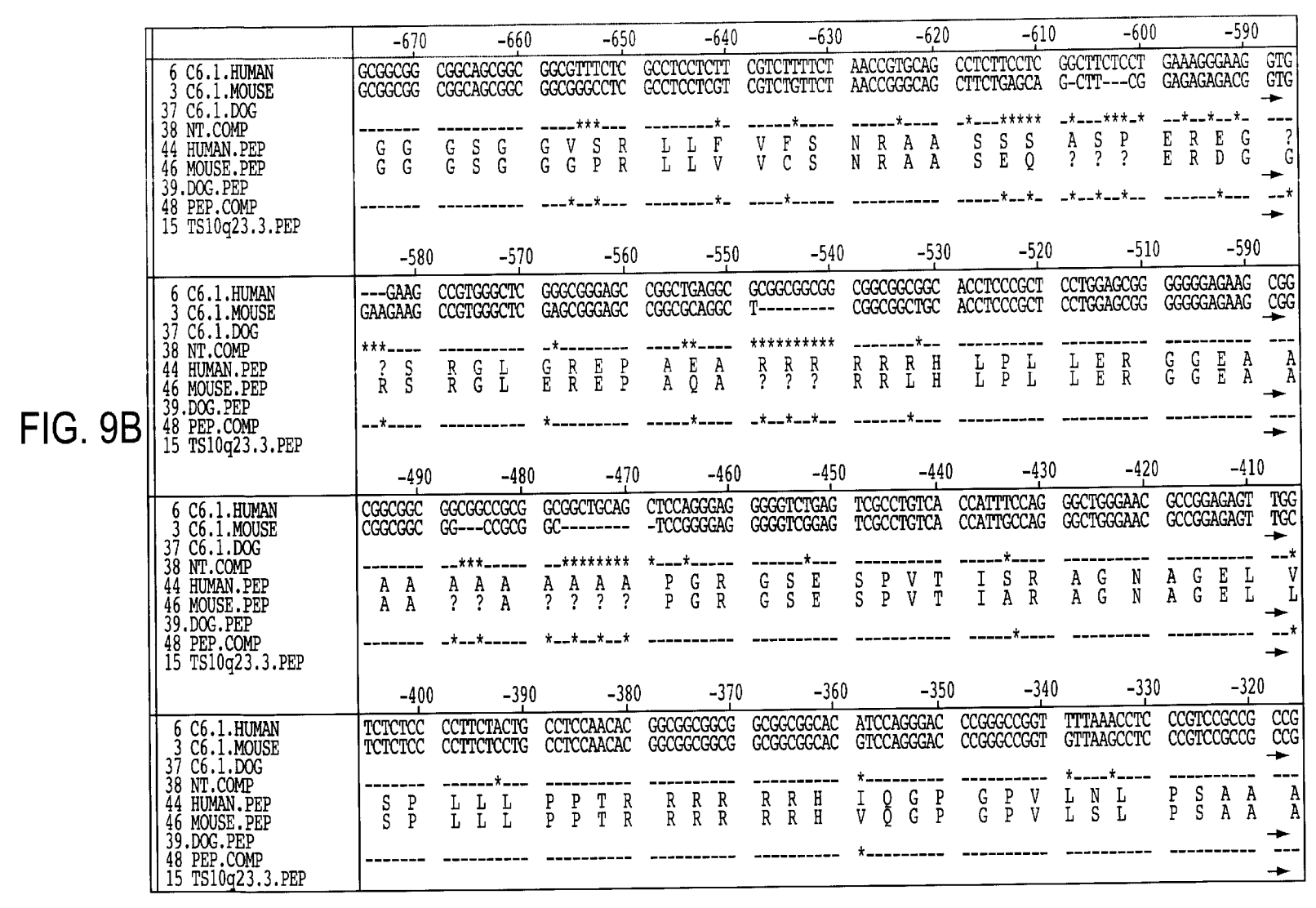
Figure 9C:
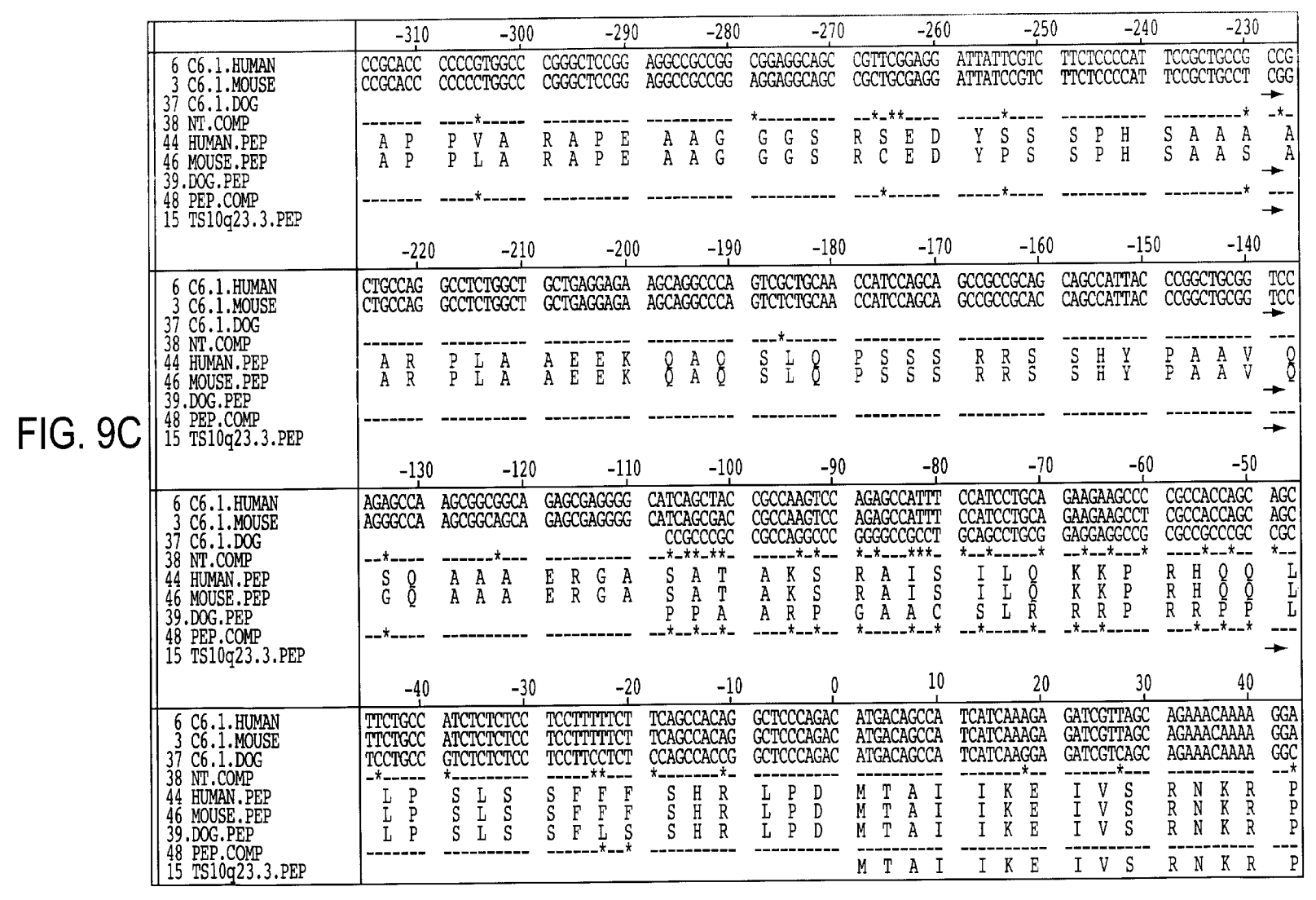
Figure 9D:
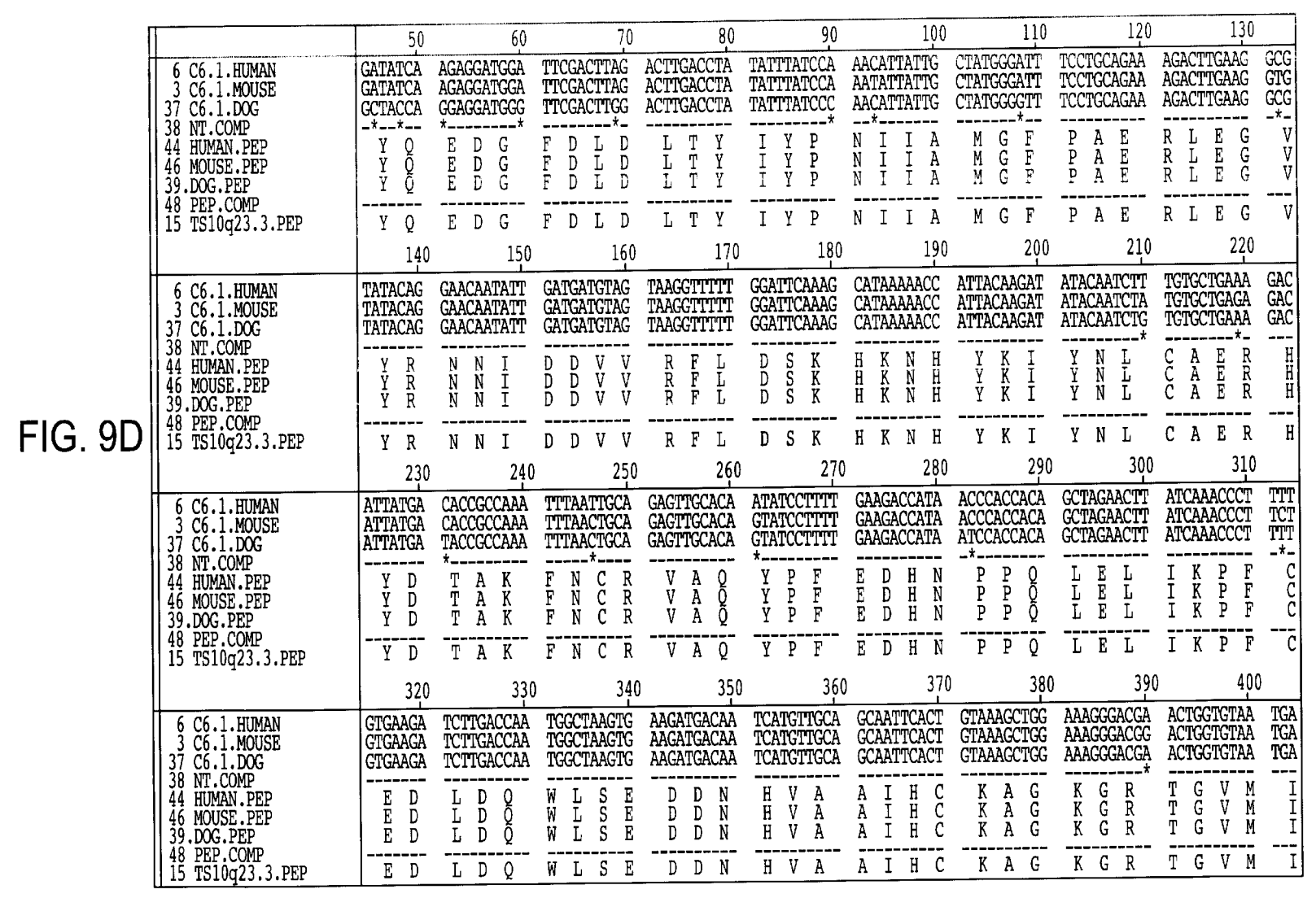
Figure 9E:
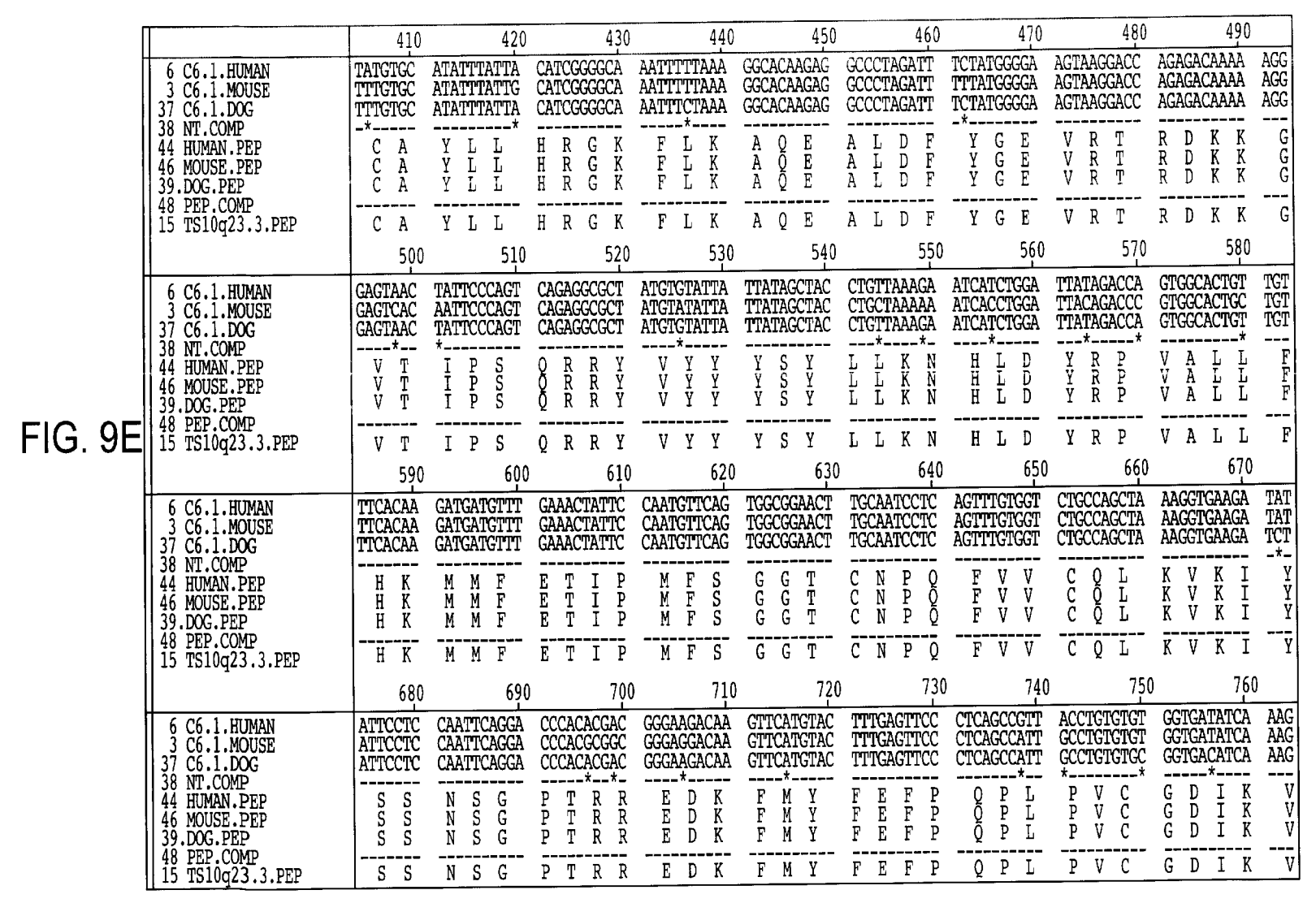
Figure 9F:
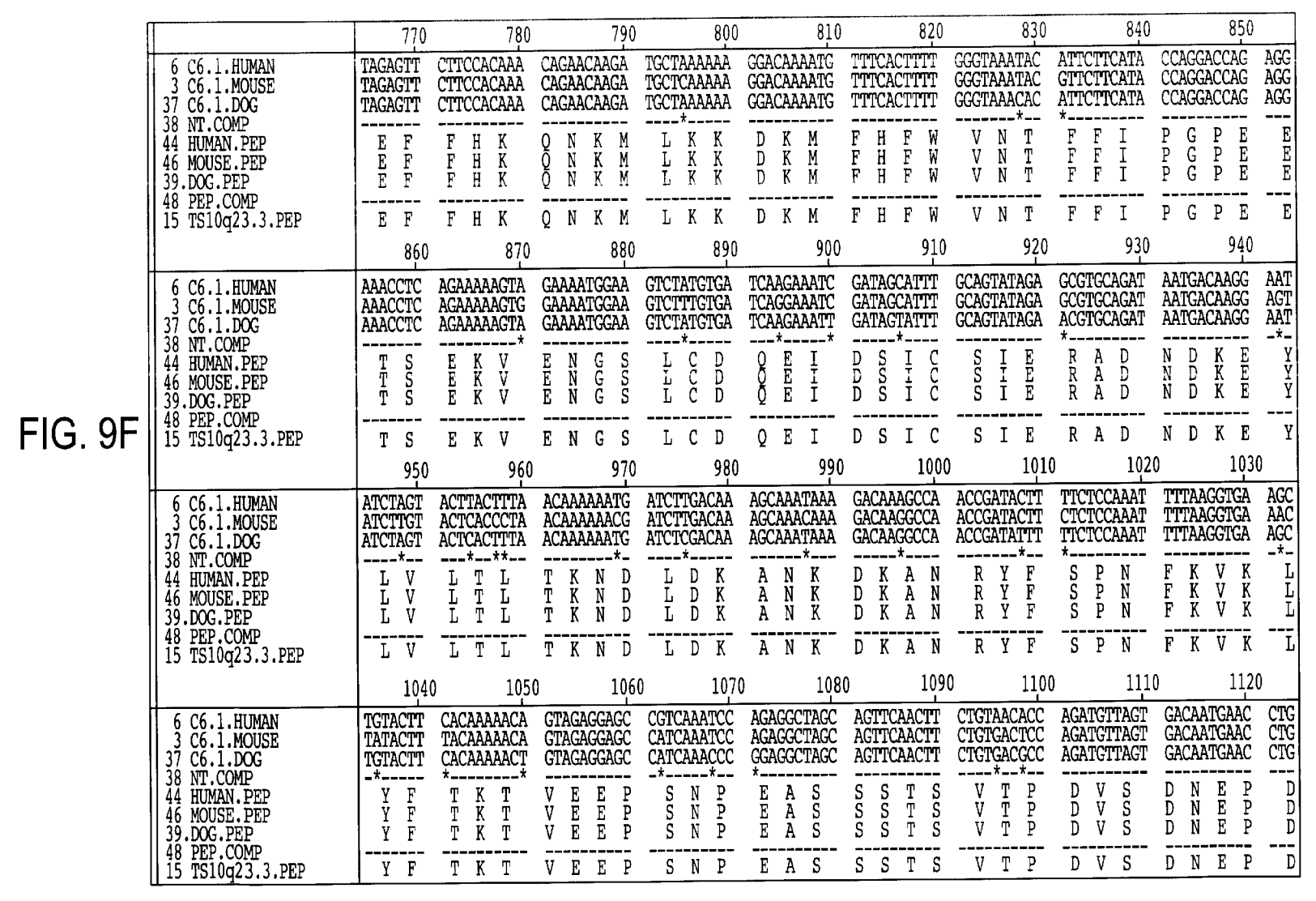

FIGS. 9A–9I—Homology Comparison of Human TS10q23.3 with Mouse and Dog Homologs. The initiation ATG codon and methionine amino acid are designated at the start (1) position. The termination codon is TGA (1210). Alterations between the human and mouse or dog sequences on the genomic or amino acid level are designated by a star in the sequence compared. However, no changes in the amino acid sequence were observed.

Figure 10B:
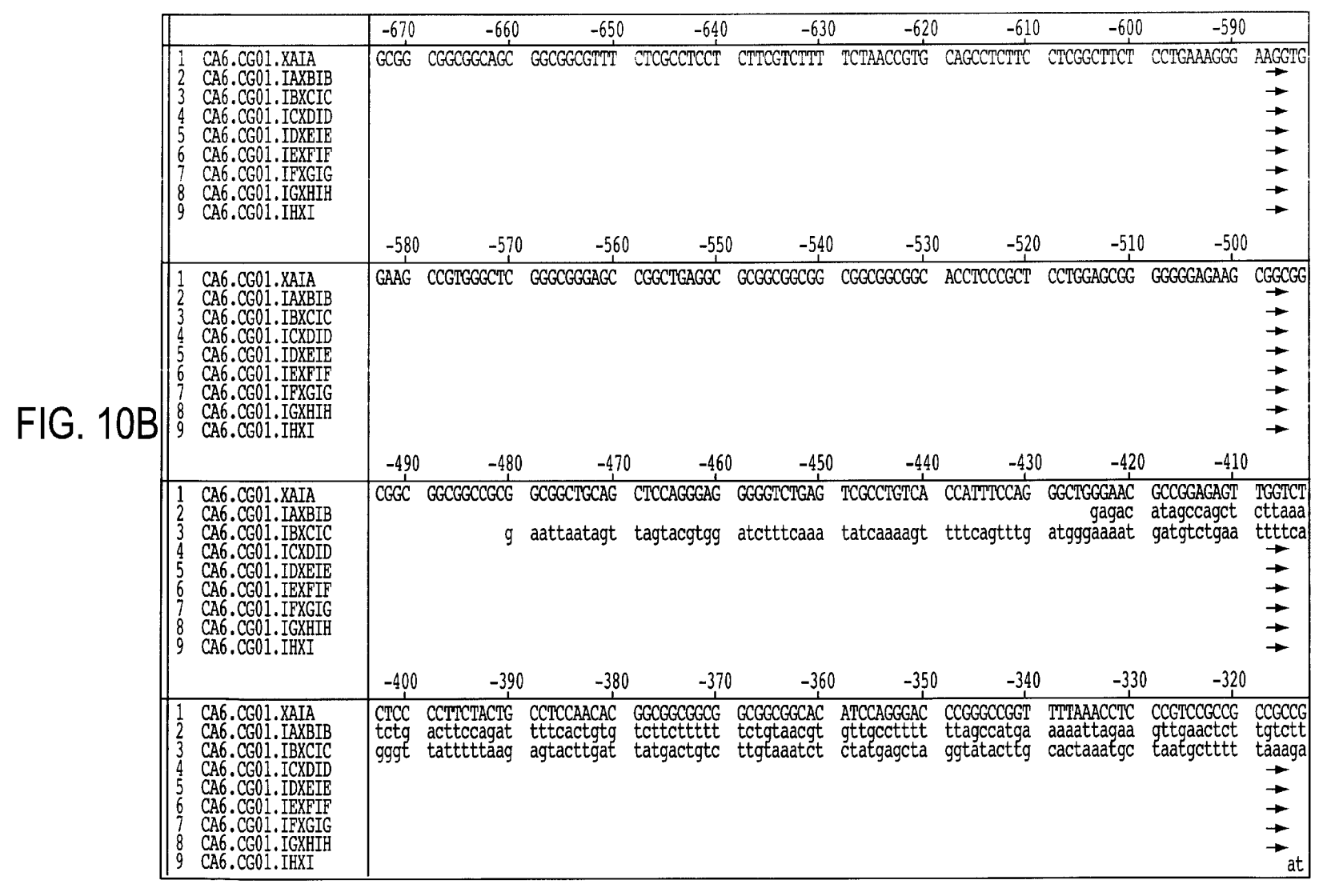
Figure 10C:
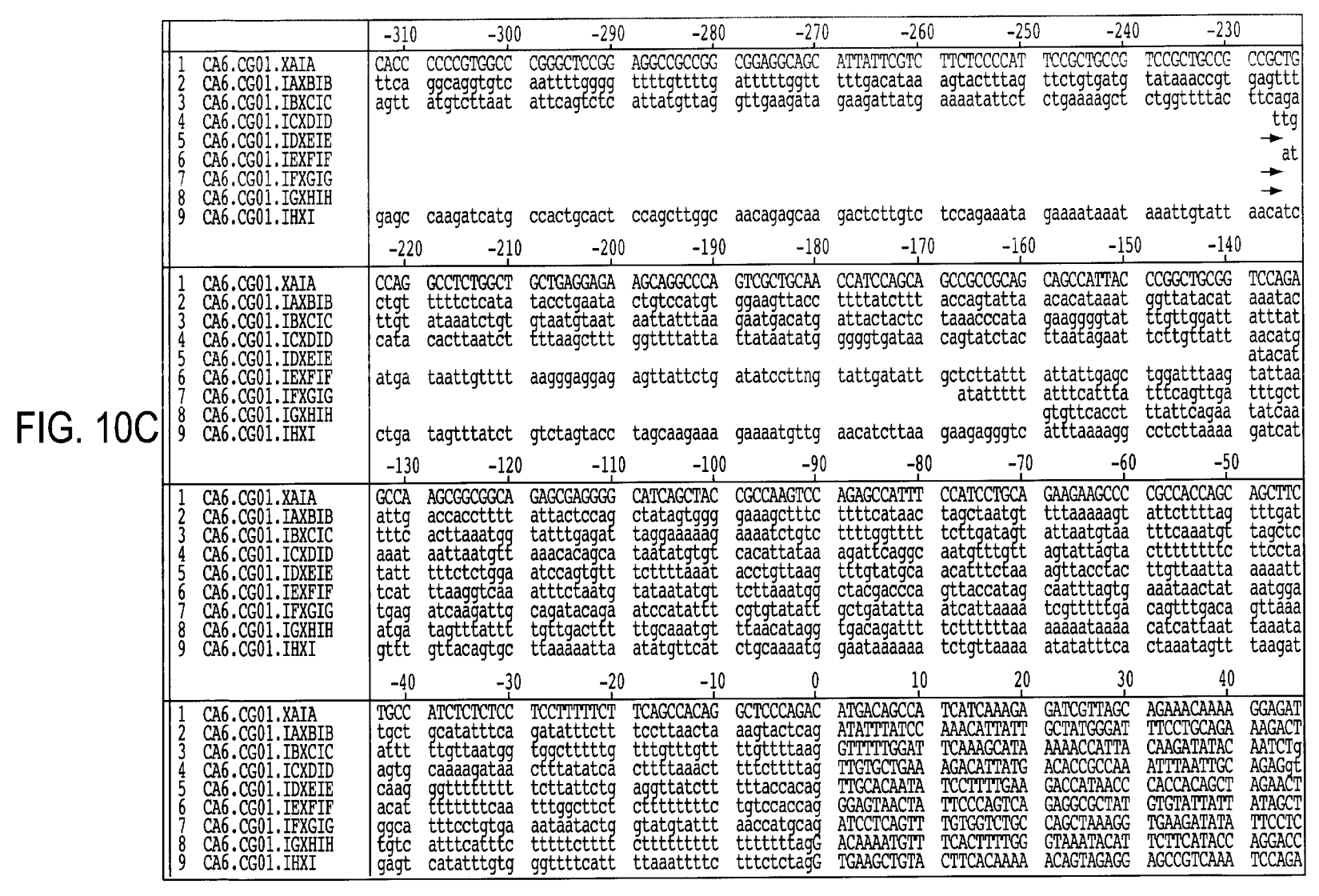
Figure 10D:
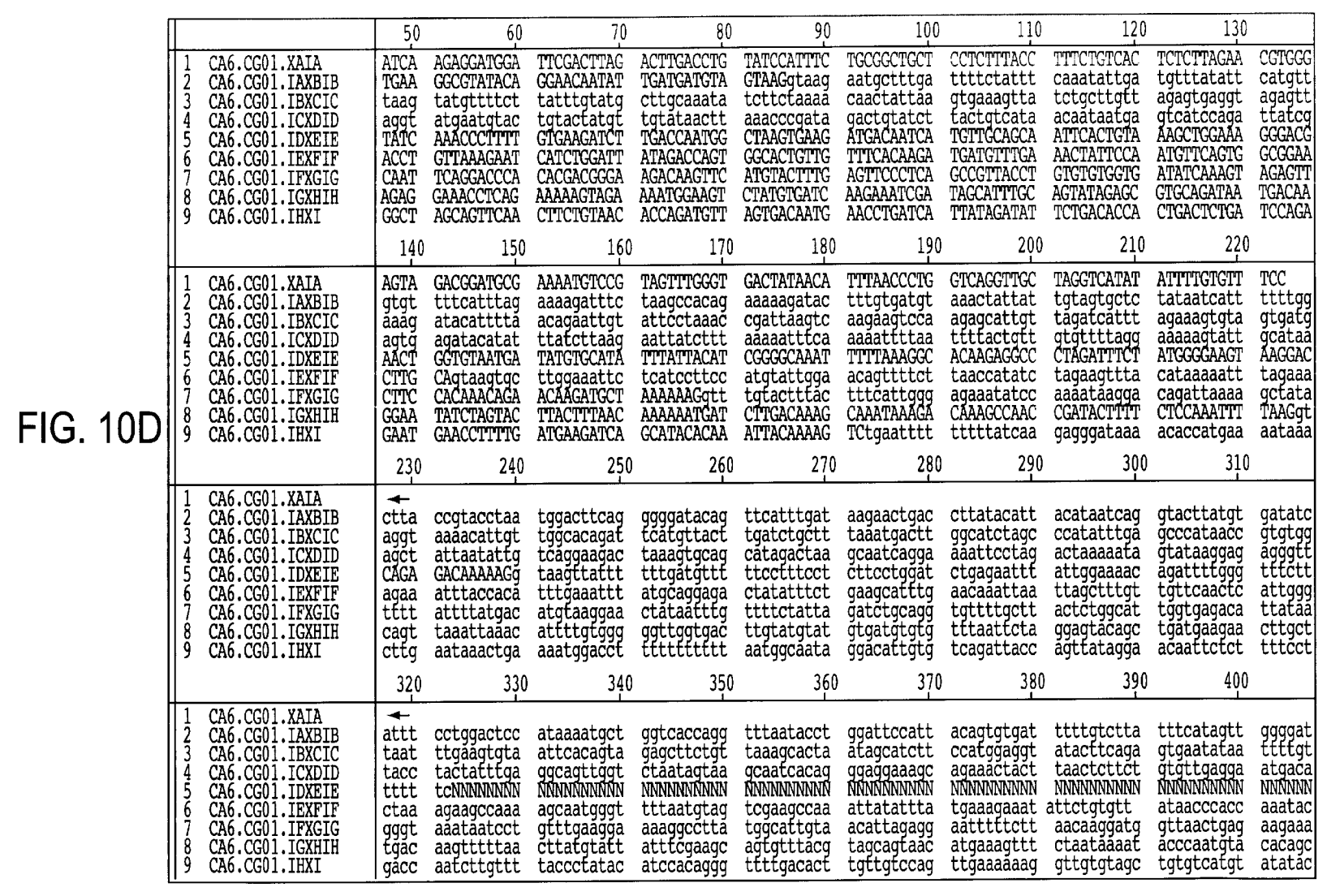

FIGS. 10A–10E—Sequence of Exons and Surrounding Intronic Regions of TS10q23.3. The exons are denoted as capital letters starting at position one, and introns are designated lower case letters; except for the first exon where the initiation codon starts at position one and the 3' exon/intron boundary is at position 79 and 80, respectively. The lower case letter designate (Table 4) corresponds to the numbering of the sequence presented in these figures, except for the first exon. The mutations for U87 and U138 are at the first intron G residue [G+1>T] after the exon (G and H, respectively). For T98G and KE, the point mutations are at positions 46 and 28 of exon B, respectively. For LnCap cells, the mutation is a deletion of bases 16 and 17 in the first intron.

FIGS. 11A–G—Analysis of Secondary Structures in TS1023.3. FIG. 11A: Hydrophilicity plot; FIG. 11B: Surface probability plot; FIG. 11C: Flexibility plot; FIG. 11D: Antigenic index plot; FIG. 11E: Amphiphilic helix plot; FIG. 11F: Amphiphilic sheet plot; FIG. 11G: Secondary structure plot.

FIGS. 12A–I—Comparison of Predicted Characteristics in TS10q23.3 and Point Mutants T98G and KE. FIG. 12A: Hydrophilicity plot of residues 1–60 of wild-type polypeptide; FIG. 12B: Surface probability plot of residues 1–60 of wild-type polypeptide; FIG. 12C: Secondary structure plot of residues 1–60 of wild-type polypeptide; FIG. 12D: Hydrophilicity plot of residues 1–60 of KE mutant; FIG. 12E: Surface probability plot of residues 1–60 of KE mutant; FIG. 12F: Secondary structure plot of residues 1–60 of KE mutant; FIG. 12G: Hydrophilicity plot of residues 1–60 of T98G mutant; FIG. 12H: Surface probability plot of residues 1–60 of T98G mutant; FIG. 12I: Secondary structure plot of residues 1–60 of T98G mutant. The T98G mutation (Leu→Arg) at residue 42 results in the loss of proposed helix secondary structure of TS10q23.3. The mutation in KE at residue 36 (Gly→Glu) would significantly increase the length of the proposed helical structure in the region. Both mutations would affect the same helical structure. Also, minor changes in the hydrophilicity and surface probability arise.

SEQUENCE SUMMARY

Figure 1:
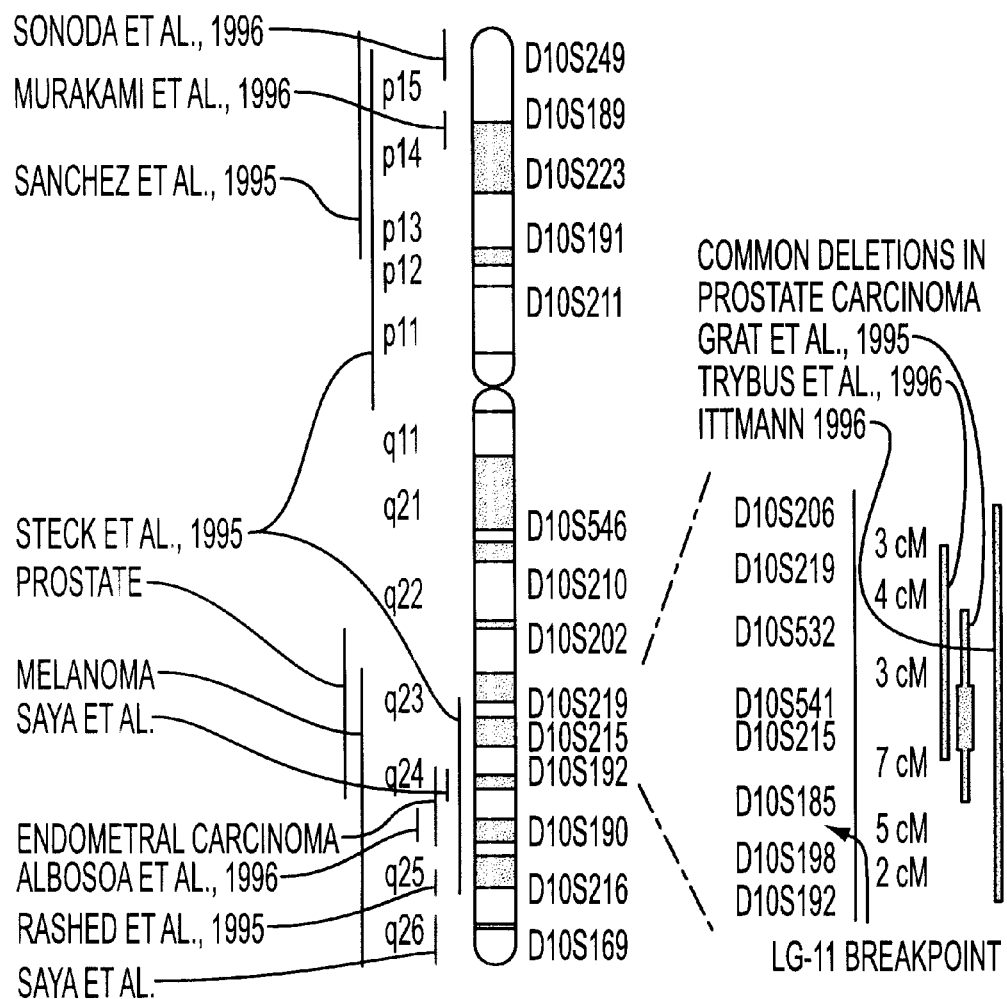
FIG. 1—Localization of Candidate Tumor Suppressor Loci on Human Chromosome 10. Various loci on the human chromosome 10 have been implicated as possible sites for tumor suppressing activity. These locations, and the reporting group, are depicted.

SEQ ID NO:1=predicted sequence for TS10Q23.3; SEQ ID NO:2=human gene sequence; SEQ ID NO:3=mouse gene sequence; SEQ ID NO:4=dog gene sequence; SEQ ID NO:5=human peptide sequence; SEQ ID NO:6=mouse peptide sequence; SEQ ID NO:7=dog peptide sequence; SEQ ID NO:8=exon a; SEQ ID NO:9=exon b; SEQ ID NO:10=exon c; SEQ ID NO:11=exon d; SEQ ID NO:12=exon e; SEQ ID NO:13=exon f; SEQ ID NO:14=exon g; SEQ ID NO:15=exon h; SEQ ID NO 16=exon I; SEQ ID NO:17=a motif from residues 88 to 98; SEQ ID NO:18=conserved catalytic domain of a protein tyrosine phosphatase (Denu et al., 1996); SEQ ID NO:19 residues 1–60 of wild-type TS10q23.3 polypeptide; SEQ ID NO:20 residues 1–60 of T98G mutant TS 10q23.3 polypeptide; SEQ ID NO:21 residues 1–60 of KE mutant TS10q23.3 polypeptide.

DETAILED DESCRIPTION OF THE PREFERRED EMBODIMENTS

I. The Present Invention

As stated above, a number of different groups have shown evidence of a tumor suppressing activity associated with the 10q region of human chromosome 10. Despite this considerable amount of work, the identity of the gene or genes responsible for this activity has not been determined. Previous used a functional approach involving transfer of chromosomes or chromosomal fragments suspected of harboring tumor suppressor gene(s) into tumorigenic glioma cells. These efforts allowed definition of the biological activity of putative tumor suppressor gene(s) and aid in the localization of such. Chromosomes 2 and 10 were transferred into U251 glioma cells and chromosomes 2 and 10 into LG-11 cells. The LG-11 cells were shown to have no intact copies of chromosome 10 and the breakpoint was subsequently found to occur at 10q24. The transfer of chromosome 10 resulted in hybrid cells that displayed a suppressed phenotype, exhibiting a loss of tumorigenicity (no tumor formation) and loss of the ability to grow in soft agarose (50× to 1000× decrease; Pershouse et al., 1993). The hybrid's exponential growth rate was similar to the parental cell, although the hybrid cell's saturation density was significantly (10× to 20×) lower than the parental cells. The transfer of chromosome 2 resulted in hybrid cells that acted similar to the parental cells.

One objective of these studies was to localize the chromosome 10 suppressor gene by fragmentation of the neomycin-tagged chromosome 10 and, subsequently, to transfer the fragmented chromosome into glioma cells. However, the inventors observed that some of the hybrid cells had spontaneously undergone chromosomal rearrangements to yield hybrid cells retaining only various regions of the inserted chromosome 10 (Pershouse et al., 1993). The inventors then subcloned the hybrids and analyzed them, rather than initiate fragmentation studies (Steck et al., 1995). The retention of the inserted chromosome 10 or its fragments was tracked by informative RFLP markers and FISH analysis. Interestingly, only the inserted chromosome was subjected to rearrangement. The insertion of an entire copy of chromosome 10 resulted in inhibition of the hybrid cell's transformed property to proliferate in soft agarose and to form tumors in nude mice.

These two phenotypes now appear to be partially separable by the instant analysis. Some subclones (U251.N10.5a–j), which revealed a loss of a major portion of the long arm of chromosome 10, grew in soft agarose but failed to form tumors in nude mice, thus indicating that a tumor suppressive locus resides in the remaining portion of the chromosome (10pter to 10q11). In contrast, clones that retained a distal region of the long arm, 10q24 to 10q26, failed both to proliferate in soft agarose and in nude mice (see FIG. 4). This suggests another phenotypic suppressive region residing in the distal region of the chromosome. The lack of additional 10-associated material further would suggest that the remaining chromosome 10 material is responsible for the altered biological phenotype. These results implicate the presence of two phenotypically independent suppressive regions on chromosome 10 involved in glioma progression (Steck et al., 1995).

According to the present invention, the inventors now have used several independent strategies to localize a tumor suppressor gene, designated TS10q23.3, that is involved in gliomas, breast cancer, prostate cancer and other cancers. These approaches, described in greater detail in the following Examples, included (i) identification of homozygous deletions in a series of human glioma cell lines; (ii) determination of a consistent region(s) of retention in clones suppressed for tumorigenicity; and (iii) allelic deletion studies on various grades of glioma and corresponding normal samples. With the gene in hand, it now becomes possible to exploit the information encoded by the gene to develop novel diagnostic and therapeutic approaches related to human cancer.

II. The 10q23.3 Tumor Suppressor

According to the present invention, there has been identified a tumor suppressor, encoded by a gene in the 10q23.3 locus, and designated here as TS10q23.3. This molecule is capable of suppressing tumor phenotypes in various cancers. The term tumor suppressor is well-known to those of skill in the art. Examples of other tumors suppressors are p53, Rb and p16, to name a few. While these molecules are structurally distinct, they form group of functionally-related molecules, of which TS10q23.3 is a member. The uses for which these other tumor suppressors now are being exploited are equally applicable here.

In addition to the entire TS10q23.3 molecule, the present invention also relates to fragments of the polypeptide that may or may not retain the tumor suppressing (or other) activity. Fragments including the N-terminus of the molecule may be generated by genetic engineering of translation stop sites within the coding region (discussed below). Alternatively, treatment of the TS10q23.3 molecule with proteolytic enzymes, known as protease, can produces a variety of N-terminal, C-terminal and internal fragments. Examples of fragments may include contiguous residues of the TS10q23.3. sequence given in FIG. 7 and FIG. 9, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including inunnunoaffinity chromatography) or various size separations (sedimentation, gel electrophoresis, gel filtration).

A. Structural Features of the Polypeptide

The gene for TS10q23.3 encodes a 403 amino acid polypeptide. The predicted molecular weight of this molecule is 47,122, with a resulting pI of 5.86. Thus, at a minimum, this molecule may be used as a standard in assays where molecule weight and pI are being examined.

A phosphatase consensus site located at residues 122–131, matching perfectly the tyrosine phosphatase (PTP) consensus sequence: [I/V]HCxAGxxR[S/T]G (SEQ ID NO:22). Outside the active domains, sequences differ greatly. PTPs proceed through phosphoenzyme intermediates. The enzymatic reaction involves phosphoryl-cysteine intermediate formation after nucleophilic attack of the phosphorus atom of the substrate by the thiolate anion of cysteine. The reaction can be represented as a two-step chemical process: phosphoryl transfer to the enzyme accompanied by rapid release of dephosphorylated product; and hydrolysis of the thiol-phosphate intermediate concomitant with rapid release of phosphate. To form the catalytically competent component complex, the enzyme binds and reacts with the dianion of phosphate-containing substrate. On the enzyme, an aspartic acid must be protonated and the nucleophilic cysteine must be unprotonated (thiolate anion) for phosphoryl transfer to the enzyme. Also of note are potential tyrosine phosphorylation sites located at residues 233–240 and 308–315 and cAMP phosphorylation sites located at residues 128, 164, 223 and 335. Phosphatases are known to have kinase sites, and the phosphatase activity of these enzymes can be modulated by phosphorylation at these sites. Protein phosphatases generally are divided into two categories—serine/threonine phosphatases and tyrosine phosphatases. Certain of the tyrosine phosphatases also have activity against phosphoserine and phosphothreonine.

The interaction between kinases and phophatases, and the various phosphorylation states of polypeptides, have been demonstrated as important features in cell physiology. Through a variety of different mechanisms, kinases and phophatases act in different pathways within cells that are involved in signaling, energy storage and cell regulation. Since the identification of an intrinsic tyrosine kinase function in the transforming protein src (Collett & Erickson, 1978), the role of phosphorylation, particularly on tyrosine residues, has been demonstrated to play a critical role in the control of cellular proliferation and the induction of cancer (Hunter, 1991; Bishop, 1991). The roles that protein phosphatases play in growth regulation, as well as in many other biological and biochemical activities, has been correlated with the phosphrylation state of biologically important molecules (Cohen, 1994).

It also should be mentioned that the 60 or so amino acids of the N-terminus of the molecule show some homology to tensin, a cytoskeletal protein implicated in adhesion plaques. This suggest that TS10q23.3 maybe involved cell surface phenomena such as contact inhibition, invasion, migration or cell-to-cell signaling. TS10q23.3 point mutations identified in certain tumor cell lines affect secondary proposed structures in this region.

B. Functional Aspects

When the present application refers to the function of TS10q23.3 or "wild-type" activity, it is meant that the molecule in question has the ability to inhibit the transformation of cell from a normally regulated state of proliferation to a malignant state, ie., one associated with any sort of abnormal growth regulation, or to inhibit the transformation of a cell from an abnormal state to a highly malignant state, e.g., to prevent metastasis or invasive tumor growth. Other phenotypes that may be considered to be regulated by the normal TS10q23.3 gene product are angiogenesis, adhension, migration, cell-to-cell signaling, cell growth, cell proliferation, density-dependent growth, anchorage-dependent growth and others. Determination of which molecules possess this activity may be determined using assays familiar to those of skill in the art. For example, transfer of genes encoding TS10q23.3, or variants thereof, into cells that do not have a functional TS10q23.3 product, and hence exhibit impaired growth control, will identify, by virtue of growth suppression, those molecules having TS10q23.3 function.

As stated above, there is an indication that TS10q23.3 is a phosphatase. The portion of the protein located at residues 88 to 98 is a perfect match for the conserved catalytic domain of protein tyrosine phosphatase. Also, putative kinase targets are located in the molecule, which is another characteristic of phosphatases. Because other tumor suppressors have been identified with this sort of activity, it will be desirable to determine the phosphatase function in the tumor suppressing role of TS10q23.3. This also may be a fruitful approach to developing screening assays for the absence of TS10q23.3 function or in the development of cancer therapies, for example, in targeting the phosphatase function of TS10q23.3, targeting the substrate upon which TS10q23.2 acts, and/or targeting the kinase or kinases which act upon TS10q23.3.

C. Variants of TS10q23.3

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability agannst proteolytic cleavage, without the loss of other functions or properties Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutanate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of TS10q23.3, but with altered and even improved characteristics.

D. Domain Switching

As described in the examples, the present inventors have identified putative murine and canine homologs of the human TS10q23.3 gene. In addition, mutations have been identified in TS10q23.3 which are believed to alter its function. These studies are important for at least two reasons. First, they provides a reasonable expectation that still other homologs, allelic variants and mutants of this gene may exist in related species, such as rat, rabbit, monkey, gibbon, chimp, ape, baboon, cow, pig, horse, sheep and cat. Upon isolation of these homologs, variants and mutants, and in conjunction with other analyses, certain active or functional domains can be identified. Second, this will provide a starting point for further mutational analysis of the molecule. One way in which this information can be exploited is in "domain switching."

Domain switching involves the generation of chimeric molecules using different but, in this case, related polypeptides. By comparing the mouse, dog and human sequences for TS10q23.3 with the TS10q23.3 of other species, and with mutants and allelic variants of these polypeptides, one can make predictions as to the functionally significant regions of these molecules. It is possible, then, to switch related domains of these molecules in an effort to determine the criticality of these regions to TS10q23.3 function. These molecules may have additional value in that these "chimeras" can be distinguished from natural molecules, while possibly providing the same function.

Based on the sequence identity, at the amino acid level, of the mouse, dog and human sequences, it may be inferred that even small changes in the primary sequence of the molecule will affect function. Further analysis of mutations and their predicted effect on secondary structure will add to this understanding.

Another structural aspect of TS10q23.3 that provides fertile ground for domain switching experiments is the tyrosine phosphatase-like domain and the putative tyrosine phosphorylation sites. This domain may be substituted for other phosphatase domains in order to alter the specificity of this function. A further investigation of the homology between TS10q23.3 and other phosphatases is warranted by this observation.

E. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. One particular fusion of interest would include a deletion construct lacking the phosphatase site of TS10q23.3 but containing other regions that could bind the substrate molecule. Fusion to a polypeptide that can be used for purification of the substrate-TS10q23.3 complex would serve to isolated the substrate for identification and analysis.

F. Purification of Proteins

It will be desirable to purify TS10q23.3 or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

G. Synthetic Peptides

The present invention also describes smaller TS10q23.3-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et a., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformned or transfected into an appropriate host cell and cultivated under conditions suitable for expression.

H. Antigen Compositions

The present invention also provides for the use of TS10q23.3 proteins or peptides as antigens for the immunization of animals relating to the production of antibodies. It is envisioned that either TS10q23.3, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

The present invention also provides, in another embodiment, genes encoding TS10q23.3. Genes for the human, canine and murine TS10q23.3 molecule have been identified. The present invention is not limited in scope to these genes, however, as one of ordinary skill in the could, using these two nucleic acids, readily identify related homologs in various other species (e.g., rat, rabbit, monkey, gibbon, chimp, ape, baboon, cow, pig, horse, sheep, cat and other species). The finding of mouse and dog homologs for this gene makes it likely that other species more closely related to humans will, in fact, have a homolog as well.

In addition, it should be clear that the present invention is not limited to the specific nucleic acids disclosed herein. As discussed below, a "TS10q23.3 gene" may contain a variety of different bases and yet still produce a corresponding polypeptides that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of TS10q23.3.

A. Nucleic Acids Encoding 10q23.3

The human gene disclosed in FIGS. 6 and 9, and the murine gene disclosed in FIG. 9 are TS10q23.3 genes of the present invention. Nucleic acids according to the present invention may encode an entire TS10q23.3 gene, a domain of TS10q23.3 that expresses a tumor suppressing or phosphatase function, or any other fragment of the TS10q23.3 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a mimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given TS10q23.3 from a given species may be represented by natural variants that have slightly different nucleic acid sequences but, nonetheless, encode the same protein (see Table 1 below).

As used in this application, the term "a nucleic acid encoding a TS10q23.3" refers to a nucleic acid molecule that has been isolated free of total cellular nucleic acid. In preferred embodiments, the invention concerns a nucleic acid sequence essentially as set forth in FIGS. 6 and 9. The term "as set forth in FIG. 6 or 9" means that the nucleic acid sequence substantially corresponds to a portion of FIG. 6 or 9. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | J | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of FIG. 9 will be sequences that are "as set forth in FIG. 9." Sequences that are essentially the same as those set forth in FIG. 9 may also be functionally defined as sequences that are capable of hybridizing to a nucleic acid segment containing the complement of FIG. 9 under standard conditions.

The DNA segments of the present invention include those encoding biologically functional equivalent TS10q23.3 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in FIGS. 6 and 9. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of FIGS. 6 and 9 under relatively stringent conditions such as those described herein. Such sequences may encode the entire TS10q23.3 protein or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. it is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 3431 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

One method of using probes and primers of the present invention is in the search for genes related to TS10q23.3 or, more particularly, homologs of TS10q23.3 from other species. The existence of a murine homolog strongly suggests that other homologs of the human TS10q23.3 will be discovered in species more closely related, and perhaps more remote, than mouse. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of TS10q23.3 in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al, 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express the TS10q23.3 polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene, Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
|---|
| Immunoglobulin Heavy Chain |
| Immunoglobulin Light Chain |
| T-Cell Receptor |
| HLA DQα and DQβ |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serun Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
|---|---|
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |

TABLE 3-continued

| Element | Inducer |
| --- | --- |
| Tumor Necrosis Factor | FMA |
| Thyroid Stimulating Hormone α Gene | Thyroid Hormone |
| Insulin E Box | Glucose |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al, 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltansferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successfil. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

III. Generating Antibodies Reactive With TS10q23.3

In another aspect, the present invention contemplates an antibody that is immunoreactive with a TS10q23.3 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in inmmunohistochemical procedures such as tissue staining, as well as in other procedures which may utilize antibodies specific to TS10q23.3-related antigen epitopes. Additionally, it is proposed that monoclonal antibodies specific to the particular TS10q23.3 of different species may be utilized in other useful applications In general, both polyclonal and monoclonal antibodies against TS10q23.3 may be used in a variety of embodiments. For example, they may be employed in antibody cloning protocols to obtain cDNAs or genes encoding other TS10q23.3. They may also be used in inhibition studies to analyze the effects of TS10q23.3 related peptides in cells or animals. Anti-TS10q23.3 antibodies will also be useful in immunolocalization studies to analyze the distribution of TS10q23.3 during various cellular events, for example, to determine the cellular or tissue-specific distribution of TS10q23.3 polypeptides under different points in the cell cycle. A particularly useful application of such antibodies is in purifying native or recombinant TS10q23.3, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the inimunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected irnmunogen composition, e.g., a purified or partially purified TS10q23.3 protein, polypeptide or peptide or cell expressing high levels of TS10q23.3. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mabs produced by either means may be further purified, if desired, using filtration, centrifugation and various chromatographic methods such as HPLC or affinity chromatography.

IV. Diagnosing Cancers Involving TS10q23.3

The present inventors have determined that alterations in TS10q23.3 are associated with malignancy. Therefore, TS10q23.3 and the corresponding gene may be employed as a diagnostic or prognostic indicator of cancer. More specifically, point mutations, deletions, insertions or regulatory pertubations relating to TS10q23.3 may cause cancer or promote cancer development, cause or promoter tumor progression at a primary site, and/or cause or promote metastasis. Other phenomena associated with malignancy that may be affected by TS10q23.3 expression include angiogenesis and tissue invasion.

A. Genetic Diagnosis

One embodiment of the instant invention comprises a method for detecting variation in the expression of TS10q23.3. This may comprises determining that level of TS10q23.3 or determining specific alterations in the expressed product. Obviously, this sort of assay has importance in the diagnosis of related cancers. Such cancer may involve cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the diagnosis of gliomas.

The biological sample can be any tissue or fluid. Various emb odiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have TS10q23.3-related pathologies. In this way, it is possible to correlate the amount or kind of TS10q23.3 detected with various clinical states.

Various types of defects are to be identified. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of TS10q23.3 produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used. Using the sequences disclosed herein, oligonucleotide primers may be designed to permit the amplification of sequences throughout the TS10q23.3 gene that may then be analyzed by direct sequencing.

(vi) Kit Components

All the essential materials and reagents required for detecting and sequencing TS10q23.3 and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from patients. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with. an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

B. Immunodiagnosis

Antibodies of the present invention can be used in characterizing the TS10q23.3 content of healthy and diseased tissues, through techniques such as ELISAs and Western blotting. This may provide a screen for the presence or absence of malignancy or as a predictor of future cancer.

The use of antibodies of the present invention, in an ELISA assay is contemplated. For example, anti-TS10q23.3 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for TS10q23.3 that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. Methods for Screening Active Compounds

The present invention also contemplates the use of TS10q23.3 and active fragments, and nucleic acids coding therefor, in the screening of compounds for activity in either stimulating TS10q23.3 activity, overcoming the lack of TS10q23.3 or blocking the effect of a mutant TS10q23.3 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, anti-phosphatase activity, phosphorylation of TS10q23.3, dephosphorylation of TS10q23.3, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

A. In Vitro Assays

In one embodiment, the invention is to be applied for the screening of compounds that bind to the TS10q23.3 molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of TS10q23.3 to a natural or artificial substrate or binding partner. Competitive binding assays can be performed in which one of the agents (TS10q23.3, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with TS10q23.3 and washed. Bound polypeptide is detected by various methods.

Purified TS10q23.3 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the TS10q23.3 active region to a solid phase.

Various cell lines containing wild-type or natural or engineered mutations in TS10q23.3 can be used to study various functional attributes of TS10q23.3 and how a candidate compound affects these attributes. Methods for engineering mutations are described elsewhere in this document, as are naturaly-occurring mutations in TS10q23.3 that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of TS10q23.3, or related pathways, may be explored. This may involve assays such as those for protein expression, enzyme function, substrate utilization, phosphorylation states of various molecules including TS10q23.3, cAMP levels, mRNA expression (including differential display of whole cell or polyA RNA) and others.

B. In Vivo Assays

The present invention also encompasses the use of various animal models. Here, the identity seen between human and mouse TS10q23.3 provides an excellent opportunity to examine the function of TS10q23.3 in a whole animal system where it is normally expressed. By developing or isolating mutant cells lines that fail to express normal TS10q23.3, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type TS10q23.3 may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for TS10q23.3 or a fragment thereof. This could be accomplished by x-ray crystallograph, computer modeling or by a combination of both approaches. An alternative approach, "alanine scan," involves the random replacement of residues throughout molecule with alanine, and the resulting affect on function determined.

It also is possible to isolate a TS10q23.3 specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved TS10q23.3 activity or which act as stimulators, inhibitors, agonists, antagonists or TS10q23.3 or molecules affected by TS10q23.3 function. By virtue of the availability of cloned TSOq23.3 sequences, sufficient amounts of TS10q23.3 can be produced to perform crystallographic studies. In addition, knowledge of the polypeptide sequences permits computer employed predictions of structure-function relationships.

VI. Methods for Treating 10q23.3 Related Malignancies

The present invention also involves, in another embodiment, the treatment of cancer. The types of cancer that may be treated, according to the present invention, is limited only by the involvement of TS10q23.3. By involvement, it is not even a requirement that TS10q23.3 be mutated or abnormal—the overexpression of this tumor suppressor may actually overcome other lesions within the cell. Thus, it is contemplated that a wide variety of tumors may be treated using TS10q23.3 therapy, including cancers of the brain (glioblastoma, astrocytoma, oligodendroglioma, ependymomas), lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Genetic Based Therapies

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing TS10q23.3 to that cell. Because the human, mouse and dog genes all encode the same polypeptide, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particticles to the patient. Similar figures may be extrapolated for liposomal or other non-viral formulations by comparing relative uptake efficiencies. Formulation as a pharmaceutically acceptable composition is discussed below.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefilly, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way TS10q23.3 may be utilized according to the present invention.

B. Immunotherapies

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that TS10q23.3 could serve as a target for an immune effector given that (i) it is unlikely to be expressed on the surface of the cell and (ii) that the presence, not absence, of TS10q23.3 is associated with the normal state. However, it is possible that particular mutant forms of TS10q23.3 may be targeted by immunotherapy, either using antibodies, antibody conjugates or immune effector cells.

A more likely scenario is that immunotherapy could be used as part of a combined therapy, in conjunction with TS10q23.3-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

C. Protein Therapy

Another therapy approach is the provision, to a subject, of TS10q23.3 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

D. Combined Therapy with Immunotherapy, Traditional Chemo- or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that TS10q23.3 replacement therapy could be used similarly in conjunction with chemo- or radiotherapeutic intervention. It also may prove effective to combine TS10q23.3 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a TS10q23.3 expression construct and at least one other agent. These compositions would be provided in a combined amount effective to kill or inhibit proliferation of the cell. This process may involve contacting the cells with the expression construct and the agent(s) or factor(s) at the same tine. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TS10q23.3 or the other agent will be desired. Various combinations may be employed, where TS10q23.3 is "A" and the other agent is "B", as exemplified below:

A/B/A B/A/B B/B/A A/A/B B/A/A A/B/B B/B/B/A B/B/A/B A/A/
B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/
A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FLU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a TS10q23.3 expression construct is particularly preferred as this compound.

In treating cancer according to the invention, one would contact the tumor cells with an agent in addition to the expression construct. This may be achieved by irradiating the localized tumor site with radiation such as X-rays, UV-ight, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a TS10q23.3 expression construct, as described above.

Agents that directly cross-link nucleic acids, specifically DNA, are envisaged to facilitate DNA damage leading to a synergistic, antineoplastic combination with TS10q23.3. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and punty standards as required by FDA Office of Biologics standards.

The inventors propose that the regional delivery of TS10q23.3 expression constructs to patients with 10q23.3-linked cancers will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining TS10q23.3-targeted therapies with chemo- and radiotherapies, it also is contemplated that combination with other gene therapies will be advantageous. For example, targeting of TS10q23.3 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove. useful by themselves in treating a TS10q23.3. In this regard, reference to chemotherapeutics and non-TS10q23.3 gene therapy in combination should also be read as a contemplation that these approaches may be employed separately.

E. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermai, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifimgal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifimgal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VII. Transgenic Animals/Knockout Animals

In one embodiment of the invention, tansgenic animals are produced which contain a functional transgene encoding a functional TS10q23.3 polypeptide or variants thereof. Transgenic animals expressing TS10q23.3 transgenes, recombinant cell lines derived from such animals and transgenic embryos may be useful in methods for screening for and identifying agents that induce or repress function of TS10q23.3. Transgenic animals of the present invention also can be used as models for studying indications such as cancers.

In one embodiment of the invention, a TS10q23.3 transgene is introduced into a non-human host to produce a transgenic animal expressing a human or murine TS10q23.3 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous TS10q23.3 by homologous recombination between the transgene and the endogenous gene; or the endogenous gene may be eliminated by deletion as in the preparation of "knock-out" animals. Typically, a TS10q23.3 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress TS10q23.3 or express a mutant form of the polypeptide. Alternatively, the absence of a TS10q23.3 in "knock-out" mice permits the study of the effects that loss of TS10q23.3 protein has on a cell in vivo. Knock-out mice also provide a model for the development of TS10q23.3-related cancers.

As noted above, transgenic animals and cell lines derived from such animals may find use in certain testing experiments. In this regard, transgenic animals and cell lines capable of expressing wild-type or mutant TS10q23.3 may be exposed to test substances. These test substances can be screened for the ability to enhance wild-type TS10q23.3 expression and or function or impair the expression or function of mutant TS10q23.3.

VIII. EXAMPLES

The following examples are included to demonstrate preferred embodiments of the invention. It should be appreciated by those of skilled the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1
Homozygous Deletions in Glioma Cell Lines

Figure 2:
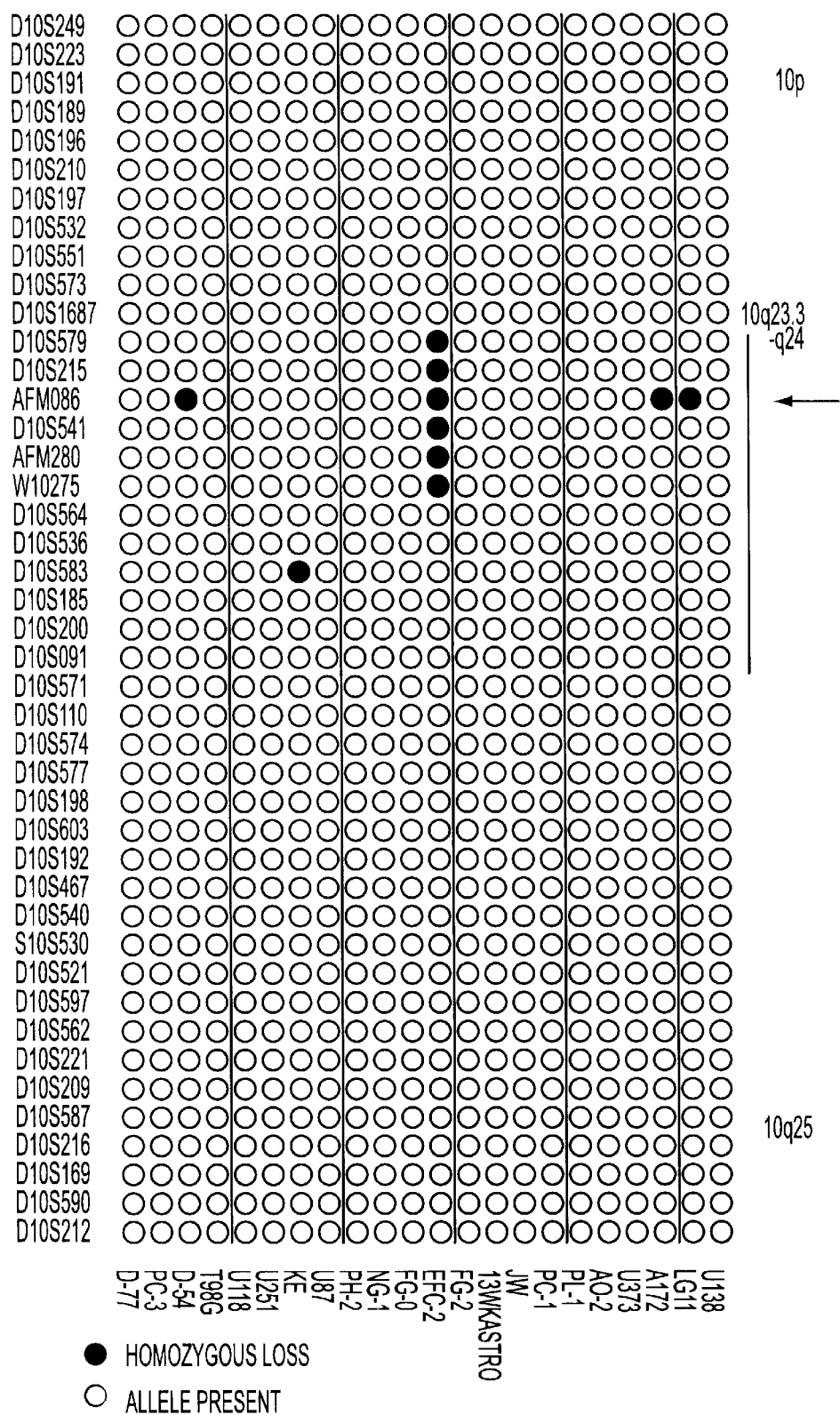
FIG. 2—Illustration of Homozygous Deletions in Glioma Cell Lines. Various glioma cell lines were screened for the presence of deletions in both copies of loci on chromosome 10. Loci are indicated on the vertical axis and cell lines are listed across the horizontal axis. Homozygous loss is indicated by a darkened oval. The glioma cell lines D54, EFC-2, A172 and LG11 were examined for the presence of marker AFMA086WG9 (AFM086). The marker was shown to be deleted in multiplexed polymerase chain reactions using several additional chromosome 10 polymorphic alleles in independent reactions. Allele D10S196 is shown as the control for the PCR reaction. EFC-2 cells showed homozygous deletion of 4 contiguous markers.

The inventors have examined DNA from a series of 21 glioma cell lines and primary cultures, along with normal cells, to identify homozygous deletions of genomic material on chromosome 10. Markers were chosen for their approximate location at or near previously implicated regions (FIG. 1). The cells analyzed were generated in the Department of Neuro-Oncology UTMDACC (LG11, EFC-2, PL-1, PC-1, JW, FG-2, FG-0, NG-1, PH-2, KE, PC-3, and D77), were commercially available (U138, A172, U373, U87, U251, U118, and T98G), or obtained from collaborators (13 wk astro, D54-MG). Markers were obtained from Research Genetics, Huntsville, Ala., or synthesized from reported sequence. Once cell line, EFC-2, revealed a large homozygous deletion associated with four markers surrounding D108215 (FIG. 2). This deletion was also observed by FISH using YAC 746h6, which maps to the region. Three other cell lines (D-54, A172, and LG11) also demonstrated homozygous deletions at AFMA086WG9 (AFMA086), thereby strongly implicating the region to contain a putative tumor suppressor gene (FIG. 2). Deletions in PCR™ reactions were performed in the presence of two primer pairs (multiplexed) to assure appropriate amplification conditions. All deletions were confirmed by (at least) triplicate reactions. This same region has also been implicated in prostate carcinoma (Gray et al., 1995). Homozygous deletions in cell lines also have been used to define a tumor suppressor gene locus at 3p21.3 in small cell lung carcinoma (Daly et al., 1993; Kok et al., 1994; Wei et al., 1996).

Example 2
Retention of 10q Loci in Suppressed Hybrid Cells

Figure 3:
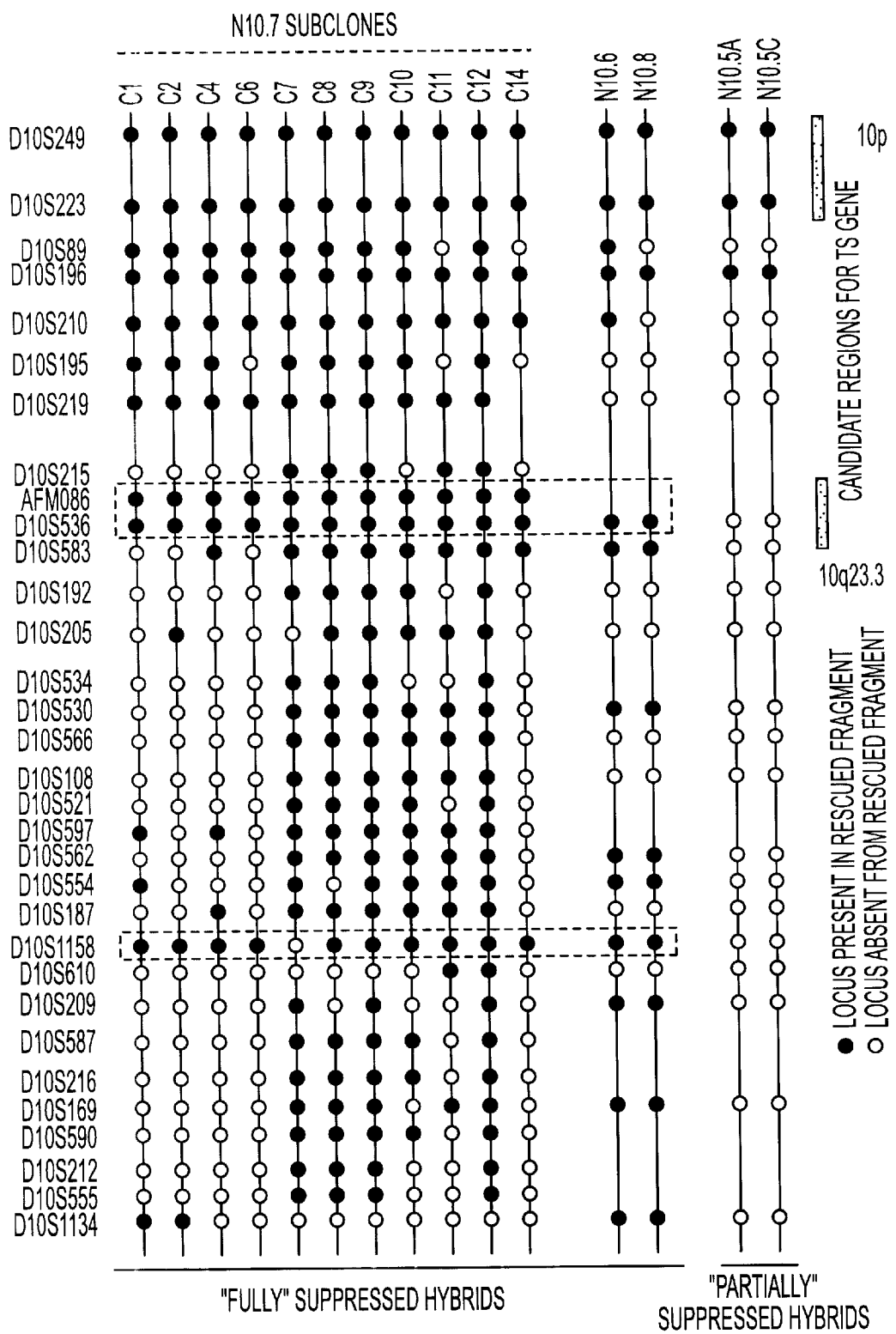
FIG. 3—Illustration of Regions of Chromosome 10: Presence or Absence of DNA Microsatellite Markers in Hybrid Clone. Regions of chromosome 10 presence (solid circle) or absence (open circle) of DNA corresponding to chromosome 10 specific microsatellite markers from eleven subclones of the somatic cell hybrid clone U251.N10.7 that were transferred into mouse A9 cells are illustrated. The U251.N10.6 and U251.N10.8 somatic cell hybrids are fully suppressed clones, exhibiting no or little growth in soft agarose, and the U251.10.5A and C subclones are partially suppressed (Steck et al., 1995). The difference between the fully suppressed clones and the partially suppressed clones provides a functional localization of the tumor suppressor gene. The possible regions that contain the tumor suppressor gene are indicated by the hatched boxes. The hatched box at 10q23.3 overlaps with the homozygous deletions and region implicated by allelic deletion analysis (see FIG. 2 and FIG. 4).

The inventors' second strategy was to examine the regions of chromosome 10 that were retained in suppressed hybrid clones, but absent in the revertant clones. This analysis extended the inventors' previous study, showing the presence of two tumor suppressor loci on chromosome 10 and analyzing the regions that were retained. Hybrids retaining all or portions of 10q failed to grow in soft agarose and in nude mice ("fully" suppressed clones), while hybrid cells that lost the majority of the inserted chromosome 10q grew in soft agarose, but were nontumorigenic ("partially" suppressed clones; Steck et al., 1995; FIG. 3, right side). Original clones U251N10.6, N10.7, and N10.8 previously were shown to retain only fragments of 10q (Pershouse et al., 1993; Steck et al., 1995). Using additional informative microsatellite markers, three retained regions were identified in all three suppressed clones; a 22 cM region from D10S219 to D10S110, a 14 cM region from D10S192 to D10S187, and a 18 cM region from D10S169 through D10S1134 (FIG. 3).

To bypass this limitation, the originally transferred neomycin resistance-tagged chromosome 10 from hybrid U251.N10.7 was "rescued" by microcell-mediated chromosome transfer into mouse A9 cells. This allows all human microsatellite markers to be informative for the presence of chromosome 10. The basis for this analysis is that all "fully" suppressed subclones should retain a common region and this region is deleted in the "partially" suppressed subclones. An additional impetus was that N10.7 displayed considerable heterogeneity in the size of chromosome 10 retained, as determined by FISH using chromosome 10 specific probes. Also, hybrid cells used for his rescue were first assayed for soft agarose growth and showed no colony formation. The mouse hybrids containing the transferred human chromosome 10 all contained the short arm of chromosome 10. The same region was retained in the "partially" suppressed clones (N10.5a–j) that grew in soft agarose (Steck et al., 1995), thus excluding this region (10pter-10q11) as containing the 10q tumor suppressor gene. Examination of the retained regions of 10q illustrated considerable heterogeneity (FIG. 3). The majority of clones showed either partial or extensive deletions of 10q23-26. Only two regions were retained in all the subclones examined. The most centromeric region retained involved the markers D10S210 and D10S219. However, these markers were absent in the original N10.6 and/or N10.8 clones, excluding this region (FIG. 3). The other region was centromeric of D4S536 but telomeric of D10S215 (~4 cM). The markers AFM086 and D10S536 were retained in all clones examined (boxed region in FIG. 3). These markers were absent in the partially suppressed clones (N10.5a–j). These results demonstrate that a common region, surrounding AFM086, is retained in all hybrid cells that are phenotypically suppressed. This same region is deleted in several glioma cell lines.

This analysis has several limitations. First, the rescued clones cannot be analyzed for biological activity, therefore any changes in chromosome 10 which may have occurred during or after transfer could not be detected. To partially address this concern, the inventors' analysis was performed as soon as the clones were able to be harvested. Furthermore, retention of this portion of the chromosome may only "correct" an in vitro artifactual deletion. Consequently, allelic deletion studies were performed to determine if this region was involved in gliomas. Also, an alternative region was suggested by this analysis at D10S1158, where all the clones but one (C7) retained this region. However, the retained region at AFM086 also exhibited homozygous deletions, thereby being implicated by two alternative methods as compared to D10S1158. It is also interesting to note that the tumor suppressor gene region appears to be preferentially retained, while the remainder of 10q is fragmented.

Example 3
Allelic Deletion Analysis of 10q

Figure 4:
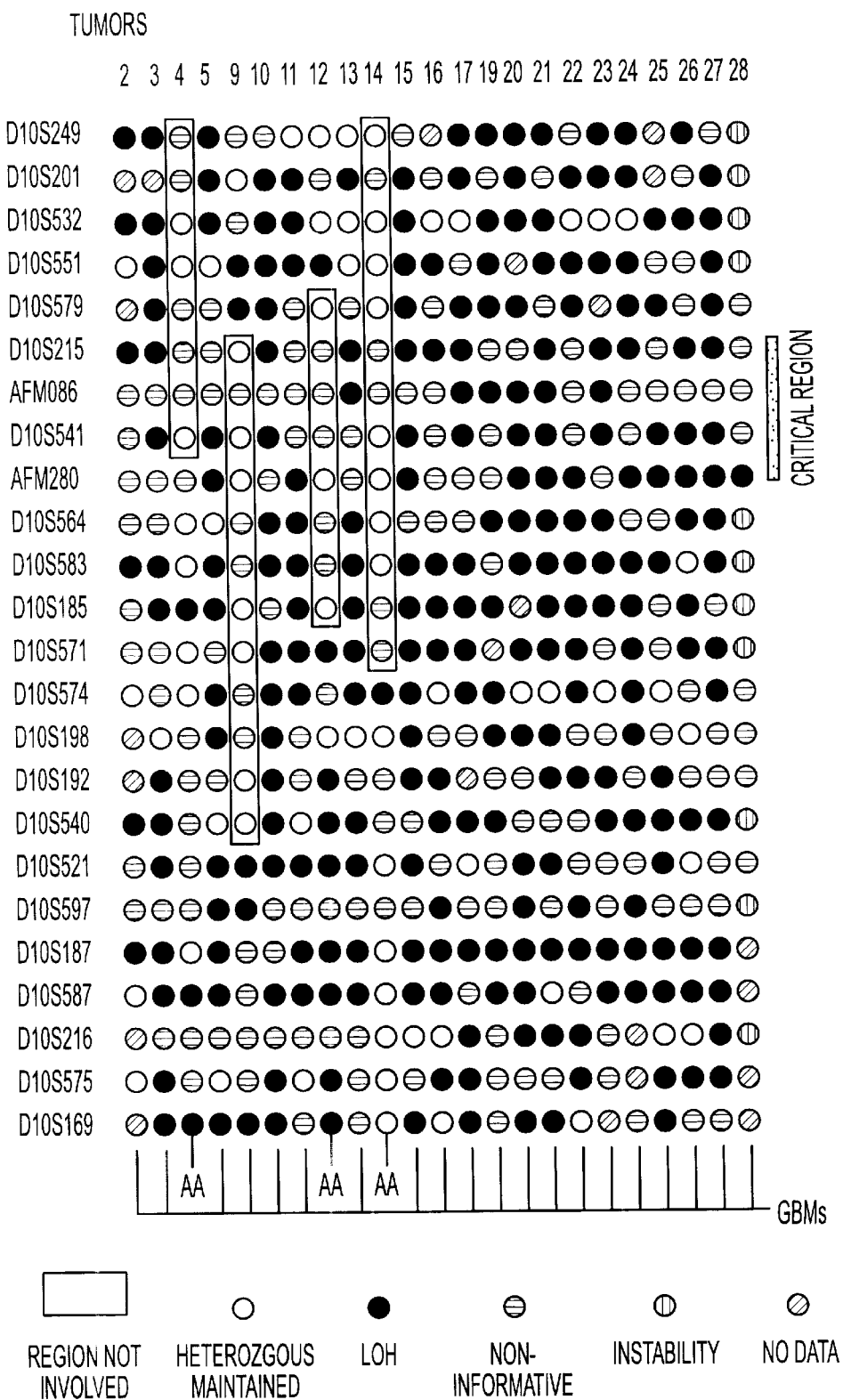
FIG. 4—Deletion Map of Chromosome 10 in Human Gliomas. The region bounded by the markers D10S551 to D10S583 are located in a 10 cM region. The microsatellites are shown in their order of most probably linkage and mapped to their approximate chromosomal location based on the radiation hybrid map as described by Gyapay et al., 1994. The region of chromosome 101 that is not involved in anaplastic astrocytomas and one glioma is shown in the boxed regions of the tumor. The critical region defined from the homozyogous deletion analysis and not excluded by this analysis is shown by the solid bar on the right side.

An allelic deletion study was performed on DNA from a series of 53 glioma specimens and corresponding patient lymphocytes using microsatellite markers specific for chromosome 10. This study was undertaken to determine if our critical region also was involved in glioma specimens. Extensive deletions were observed in the majority of specimens derived from GBM, with 30 of 38 GBMs exhibiting deletion of most or all of chromosome 10 markers. Less extensive deletions were observed in the majority if specimens derived from anaplastic astrocytomas, while infrequent deletions were observed in astrocytomas and most oligodendrogliomas (FIG. 4 and data not shown). The majority of markers used in this analysis mapped to 10q23-26 (Gyapay et al., 1994). Similar to other studies, a common region of deletion could not be convincingly demonstrated, due to the large deletions in most GBM samples (Fults et al., 1993; Rasheed et al., 1995).

However, for the GBM specimens examined, all but one tumor sample (#9; FIG. 4) revealed deletions involving the region from D10S579 to D10S541. Furthermore, only one AA showed a deletion at the inventors' critical region, and no astrocytomas. Two oligodendrogliomas exhibited deletions within the critical region, but both were diagnosed as malignant. This study presents several possibilities. First, the deletions involving the inventors' critical region occur predominantly in GBMs and not in lower grade tumors. This would imply that loss of the tumor suppressor gene on chromosome 10q in the inventors' critical region would represent a genetic alteration associated with progression to GBM. In support of this hypothesis, even though deletions occur on 10q in lower grade tumors, no common region of deletion on 10q was identified for these specimens. This observations would, again, support the inventors' previous suggestion that deletion of the 10q tumor suppressor gene is predominantly associated with GBMs and not all deletions on 10q affect the tumor suppressor gene. The region D10S216 to D10S587, suggested by Rasheed, showed extensive deletions, but several GBMs exhibited retention of heterozygosity at this region (tumors #2, #9, #13, #26; FIG. 4). Also, if low grade tumors are excluded from their study, the inventors' region is implicated in all GBMs. This combination of independent approaches strongly suggests a 10q tumor suppressor gene maps to the region D10S215 to D10S541, specifically at AFM086.

Example 4
Mapping of Candidate Tumor Suppressor Gene Region

Figure 8:
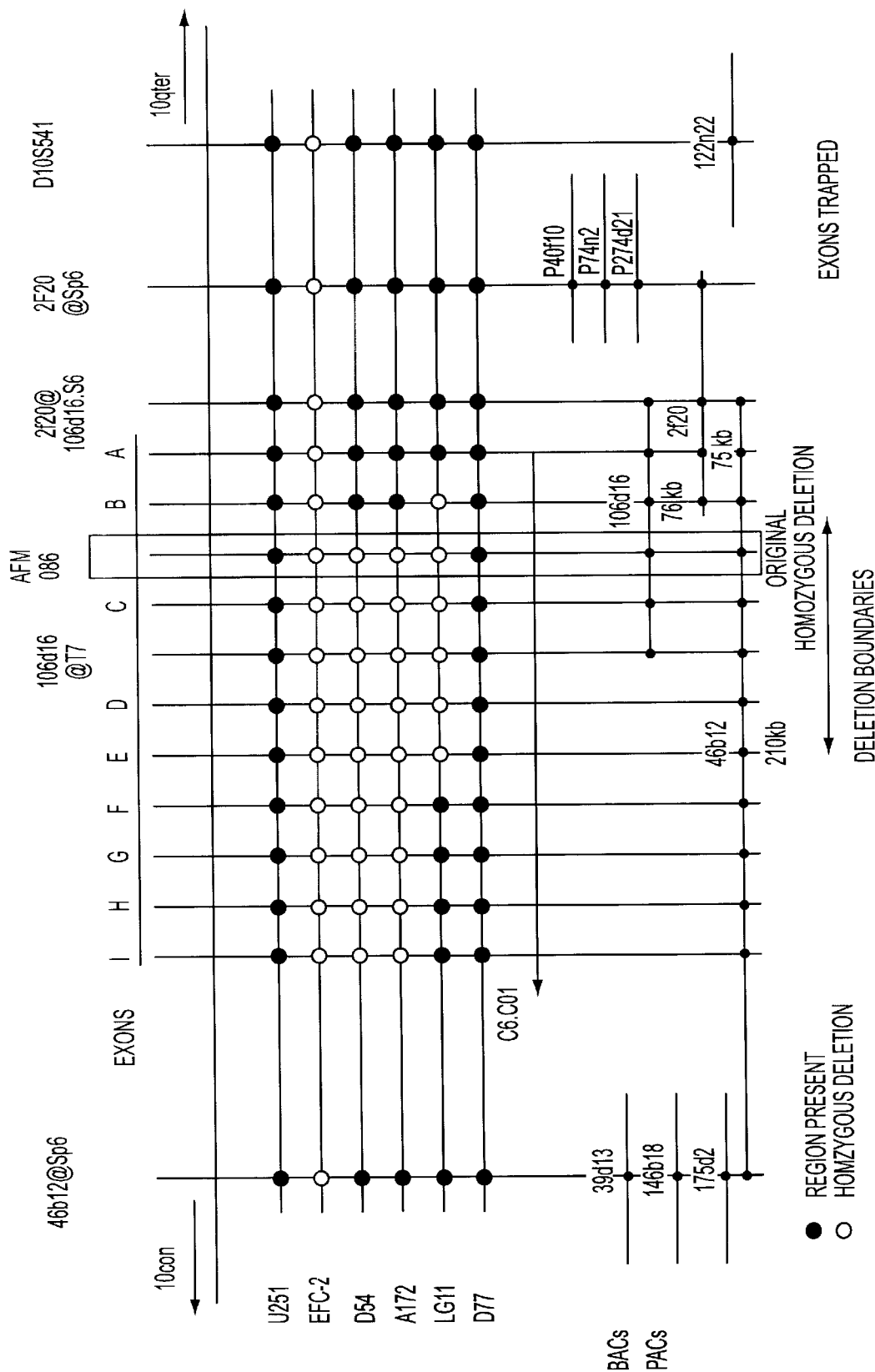
FIG. 8—Deletional Analysis of 10q23.3. Glioma line initially indicated as having homozygous deletions in 10q23.3 were reanalyzed for the presence of the TS10q23.3 gene. Darkened oval indicates that the gene region is present; open oval indicates a homozygous deletion in the gene region. *—indicates exons trapped.
Figure 11G:
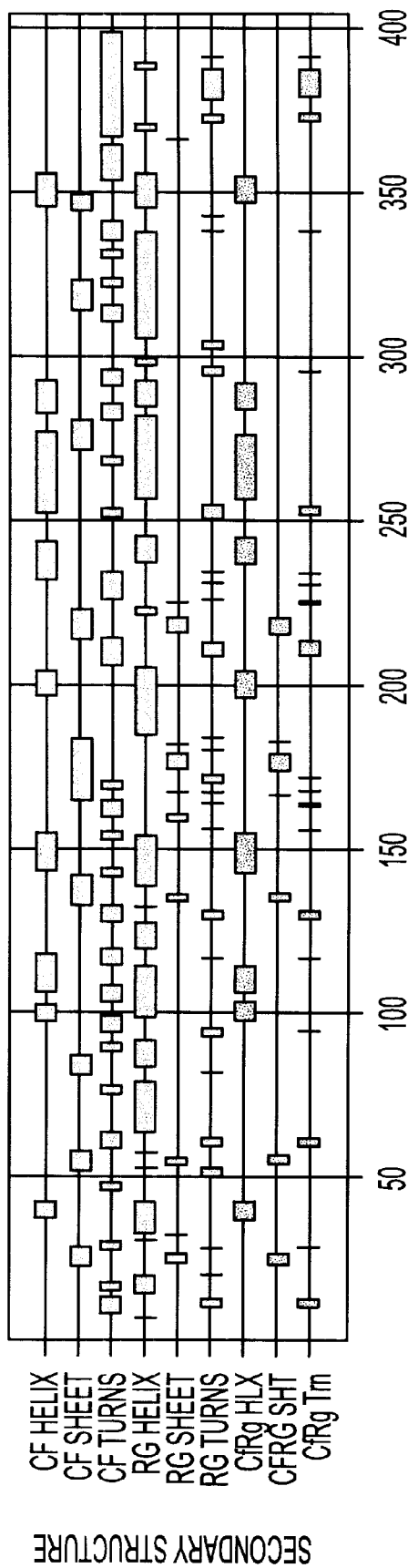
Figure 12C:
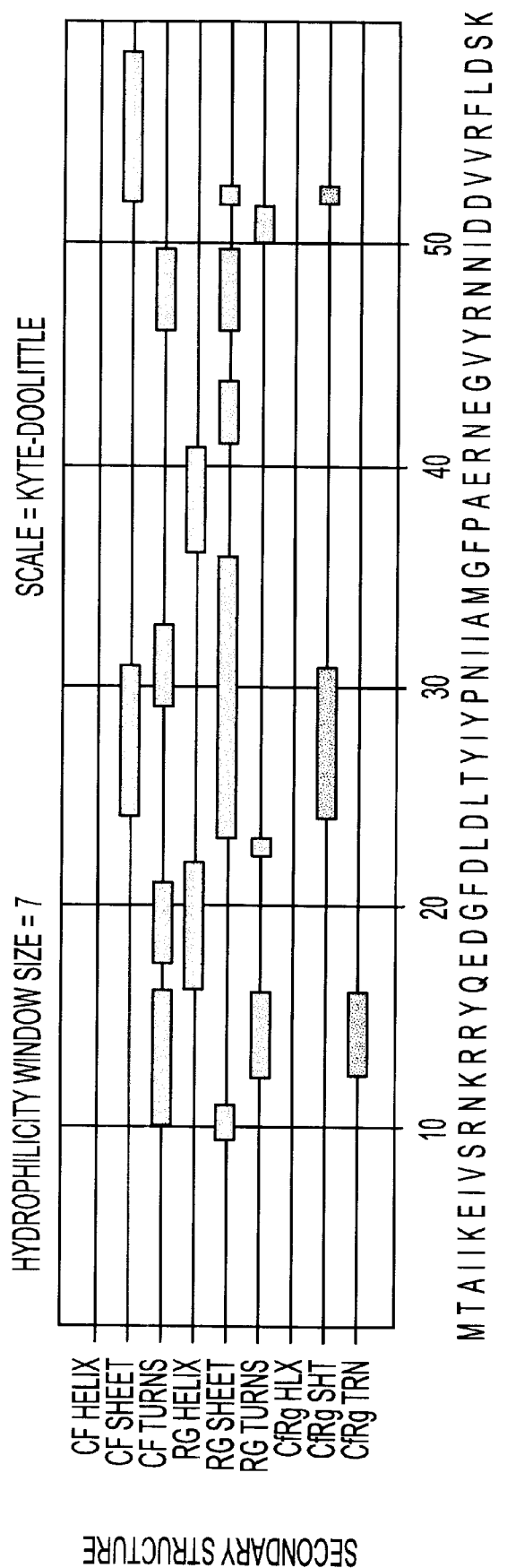
Figure 12D:
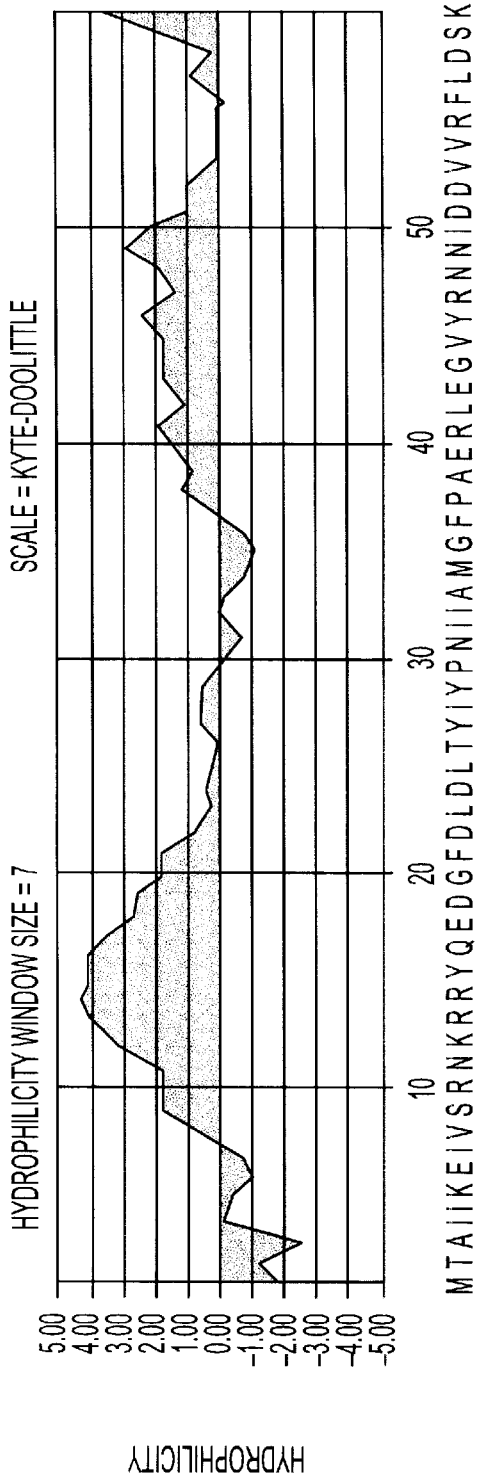
Figure 12E:
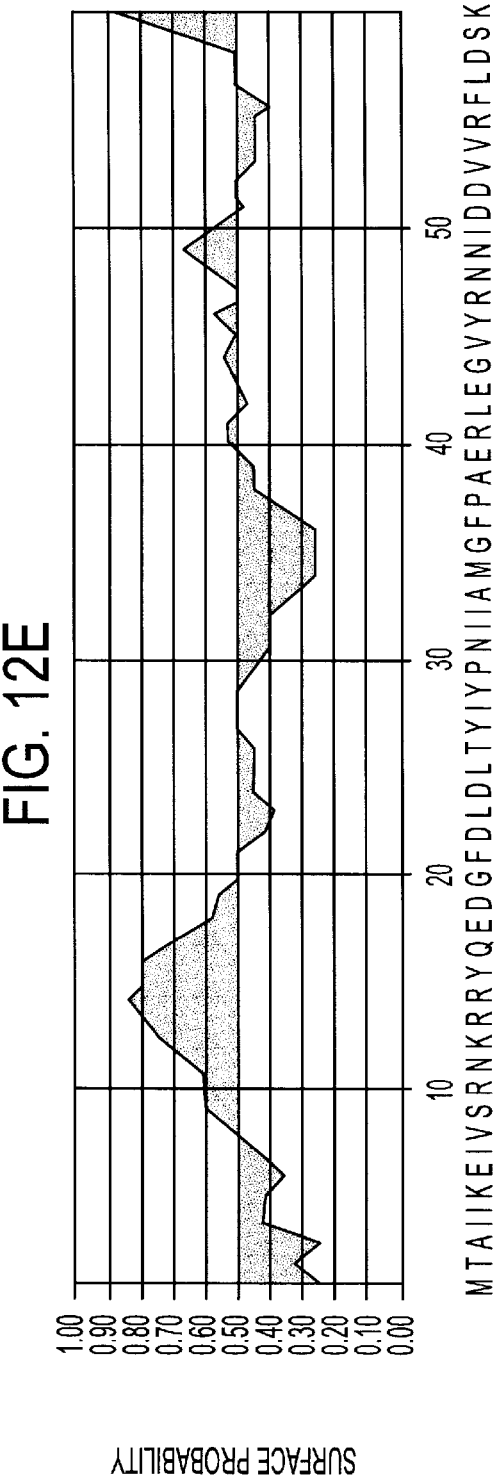
Figure 12F:
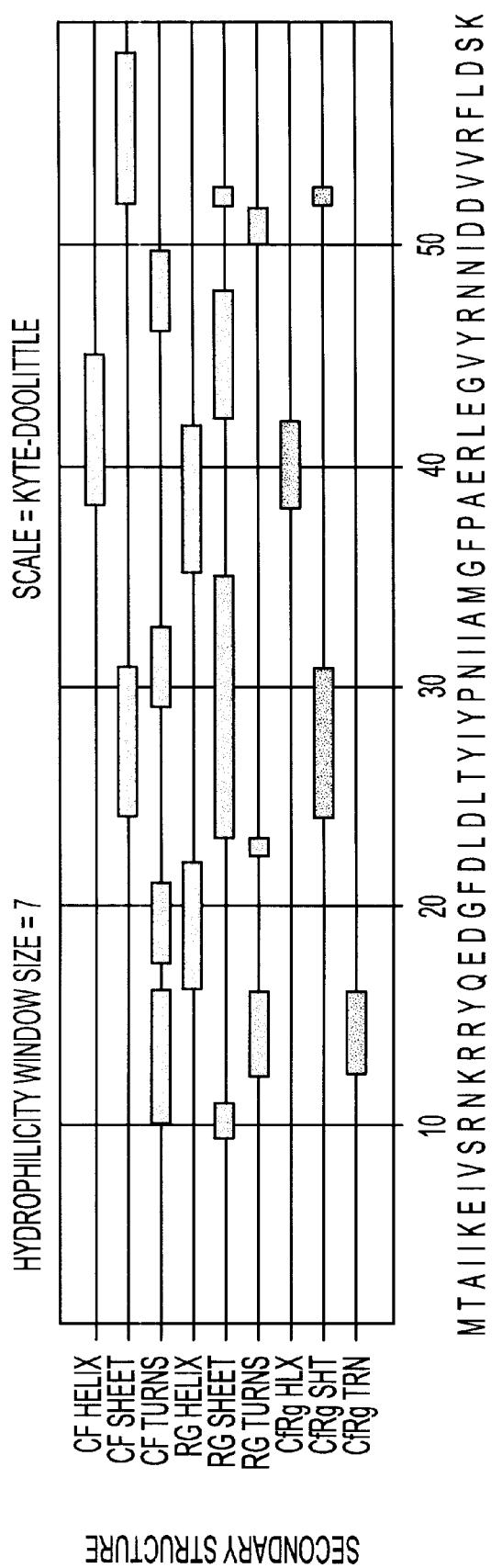
Figure 12I:
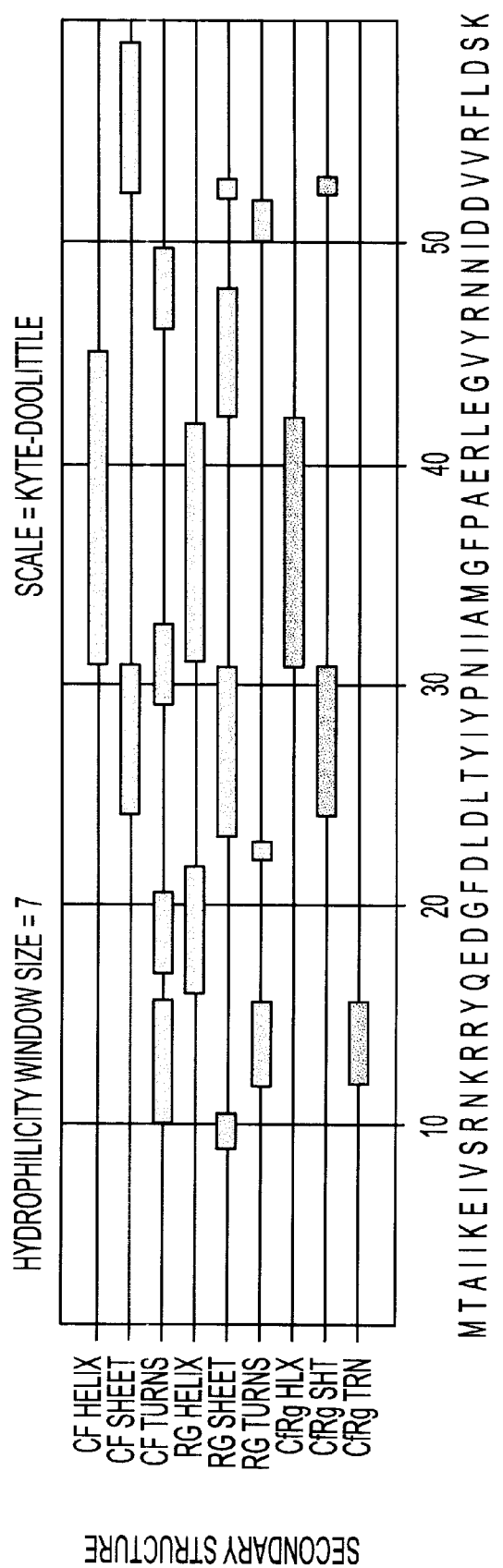

The critical region the inventors have identified is centered at AFM086 and is bordered by D10S215 and SOS541 (FIGS. 2 and 8). This region is relatively small, being contained within several individual YACs (787d7; 746h8; 934d3). FISH painting with YAC 746h8 on EFC-2 metaphase spreads shows that the homozygous deletion is contained within the YAC as the YAC was partially observed and adjacent YACs on both sides were present. Bacterial artificial chromosomes (BACs) or PACs for all markers in the region have been isolated (FIG. 8). The BAC contig of the region was constructed from end sequences of BACs mapping to the region. Several notable features have been identified. First, two overlapping BACs were identified (46b12 and 2f20) and verify the genomic integrity of 106d16. Second, a Not I site was identified at one end of the BACs. The presence of the Not I site and coincident restriction digestion with SacII, EagI, and BssHII suggest the presence of a CpG island within 106d16.

Figure 5:
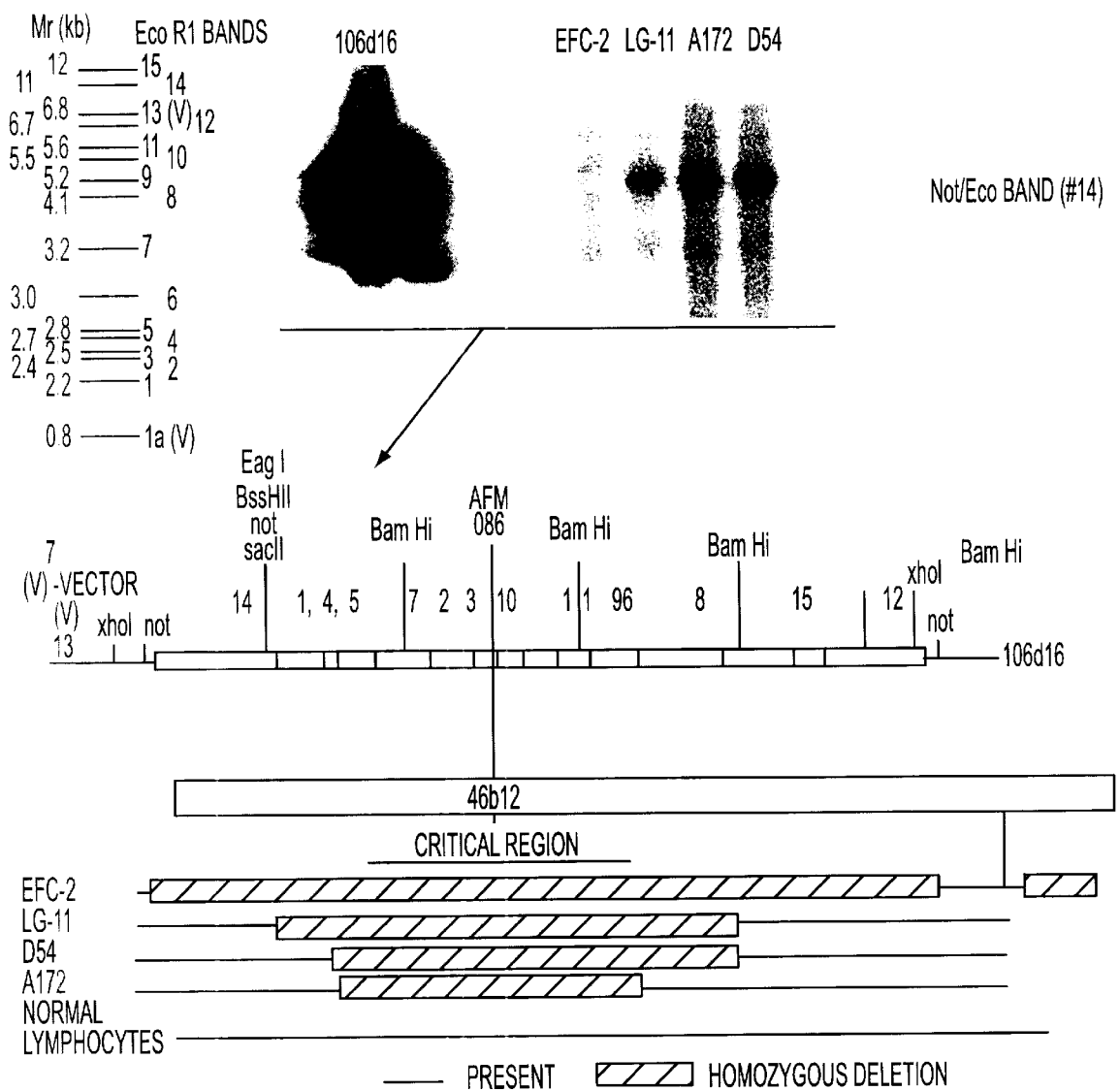
FIG. 5—Mapping of BAC 106d16. Mapping of the BAC designated 106d16, and demonstration of homozygous deletion by Southern blotting is illustrated. The partial restriction map of 106d16 is depicted. The illustration of the blot shows the homozygous deletion of Eco band #14 (Mr.approx. 11 kb) in EFC-2 cells.

The EcoRI fragments from BAC 106d16 were used to examine the extent of the homozygous deletions, by Southern blotting, in the glioma cells that were previously shown to have homozygously deleted AFM086 (FIGS. 2 and 5). The right side (EcoRI fragment 14) contains the probable CpG island and is present in three of the four cell lines. A NotI/EcoRI (#3) fragment was used as a probe on a Southern blot containing several BACs and the glioma cell line (FIG. 2). Deletions to the telomeric side (right side) have not been detected using probes from 46b12, except for EFC-2 cells. However, additional homozygous deletions have been observed in the cells within the region defined by 106d16 (~65 kb). A homozygous deletion for band 3 is observed for LG11 and EFC-2 cells, but not the additional glioma cells or normal controls. 106d16 (band 12) has been observed to be present in all cells (EFC-2 exhibits an altered migrating band), suggesting the homozygous deletion is contained entirely within 106d16.

Example 5
Identification of Expressed Genes within the Critical Region

EcoRI fragments from BAC 106d16 were generated and size separated by agarose gel electrophoresis. Individual bands or pools of similar sized bands were ligated into pSPL3 (GIBCO, Gaithersburg, Md.). Putative exons were identified as described by the manufacturer. Two exons were properly spliced into the trapping vector. The exons were derived from band pool 2, 3, 4, 5 and band 7. The sequence of the trapped exons was determined and defined by the known trapping vector sequence. Using BLAST searches of expressed sequence tag (dbEST) database, five potential expressed sequence tags (ESTs) were identified. Two ESTs (gb/H92038, AA009519) were observed to contain either one or both of the exons (albeit one EST was in the wrong orientation).

Sequencing primers were generated from the ESTs and used to define putative exon-intron boundaries using BAC46b12 as a template. Nine exons were identified. Sequence differences between the ESTs and the genomic template were corrected. All the exons were contained within BAC 46b12. Primers were generated from the intron sequences adjacent to the exons to form amplicon units for each exon. Two of the exons were corresponded to the trapped exons from the BAC 106d16 EcoRI sequences. The sequence of the gene is shown in FIG. 6. The predicted amino acid reading was defined by the presence of an ATG start site, TGA and TAA stop codons in frame, the presence of multiple stop codons in all three reading frames elsewhere in the sequence, nine splicing sites, and the presence of Kozak signals near the initiation site. The 403 amino acid sequence is shown in FIG. 7 and FIG. 9. The predicted molecular weight is 47,122 with a pI of 5.86.

A possible functional role for the protein product is suggested by its sequence homology to several protein motifs. A critical motif from residues 88 to 98 [IHCKAGKGRTG] (SEQ ID NO:17) has an exact match for the conserved catalytic domain of a protein tyrosine phosphatase [(I/V)HCxAGxxR(S/T)G] (SEQ ID NO:18) (Denu et al., 1996). Several other motifs were identified that would agree with the phosphatase function for the tumor suppressor gene.

Amplicons (PCR™ products generated from various regions of the gene) were generated from random primed cDNA. The amplicons sequence corresponded to the DNA sequence. Non-overlapping amplicons were used to probe Northern blots of normal tissue derived from various organs (Clontech, Palo Alto, Calif.; multitissue blots). All amplicons identified a major band at 5.5 to 6 kb on the Northern blots and several minor bands. The message was expressed in all tissues examined (heart, brain, placenta, lung, liver skeletal muscle, kidney, pancreas, spleen, thymus, prostate, testes, ovary, small intestine, colon and peripheral blood lymphocytes).

Example 6
Mutational Analysis

The mutational analyses have initially proceeded on two fronts. First, the glioma cell lines initially shown to have homozygous deletions were analyzed for the presence of the candidate gene. As shown in FIG. 8, all of the cell lines that exhibited deletion of AFM086 bad homozygous deletions of multiple exons of the candidate gene. Furthermore, the deletions occurred in the middle of the gene, thus defining the deletion boundaries (similar deletions in all cell lines) between exons B and G. Deletions that affect the middle of the gene further indicate that the identified gene represents the gene targeted for mutation.

Preliminary analysis for sequence mutations was also performed on a series of glioma cell lines. Mutations and/or deletions were observed in all but three glioma cell lines examined (Table 4). Reference to base number in the table references the exon, not the entire sequences, i.e., the 98th base of exon G for U251.

TABLE 4

IDENTIFIED MUTATIONS IN CANDIDATE GENE

| | Cells | Cell Type | Mutation | Predicted Effect |
|---|---|---|---|---|
| 1 | U87 | glioma | splice junction exon c: $G + 1 > T$ | splicing variant |
| 2 | U138 | glioma | splicing site exon h; $G + 1 > T$ | splicing variant |
| 3 | U251 | glioma | 2 bp addition exon G; 98 ins TT | |
| 4 | U373 | glioma | frame shift exon G | |
| 5 | EFC-2 | glioma | –all exons | no product |
| 6 | D54 | glioma | –exons C-I | no product |
| 7 | A172 | glioma | –exons C-I | no product |
| 8 | LG11 | glioma | –exons B-I | no product |
| 9 | T98G | glioma | missense exon B; T46- > G | leu > arg |
| 10 | KE | glioma | missense exon B; G28- > G | gly > glu |
| 11 | F60 | glioma | terminal mutation exon H; C202- > T | terminal stop |
| 12 | D77 | glioma | no mutation (heterogeneous for 10q | |
| 13 | PC-3 | low grade | no mutation | |
| 14 | PH-2 | low grade | no mutation | |
| 15 | nLnCap | prostate | deletion exon A, 16–17 del AA; mutation B, C53- > T | silent |

Also, deletions of exons were found in LnCap, a prostate cell line. The glioma cells that failed to show a mutation/deletion were derived from low grade tumors (PC-3 and PH-2) where no allelic deletion of chromosome 10 is expected and has been observed for these cells. The other cells (D77) were a primary cell culture, and chromosome 10 was shown to be heterozygous from a 1 bp polymorphism within the gene. A breast cancer cell line also showed a mutation. This initial analysis supports the inventors' conclusion that loss of a 10q tumor suppressor gene represents a critical molecular marker for glioblastoma and disease progression.

IX. REFERENCES

The following references, to the extent that they provide exemplary procedural or other details supplementary to those set forth herein, are specifically incorporated herein by reference:

Albarosa et al., Deletion mapping of gliomas suggest the presence of two small regions for candidate tumor-suppressor genes in a 17-cM interval on chromosome 10q. *Am. J. Genet.*, 58:1260–1267, 1996.

Baichwal and Sugden, Vectors for gene transfer derived from animal DNA viruses: Transient and stable expression of transferred genes. In: *Gene Transfer*, Kucherlapati R, ed., New York, Plenum Press, pp. 117–148, 1986.

Barany and Merrifield, The Peptides, Gross and Meienhofer, eds., Academic Press, New York, pp. 1–284, 1979.

Benvenisty and Neshif, Direction introduction of genes into rats and expression of the genes. *Proc. Nat. Acad. Sci. USA*, 83:9551–9555, 1986.

Bianchi et al., Mutations in transcript isoforms of the neurofibromatosis 2 gene in multiple human tumor types. *Nature Genetics*, 6:185–192, 1994.

Bigner et al., Specific chromasomal abnormalities in malignant human gliomas. *Cancer Res.*, 48:405–411, 1988.

Bigner et al., Specific chromosomal abnormalities in malignant human gliomas. *Cancer Res.* 48:405–411, 1988.

Bishop, J. M., Molecular themes in oncogenesis. *Cell*, 64:2351–248, 1991.

Boring et al., *Cancer Statistics*, 1994 CA, 43:7–26, 1994.

Brinster et al., *Proc. Nat'l Acad. Sci. USA*, 82: 4438–4442, 1985.

Capaldi et al., *Biochem. Biophys. Res. Comm.*, 76:425, 1977

Carter et al., Allelic loss of chromosome 16q and 10q in human prostate carcinoma. *Proc. Natl. Acad. Sci. USA*, 87:8751–8755, 1990.

Chang et al., Foreign gene delivery and expression in hepatocytes using a hepatitis B virus vector. *Hepatology*, 14:124A, 1991.

Chen and Okayama, High-efficiency trnsfection of mammalian cells by plasmid DNA. *Mol. Cell Biol.*, 7:2745–2752, 1987.

Coffin, Retroviridae and Their Replication. In: *Virology*, Fields et al., eds., Raven Press, New York, pp. 1437–1500, 1990.

Cohen, P., The discovery of protein phosphatases: From chaos and confusion to an understanding of their role in cell regulation and human disease. *Bioessays*, 61–583–588, 1994.

Collet et al., Protein kinase activity associated with the avian sarcoma virus src gene product. *Proc. Natl. Acad. Sci. USA*, 75:2021–2024, 1978.

Coupar et al., A general method for the construction of recombinant vaccinia virus expressing multiple foreign genes, *Gene*, 68:1–10, 1988.

Culver et al., In vivo gene transfer with retroviral vector-producer cells for treatment of experimental brain tumors. *Science*, 256:1550–1552, 1992.

Daly et al., A homozygous deletion on chromosome 3 in small cell lung cancer cell line correlates with a region of tumor suppressive activity. *Oncogene* 8:1721–1729, 1993.

Denu et al., Form and function in protein dephosphorylation. *Cell* 87:361–364, 1996.

Dubensky et al., Direct tansfection of viral and plasmid DNA into the liver or spleen of mice. *Proc. Nat. Acad. Sci. USA*, 81:7529–7533, 1984.

El-Azouzi et al., Loss of distinct regions on the short arm of chromosome 17 associated with tumorigenesis of human astrocytomas, *Proc. Natl. Acad. Sci. USA*, 86:7186–7190, 1989.

EP 329 822, Davey et al.

Fearron and Vogelstein, A genetic model for colorectal tumorigenesis. *Cell*, 61:759–767, 1990.

Fechheimer et al., Transfection of mammalian cells with plasmid DNA by scrape loading and sonication loading. *Proc. Natl. Acad. Sci. USA*, 84:8463–8467, 1987.

Ferkol et al., Regulation of the phosphoenolpyruvate carboxykinase/human factor IX gene introduced into the livers of adult rats by receptor-mediated gene transfer. *FASEB J.*, 7:1081–1091, 1993.

Fodor et al., Light-directed, spatially addressable parallel chemical synthesis. *Science*, 251:767–773, 1991.

Foulds, The natural history of cancer. *J. Chronic Dis.*, 8:2–37, 1958.

Fraley et al, Entrapment of a bacterial plasmid in phospholipid vesicles: Potential for gene transfer. *Proc. Natl. Acad. Sci. USA*, 76:3348–3352, 1979.

Freshner, Animal Cell Culture: A Practical Approach, 2nd ed., Oxford/New York, IRL Press, Oxford University Press, 1992.

Friedmann, Progress toward human gene therapy. *Science*, 244:1275–1281, 1989.

Frohman, In: *PCR Protocols: A Guide To Methods And Applications*, Academic Press, N.Y., 1990.

Fujimoto et al., Loss of heterozygosity on chromosome 10 in human glioblastoma multiforme. *Genomics*, 4:210–214, 1989.

Fults & Pedone, Deletion mapping of the long arm of chromosome 10 in glioblastoma and multiforme. *Genes Chromosom. Cancer* 7:173–177, 1993.

Fults et al., Allelotype of human malignant astrocytoma, *Cancer Res.*, 50:5784–5789, 1990.

GB 2 202 328.

Gefter et al., *Somatic Cell Genet.*, 3: 231–236, 1977.

Ghosh-Choudhury et al., *EMBO J.*, 6:1733–1739, 1987.

Ghosh and Bachhawat, Targeting of Liposomes to Hepatocytes. In: *Liver Diseases, Targeted Diagnosis and Therapy Using Specific Receptors and Ligands*. Wu et al., eds., Marcel Dekker, New York, pp. 87–104, 1991.

Goding, 1986, In: *Monoclonal Antibodies: Principles and Practice*, 2d ed., Academic Press, Orlando, Fla., pp. 60–61, and 71–74, 1986.

Gomez-Foix et al.,*J. Biol. Chem.*, 267:25129–25134, 1992.

Gopal, Gene transfer method for transient gene expression, stable transfection, and cotransfection of suspension cell cultures. *Mol. Cell Biol.*, 5:1188–1190, 1985.

Graham and Prevec, In: *Methods in Molecular Biology: Gene Transfer and Expression Protocol*, E. J. Murray, ed., Humana Press, Clifton, N.J., 7:109–128, 1991.

Graham and van der Eb, A new technique for the assay of infectivity of human adenovirus 5 DNA. *Virology*, 52:456–467, 1973.

Graham et al., Characteristics of a human cell line transformed by DNA from human adenovirus type 5. *J. Gen. Virol.*, 36:59–72, 1977.

Gray et al., Loss of chromosomal region 10q23-25 in prostate cancer. *Cancer Res.*, 55:4800–4803, 1995.

Gray et al., Loss of chromosomal region 10q23-25 in prostate cancer. *Cancer Res.*, 55:4800–4803, 1995.

Grunhaus and Horwitz, Adenovirus as cloning vector. *Seminar in Virology*, 3:237–252, 1992.

Gyapay et al., The 1993–94 Genethon human genetic linkage map. *Nat. Genet.*, 7:246–339, 1994.

Hacia et al, Detection of heterozygous mutations in BRCA1 using high density oligonucleotide arrays and two-colour fluorescence analysis. *Nature Genetics*, 14:441–447, 1996.

Harland and Weintraub, Translation of mammalian mRNA injected into Xenopus oocytes is specifically inhibitedby antisense RNA. *J. Cell Biol.*, 101:1094–1099, 1985.

Henson et al., The retinoblastoma gene is involved in malignant progression of astrocytomas. *Ann. Neurol.*, 36:714–721, 1994.

Herbst et al., Loss of heterozygosity for 10q22-qter in malignant melanoma progression. *Cancer Res.*, 54:3111–3114, 1994.

Hermonat and Muzycska, Use of adenoassociated virus as a mammalian DNA cloning vector: Transduction of neomycin resistance into mammalian tissue culture cells. *Proc. Nat. Acad. Sci. USA*, 81:6466–6470, 1984.

Hersdorffer et al., *DNA Cell Biol.*, 9:713–723, 1990.

Herz and Gerard, *Proc. Nat'l Acad. Sci. USA*, 90:2812–2816, 1993.

Horwich, et al., Synthesis of hepadnavirus particles that contain replication-defective duck hepatitis B virus genomes in cultured HuH7 cells. *J. Virol.*, 64:642–650, 1990.

Hunter, T., Cooperation between oncogenes. *Cell*, 64-249–270, 1991.

Ittmann, Allelic loss on chromosome 10 in prostate adenocarcinoma. *Cancer Res.*, 56:2143–2147, 1996.

James et al., Clonal genomic alterations in glioma malignancy stages. *Cancer Res.*, 48:5546–5551, 1988.

Johnson et al., Peptide Turn Mimetics" IN: *Biotechnology And Pharmacy*, Pezzuto et al., eds., Chapman and Hall, New York, 1993.

Jones and Shenk, *Cell*, 13:181–188, 1978.

Kamb et al., A cell cycle regulator potentially involved in genesis of may tumor types. *Science*, 264:436–440, 1984.

Kaneda et al., Increased expression of DNA cointroduced with nuclear protein in adult rat liver. *Science*, 243:375–378, 1989.

Karlbom et al., Loss of heterozygosity in malignant gliomas involves at least three distinct regions on chromosome 10. *Hum. Genet.*, 92:169–174, 1993.

Karlsson et al., *EMBO J.*, 5:2377–2385, 1986.

Kato et al., Expression of hepatitis B virus surface antigen in adult rat liver. *J. Biol. Chem.*, 266:3361–3364, 1991.

Kimmelman et al., Loss of heterozygosity of chromosome 10p in human gliomas. *Genomics* 34:250–254, 1996.

Klein et al., High-velocity microprojectiles for delivering nucleic acids into living cells. *Nature*, 327:70–73, 1987.

Kok et al., A bomozygous deletion in a small cell lung cancer cell line involving a 3p21 region with a marked instability in yeast artificial chromosomes. *Cancer Res.* 54:4183–4187, 1994.

Komiya et al., Allelic losses at loci on chromosome 10 are associated with metastasis and progression of human prostate cancer. *Genes Chromo. Cancer* 17:245–253, 1996.

Kwoh et al., *Proc. Nat. Acad. Sci. USA*, 86: 1173, 1989.

Kyte and Doolittle, *J. Mol. Biol.*, 157(1):105–132, 1982.

Le Gal La Salle et al., *Science*, 259:988–990, 1993.

Lee et al., Human retinoblastoma susceptibility gene: cloning, identification, and sequence. *Science*, 235:1394–1399, 1987.

Levin et al., Neoplasms of the central nervous system. In: *Cancer: Principles & Practice of Oncology*, 4th ed., DeVita et al., eds., J. B. Lippincott Co., Philadelphia, 1993.

Levrero et al., *Gene*, 101:195–202, 1991.

Macejak and Samow, *Nature*, 353:90–94, 1991.

Manipulating the Mouse Embryo: A Laboratory Manual, 2nd ed., Hogan et al., eds., Cold Spring Harbor Laboratory Press, 1994.

Mann et al., Construction of a retrovirus packaging mutant and its use to produce helper-free defective retrovirus. *Cell*, 33:153–159, 1983.

Markowitz et al., *J. Virol.*, 62:1120–1124, 1988.

Merrifield, *Science*, 232: 341–347, 1986

Morita et al., Common regions of deletion on chromosomes 5q, 6q, and 10q in renal cell carcinoma. *Cancer Res.*, 51:5817–5820, 1991.

Mulligan, *Science*, 260:926–932, 1993.

Murakami et al., Suppression of the malignant phenotype of human prostate cancer cell line PPC-1 by introduction of normal fragments of human chromosome 10. *Cancer Res.*, 56:2157–2160, 1996.

Myers, EP 0273085.

Nicolas and Rubinstein, In: *Vectors: A survey of molecular cloning vectors and their uses*, Rodriguez and Denhardt, eds., Stoneham: Butterworth, pp. 494–513, 1988.

Nicolau and Sene, Liposome-mediated DNA transfer in eukaryotic cells. *Biochim. Biophys. Acta*, 721:185–190, 1982.

Nihei et al., Localization of a metastasis suppressor gene(s) for rat prostatic cancer to the long arm of human chromosome 10. *Genes Chromosom. Cancer*, 14:112–119, 1995.

Nishi et al., Differential expression of two types of the neurofibromatosis type 1 gene transcripts related to neural differentiation. *Oncogene*, 6:1555–1559, 1991.

Paskind et al., Dependence of moloney murine leukemia virus production on cell growth. *Virology*, 67:242–248, 1975.

PCT/US87/00880.

PCT/US89/01025.

Pease et al., Light-generated oligonucleotide arrays for rapid DNA sequence analysis. *Proc. Natl. Acad. Sci. USA*, 91:5022–5026, 1994.

Peiffer et al., Allelic loss of sequences from the long arm of chromosome 10 and replication errors in endometrial cancers. *Cancer Res.*, 55:1922–1926, 1995.

Pelletier and Sonenberg, *Nature*, 334:320–325, 1988.

Perales et al., Gene transfer in vivo: Sustained expression and regulation of genes introduced into the liver by receptor-targeted uptake. *Proc. Natl Acad. Sci.* 91:4086–4090, 1994.

Pershouse et al., Analysis of the functional role of chromosome 10 loss in human glioblastomas. *Cancer Res.* 53:5043–5050, 1993.

Petersen et al., Small-cell lung cancer is characterized by a high incidence of deletions on chromosomes 3p, 4q, 5q, 13q, and 17p. *Brit. J. Cancer* 75:79–86, 1997.

Pignon et al., *Hum. Mutat.*, 3: 126–132, 1994.

Racher et al., *Biotechnology Techniques*, 9:169–174, 1995.

Ragot et al., *Nature*, 361:647–650, 1993.

Ransom et al., Correlation of cytogenetic analysis and loss of heterozygosity studies in human diffuse astrocytomas and mixed oligo-astrocytomas. *Genes Chromosom. Cancer* 5:357–374, 1992.

Rasheed et al., Loss of heterozygosity for 10q loci in human gliomas. *Genes Chromo. Cancer*, 5:75–82, 1992.

Rasheed et al., *Oncogene*, 11:2243–2246, 1995.

Remington's Pharmaceutical Sciences, 15th ed., pp. 1035–1038 and 1570–1580.

Rempel et al., Loss of heterozygosity for loci on chromosome 10 is associated with morphologically malignant meningioma progression. *Cancer Res.*, 53:2386–2392, 1993.

Rich et al., *Hum. Gene Ther.*, 4:461–476, 1993.

Ridgeway, Mammalian Expression Vectors, In: *Vectors: A Survey of Molecular Cloning Vectors and Their Uses*, Rodriguez et al., eds., Stoneham: Butterworth, pp. 467–492, 1988.

Ritland et al., Region-specific loss of heterozygosity on chromosome 19 is related to the morphologic type of human glioma. *Genes. Chromo. Cancer*, 12:277–282, 1995.

Rosenfeld et al., In vivo transfer of the human cystic fibrosis transmembrane conductance regulator gene to the airway epithelium. *Cell*, 68:143–155, 1992.

Rosenfeld et al., *Science*, 252:431–434, 1991.

Roux et al., A versatile and potentially general approach to the targeting of specific cell types by retroviruses: Application to the infection of human cells by means of major histocompatibility complex class I and class II antigens by mouse ecotropic murine leukemia virus-derived viruses. *Proc. Nat'l Acad. Sci. USA*, 86:9079–9083, 1989.

Rubio et al., Analysis of the neurofibromatosis 2 gene in human ependymonas and astrocytomas, *Cancer Res.*, 54:45–47, 1994.

Russell and Rubinstein, Tumors of the neuroepithelial origin, In: *Pathology of Tumors of the Nervous System*, 5th ed., Williams and Wilkins, eds., pp. 82–219, 1989.

Sambrook et al., In: *Molecular Cloning: A Laboratory Manual*, 2d Ed., Cold Spring Harbor Laboratory Press, Cold Spring Harbor, N.Y., 1989.

Sanchez et al., Tumor suppression and apoptosis of human prostate carcinoma mediated by a genetic locus within human chromosome 10pter-q11. *Proc. Natl. Acad. Sci. USA*, pp. 2551–2556, 1996.

Sarver, et al., *Science*, 247:1222–1225, 1990.

Scheck and Coons, Expression of the tumor suppressor gene DCC in human gliomas. *Cancer Res.*, 53:5605–5609, 1993.

Shoemaker et al., Quantitative phenotypic analysis of yeast deletion mutants using a highly parallel molecular barcoding strategy. *Nature Genetics* 14:450–456, 1996.

Sonoda et al., *Cancer Res.*, 55:2166–2168, 1995.

Steck et al., Evidence for two tumor suppressive loci on chromosome 10 involved in glioblastomas. *Genes Chromosom. Cancer* 712:255–261, 1995.

Steck et al., Evidence for two tumor suppressive loci on chromosome 10 involved in glioblastomas, *Genes Chromo. Cancer*, 12:255–261, 1995.

Stewart and Young, Solid Phase Peptide Synthesis, 2d. ed., Pierce Chemical Co., 1984.

Stratford-Perricaudet and Perricaudet, Gene transfer into animals: the promise of adenovirus. In: *Human Gene Transfer*, O. Cohen-Haguenauer et al., eds., John Libbey Eurotext, France, pp. 51–61, 1991.

Stratford-Perricaudet et al., Evaluation of the transfer and expression in mice of an enzyme-encoding gene using a human adenovirus vector. *Hum. Gene. Ther.*, 1:241–256, 1990.

Tam et al., *J. Am. Chem. Soc.*, 105:6442, 1983.

Temin, Retrovirus vectors for gene transfer: Efficient integration into and expression of exogenous DNA in vertebrate cell genome. In: *Gene Transfer*, Kucherlapati R, ed., New York, Plenum Press, pp. 149–188, 1986.

Trybus et al., Distinct areas of allelic loss on chromosomal regions 10p and 10q in human prostate cancer. *Cancer Res.* 56:2263–2267, 1996.

Tur-Kaspa et al., Use of electroporation to introduce biologically active foreign genes into primary rat hepatocytes. *Mol. Cell Biol.*, 6:716–718, 1986.

U.S. Pat. No. 4,873,191, Wagner and Hoppe

U.S. Pat. No. 5,279,721.

Varmus et al., *Cell*, 25:23–36, 1981.

von Deimling et al., Deletion mapping of chromosome 19 in human gliomas. *Int. J. Cancer*, 57:676–680, 1994.

Voullaire et al., A functional marker centromere with no detectable alpha-satellite, satellite III, or CENP-B protein: activation of a latent centromere? *Am. J Hum. Genet.*, 52:1153–1163.

Wagner et al., *Science*, 260:1510–1513, 1993.

Walker et al., *Proc. Nat'l Acad. Sci. USA*, 89:392–396 1992.

Wei et al., Construction of a 600-kilobase cosmid clone contig and generation of a transcriptional map surrounding the lung cancer tumor suppressor gene (TSG) locus on human chromosome 3p21.3: progress toward the isolation of a lung cancer TSG. *Cancer Res.* 56:1487–1494, 1996.

Weinberg, Positive and negative controls on cell growth. *Biochemistry*, 28:8263–8269, 1989.

WO 88/10351, Gingeras et al.

WO 89/06700, Miller et al.

WO 90/07641, filed Dec. 21, 1990.

Wong et al., Appearance of b-lactamase activity in animal cells upon liposome mediated gene transfer, *Gene*, 10:87–94, 1980.

Wong et al., Increased expression of the EGF receptor gene in malignant gliomas is invariably associated with gene amplification. *Proc. Natl. Acad. Sci. USA*, 84:6899–6903, 1987.

Wu and Wu, *Adv. Drug Deivery Rev.*, 12:159–167, 1993.

Wu and Wu, Evidence for targeted gene delivery to HepG2 hepatoma cells in vitro. *Biochemistry*, 27:887–892, 1988.

Wu and Wu, Receptor-mediated in vitro gene transfections by a soluble DNA carrier system. *J. Biol. Chem.*, 262:4429–4432, 1987.

Wu et al., *Genomics*, 4:560, 1989.

Yamaguchi et al., Differential expression of two fibroblast growth factor-receptor genes is associated with malignant progression in human astrocytomas. *Proc. Natl. Acad. Sci. USA*, 91:484–488, 1994.

Yang et al., In vivo and in vitro gene transfer to mammalian somatic cells by particle bombardment. *Proc. Natl. Acad. Sci. USA*, 87:9568–9572, 1990.

Zelenin et al., High-velocity mechanical DNA transfer of the chloramphenicol acetyltransferase gene into rodent liver, kidney and mammary gland cells in organ explants and in vivo. *FEBS Lett.*, 280:94–96, 1991.

What is claimed is:

1. An isolated DNA molecule coding for a tumor suppressor designated TS10q23.3 comprising a nucleic acid sequence, or full complement thereof, encoding the amino acid sequence set forth in SEQ ID NO:1.

2. The DNA molecule of claim 1, wherein said nucleic acid is selected from the group consisting of a murine homolog, a canine homolog and a human homolog.

3. The DNA molecule of claim 2, wherein said nucleic acid is a human homolog which comprises the nucleotide sequence set forth in SEQ ID NO:22 or the full complement thereof.

4. The DNA molecule of claim 2, wherein said nucleic acid is a mouse homolog which comprises the nucleotide sequence set forth in SEQ ID NO:24 or the full complement thereof.

5. The DNA molecule of claim 2, wherein said nucleic acid is a dog homolog which comprises the nucleotide sequence set forth in SEQ ID NO:26 or the full complement thereof.

6. The DNA molecule of claim 1, wherein said nucleic acid is selected from the group consisting of genomic DNA, complementary DNA and RNA.

7. The DNA molecule of claim 5, wherein said nucleic acid is a complementary DNA and further comprises a promoter operably linked to said complementary DNA, or the complement thereof, encoding said tumor suppressor.

8. The DNA molecule of claim 5, further comprising a polyadenylation signal operably linked to said complementary DNA encoding said tumor suppressor.

9. The DNA molecule of claim 8, further comprising an origin of replication.

10. The DNA molecule of claim 9, wherein said nucleic acid further comprises a viral vector selected from the group consisting of a retrovirus, adenovirus, herpesvirus, vaccinia virus, and adeno-associated virus.

11. The DNA molecule of claim 10, wherein said nucleic acid is packaged in a virus particle.

12. The DNA molecule of claim 9, wherein said nucleic acid is packaged in a liposome.

13. An isolated oligonucleotide consisting of about 10 to about 50 consecutive bases of a DNA molecule coding for a tumor suppressor designated TS10q23.3 comprising a nucleic acid sequence, or full complement thereof, encoding the amino acid sequence set forth in SEQ ID NO:1.

14. The oligonucleotide of claim 13, wherein the tumor suppressor is a murine homolog.

15. The oligonucleotide of claim 13, wherein the tumor suppressor is a human homolog.

16. The oligonucleotide of claim 14, wherein the nucleic acid is the coding region of SEQ ID NO:3.

17. The oligonucleotide of claim 15, wherein the nucleic acid is the coding region of SEQ ID NO:2.

18. The oligonucleotide of claim 13, wherein the oligonucleotide is about 15 bases in length.

19. The oligonucleotide of claim 13, wherein the oligonucleotide is about 17 bases in length.

20. The oligonucleotide of claim 13, wherein the oligonucleotide is about 20 bases in length.

21. The oligonucleotide of claim 13, wherein the oligonucleotide is about 25 bases in length.

22. The oligonucleotide of claim 13, wherein the oligonucleotide is about 50 bases in length.

23. An isolated DNA molecule coding for a mutant tumor suppressor designated TS10q23.3 comprising a nucleic acid sequence, or full complement thereof, encoding the amino acid sequence set forth in SEQ ID NO:1 which comprises (a) Arg in place of Leu at amino acid residue 42 or (b) Glu in place of Gly at amino acid residue 36.

24. The DNA molecule of claim 23, wherein said mutant tumor suppressor comprises Arg in place of Leu at amino acid residue 42.

25. The DNA molecule of claim 24, wherein said nucleic acid comprises the nucleotide sequence set forth in SEQ ID NO:22 comprising G in place of T at nucleotide position 125, or the full complement thereof.

26. The DNA molecule of claim 23, wherein said mutant tumor suppressor comprises Glu in place of Gly at amino acid residue 36.

27. The DNA molecule of claim 26, wherein said nucleic acid comprises the nucleotide sequence set forth in SEQ ID NO:22 comprising A in place of G at nucleotide position 107, or the full complement thereof.

28. The DNA molecule of claim 23, wherein said mutation is in a glioma cell.

29. The DNA molecule of claim 23, wherein said mutation is in a prostate cell.

30. The DNA molecule of claim 23, wherein said mutation is in a breast cell.

31. The oligonucleotide of claim 13, wherein the tumor suppressor is a canine homolog.

32. The oligonucleotide of claim 31, wherein the nucleic acid is the coding region of SEQ ID NO:4.

* * * * *

UNITED STATES PATENT AND TRADEMARK OFFICE
CERTIFICATE OF CORRECTION

PATENT NO.     : 6,262,242 B1                                               Page 1 of 1
DATED          : July 17, 2001
INVENTOR(S)    : Peter Steck et al.

It is certified that error appears in the above-identified patent and that said Letters Patent is hereby corrected as shown below:

Column 111,
Lines 46 and 50, please change the dependency of claims 7 and 8 to depend from -- claim 6 --.

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,262,242 B1 |
| APPLICATION NO. | : 08/791115 |
| DATED | : July 17, 2001 |
| INVENTOR(S) | : Steck et al. |

Page 1 of 1

It is certified that error appears in the above-identified patent and that said Letters Patent is hereby corrected as shown below:

Col. 1, line 4, please delete "may own" and insert --has--.

Signed and Sealed this

Third Day of November, 2009

David J. Kappos
*Director of the United States Patent and Trademark Office*